(12) United States Patent  (10) Patent No.: US 8,437,827 B2
Zhang et al.  (45) Date of Patent: May 7, 2013

(54) EXTRUDED ANALYTE SENSORS AND METHODS OF USING SAME

(75) Inventors: Songbiao Zhang, Fremont, CA (US); John C. Mazza, Pleasanton, CA (US); Mohammed Moein, Saratoga, CA (US); Ting Chen, Cedar Park, TX (US)

(73) Assignee: Abbott Diabetes Care Inc., Alameda, CA (US)

( * ) Notice: Subject to any disclaimer, the term of this patent is extended or adjusted under 35 U.S.C. 154(b) by 705 days.

(21) Appl. No.: 12/495,712

(22) Filed: Jun. 30, 2009

(65) Prior Publication Data

US 2010/0326843 A1  Dec. 30, 2010

(51) Int. Cl.
*A61B 5/04* (2006.01)

(52) U.S. Cl.
USPC .................. 600/345; 600/372; 600/373

(58) Field of Classification Search .......... 600/345–361; 204/403.01
See application file for complete search history.

(56) References Cited

U.S. PATENT DOCUMENTS

| | | | |
|---|---|---|---|
| 4,637,403 A * | 1/1987 | Garcia et al. ................. | 600/583 |
| 5,262,035 A | 11/1993 | Gregg et al. | |
| 5,262,305 A | 11/1993 | Heller | |
| 5,264,104 A | 11/1993 | Gregg | |
| 5,264,105 A | 11/1993 | Gregg | |
| 5,320,715 A | 6/1994 | Berg | |
| 5,356,786 A | 10/1994 | Heller | |
| 5,593,852 A | 1/1997 | Heller | |
| 5,899,855 A | 5/1999 | Brown | |
| 5,918,603 A | 7/1999 | Brown | |
| 5,965,380 A | 10/1999 | Heller | |
| 6,071,391 A | 6/2000 | Gotoh | |
| 6,103,033 A | 8/2000 | Say | |
| 6,120,676 A | 9/2000 | Heller | |
| 6,121,009 A | 9/2000 | Heller | |
| 6,134,461 A | 10/2000 | Say | |
| 6,143,164 A | 11/2000 | Heller | |
| 6,156,051 A | 12/2000 | Schraga | |
| 6,162,611 A | 12/2000 | Heller | |
| 6,175,752 B1 | 1/2001 | Say | |
| 6,281,006 B1 | 8/2001 | Heller | |
| 6,284,478 B1 | 9/2001 | Heller | |
| 6,299,757 B1 | 10/2001 | Feldman | |
| 6,329,161 B1 | 12/2001 | Heller | |
| 6,338,790 B1 | 1/2002 | Feldman | |

(Continued)

FOREIGN PATENT DOCUMENTS

| | | |
|---|---|---|
| AU | 784699 | 6/2006 |
| WO | 2007088875 | 8/2007 |
| WO | 2008056598 | 5/2008 |

OTHER PUBLICATIONS

"Detection of Ketosis and Monitoring of Diabetic Ketoacidosis." Chase, H.P. Manag Care. Apr. 2004;13(4 Suppl):5-6; discussion 19-21.*

*Primary Examiner* — Navin Natnithithadha
*Assistant Examiner* — Meredith Weare
(74) *Attorney, Agent, or Firm* — Edward J. Baba; Shweta Chandra; Bozicevic, Field & Francis LLP

(57) ABSTRACT

The present disclosure provides electrode structures and integrated electrode structures having one or more conductive materials coextruded with one or more dielectric materials. The disclosed electrode structures can be configured for use as analyte sensors. Also provided, are methods of making and using the electrode structures and integrated electrode structures described herein.

33 Claims, 71 Drawing Sheets

U.S. PATENT DOCUMENTS

| | | |
|---|---|---|
| 6,461,496 B1 | 10/2002 | Feldman |
| 6,484,046 B1 | 11/2002 | Say |
| 6,503,381 B1 | 1/2003 | Gotah |
| 6,514,718 B2 | 2/2003 | Heller |
| 6,560,471 B1 | 5/2003 | Heller |
| 6,565,509 B1 | 5/2003 | Say |
| 6,579,690 B1 | 6/2003 | Bonnecaze |
| 6,591,125 B1 | 7/2003 | Buse |
| 6,592,745 B1 | 7/2003 | Feldman |
| 6,605,200 B1 | 8/2003 | Mao |
| 6,605,201 B1 | 8/2003 | Mao |
| 6,616,819 B1 | 9/2003 | Liamos |
| 6,618,934 B1 | 9/2003 | Feldman |
| 6,638,716 B2 | 10/2003 | Heller |
| 6,654,625 B1 | 11/2003 | Say |
| 6,676,816 B2 | 1/2004 | Mao |
| 6,684,680 B2 | 2/2004 | Pierskalla et al. |
| 6,736,957 B1 | 5/2004 | Forrow |
| 6,746,582 B2 | 6/2004 | Heller |
| 6,749,618 B2 | 6/2004 | Levaughn |
| 6,749,740 B2 | 6/2004 | Liamos |
| 6,830,551 B1 * | 12/2004 | Uchigaki et al. .............. 600/584 |
| 6,893,545 B2 | 5/2005 | Gotoh |
| 6,932,894 B2 | 8/2005 | Mao |
| 6,942,518 B2 | 9/2005 | Liamos |
| 6,973,706 B2 | 12/2005 | Say |
| 6,990,366 B2 | 1/2006 | Say |
| 7,003,340 B2 | 2/2006 | Say |
| 7,003,341 B2 | 2/2006 | Say |
| 7,041,468 B2 | 5/2006 | Drucker |
| 7,074,308 B2 | 7/2006 | Mao |
| 7,090,756 B2 | 8/2006 | Mao |
| 7,299,082 B2 | 11/2007 | Feldman |
| 7,366,556 B2 | 4/2008 | Brister et al. |
| 7,381,184 B2 | 6/2008 | Funderburk |
| 7,775,975 B2 | 8/2010 | Brister et al. |
| 7,801,582 B2 | 9/2010 | Peyser |
| 7,811,231 B2 | 10/2010 | Jin et al. |
| 7,826,879 B2 | 11/2010 | Hoss et al. |
| 8,000,763 B2 | 8/2011 | Mazza et al. |
| 2001/0054319 A1 | 12/2001 | Heller et al. |
| 2003/0000834 A1 * | 1/2003 | Yoshioka et al. ........ 204/403.01 |
| 2003/0032875 A1 | 2/2003 | Taniike et al. |
| 2003/0199744 A1 * | 10/2003 | Buse et al. .................... 600/347 |
| 2004/0055898 A1 | 3/2004 | Heller et al. |
| 2004/0079653 A1 | 4/2004 | Karinka |
| 2004/0186365 A1 | 9/2004 | Jin |
| 2004/0254434 A1 | 12/2004 | Goodnow |
| 2005/0199494 A1 * | 9/2005 | Say et al. ................. 204/403.01 |
| 2006/0201805 A1 | 9/2006 | Forrow |
| 2006/0224141 A1 * | 10/2006 | Rush et al. .................... 604/503 |
| 2006/0263839 A1 * | 11/2006 | Ward et al. ...................... 435/14 |
| 2007/0042450 A1 | 2/2007 | McGimpsey et al. |
| 2007/0078360 A1 | 4/2007 | Matsumoto et al. |
| 2007/0093704 A1 | 4/2007 | Brister et al. |
| 2007/0149897 A1 | 6/2007 | Ghesquiere et al. |
| 2007/0279839 A1 * | 12/2007 | Miller et al. ................... 361/502 |
| 2008/0086273 A1 * | 4/2008 | Shults et al. ..................... 702/19 |
| 2008/0125751 A1 | 5/2008 | Fjield et al. |
| 2008/0199893 A1 | 8/2008 | Neubert et al. |
| 2008/0214916 A1 * | 9/2008 | Yodfat et al. .................. 600/347 |
| 2008/0267823 A1 | 10/2008 | Wang |
| 2008/0314745 A1 | 12/2008 | Neubert et al. |
| 2009/0093695 A1 * | 4/2009 | Nakamura et al. ............ 600/347 |
| 2009/0099434 A1 | 4/2009 | Liu |
| 2009/0105570 A1 | 4/2009 | Sloan |
| 2009/0159444 A1 | 6/2009 | Ghesquiere et al. |
| 2009/0299225 A1 | 12/2009 | Kitamura et al. |
| 2009/0306696 A1 | 12/2009 | Doi |
| 2010/0069792 A1 | 3/2010 | Fujimura et al. |
| 2010/0326842 A1 | 12/2010 | Mazza et al. |
| 2010/0326843 A1 | 12/2010 | Zhang et al. |
| 2010/0331643 A1 | 12/2010 | Mazza et al. |
| 2010/0331728 A1 | 12/2010 | Zhang et al. |
| 2010/0331771 A1 | 12/2010 | Mazza et al. |

* cited by examiner

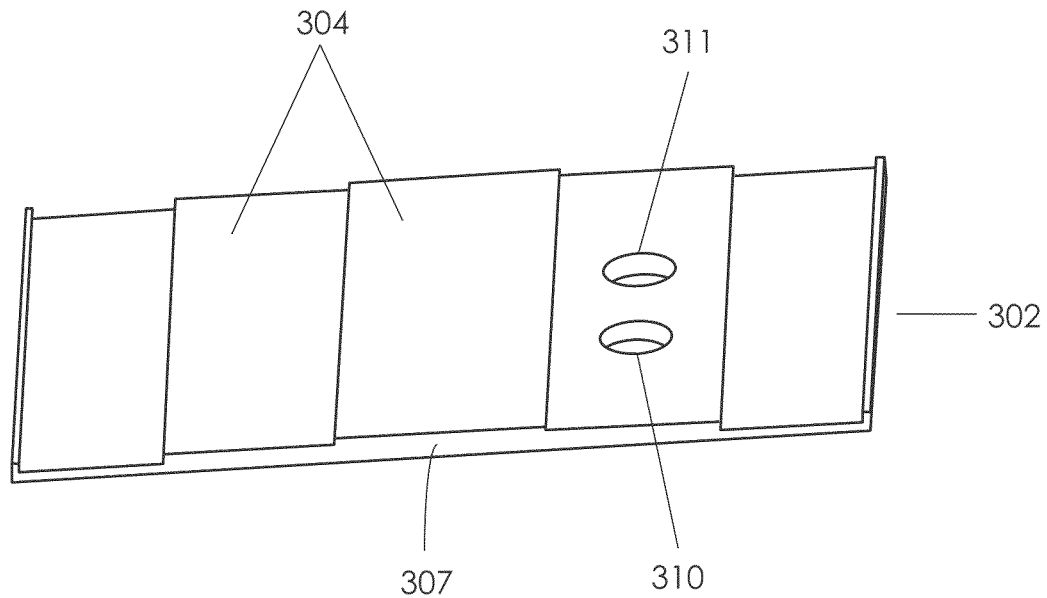
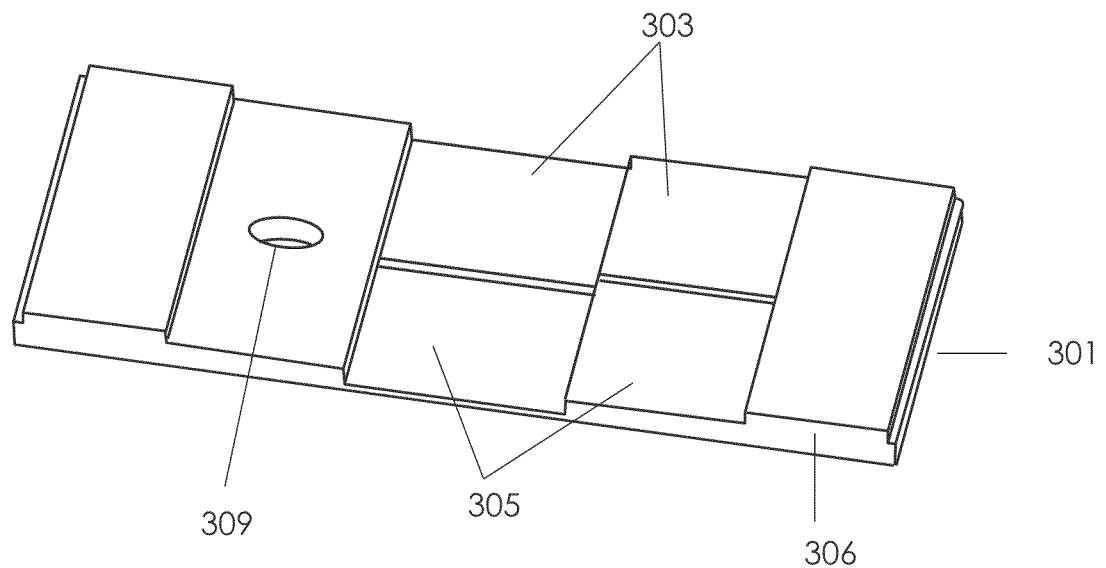
FIG. 10

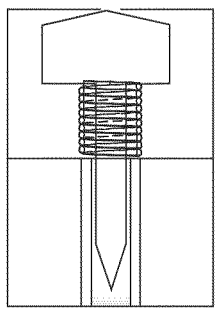
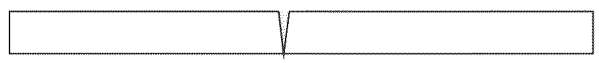
FIG. 14

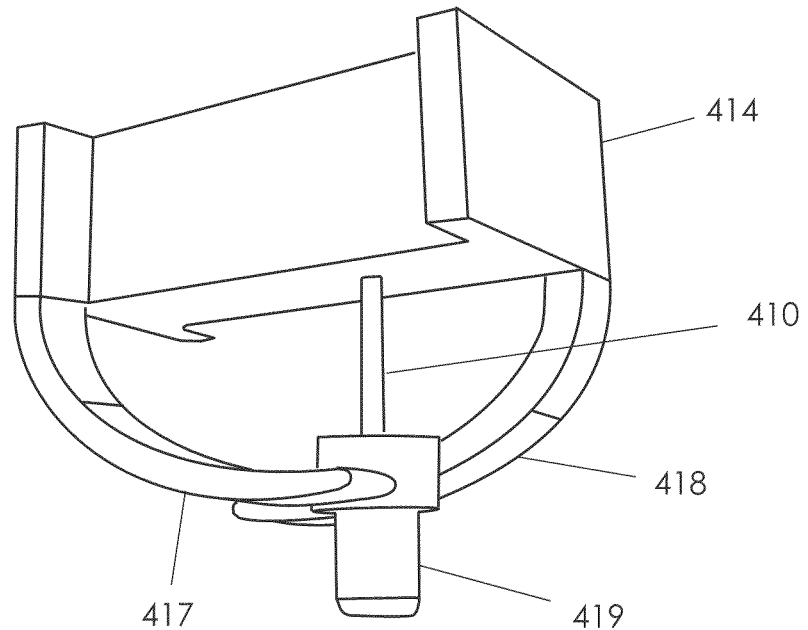
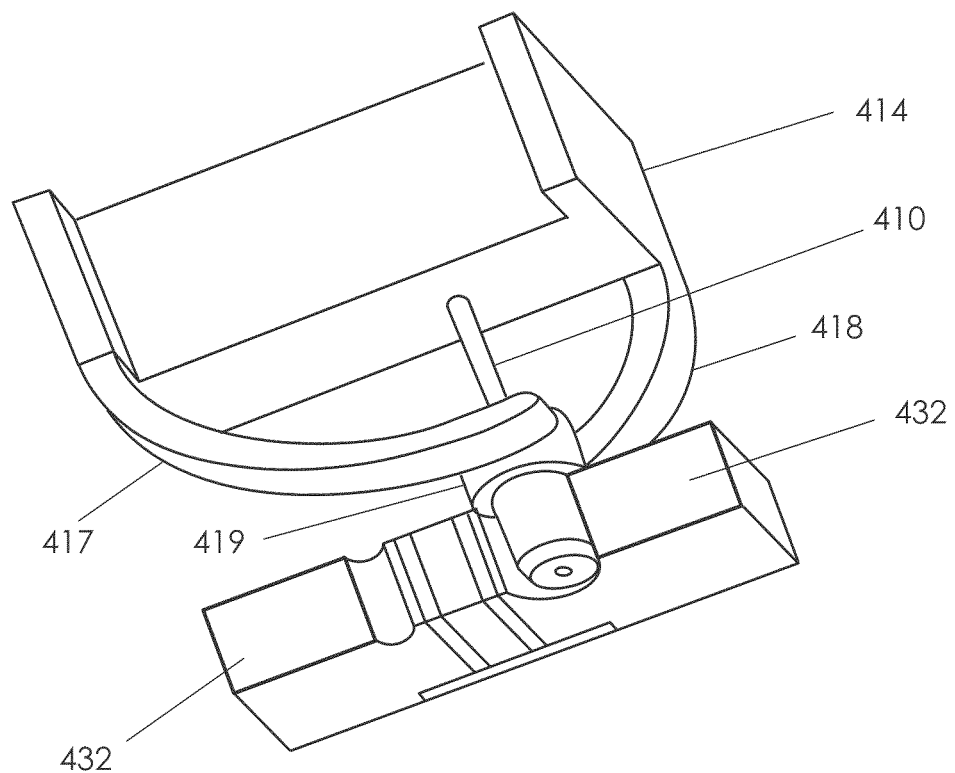
FIG. 18

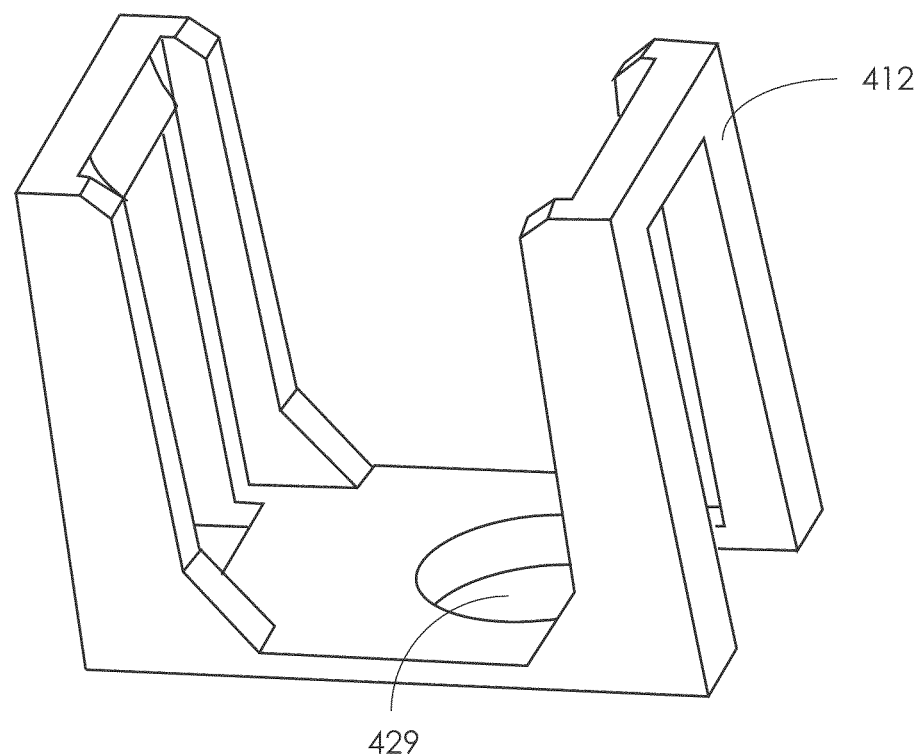
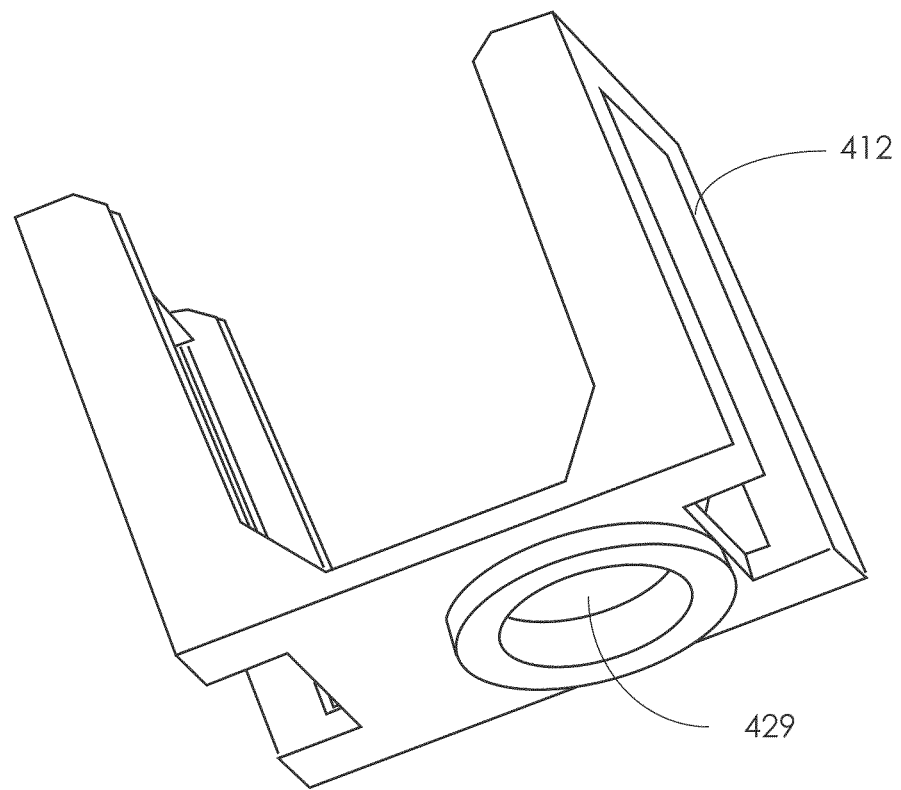
FIG. 19

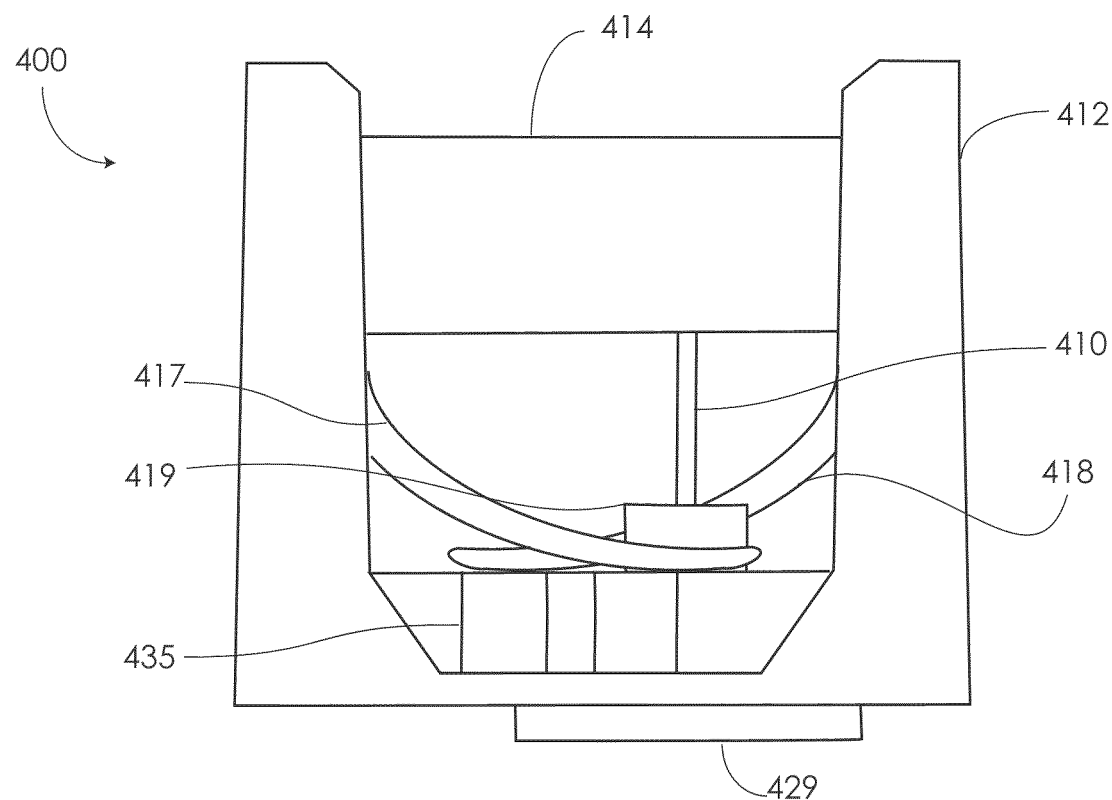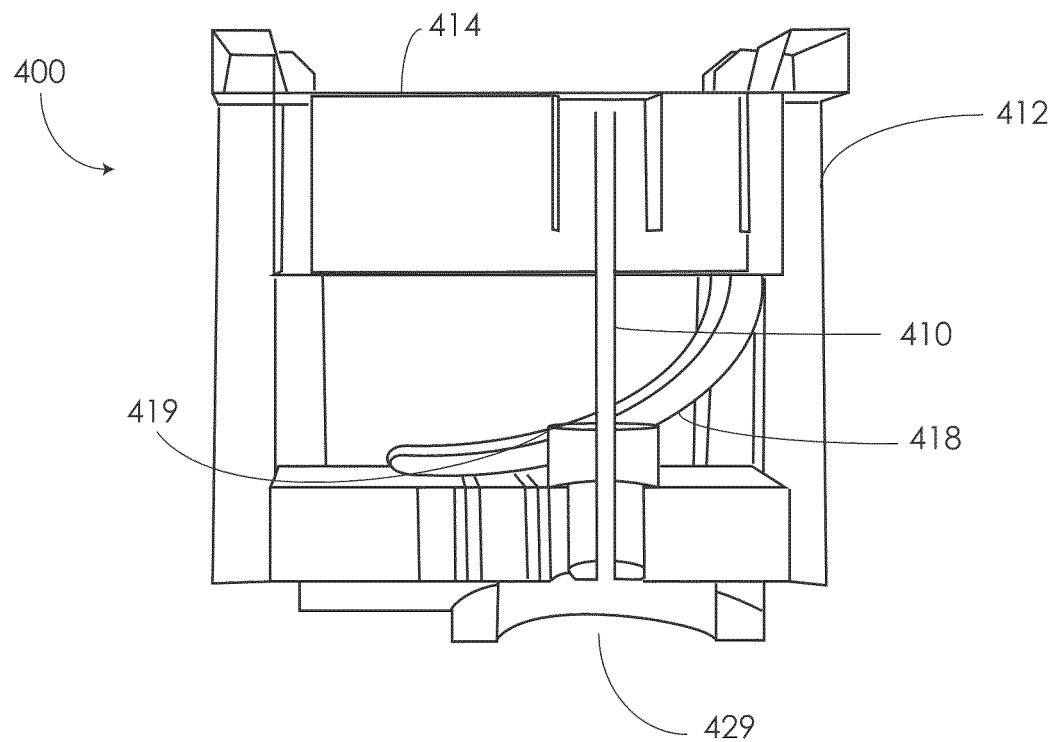
FIG. 20

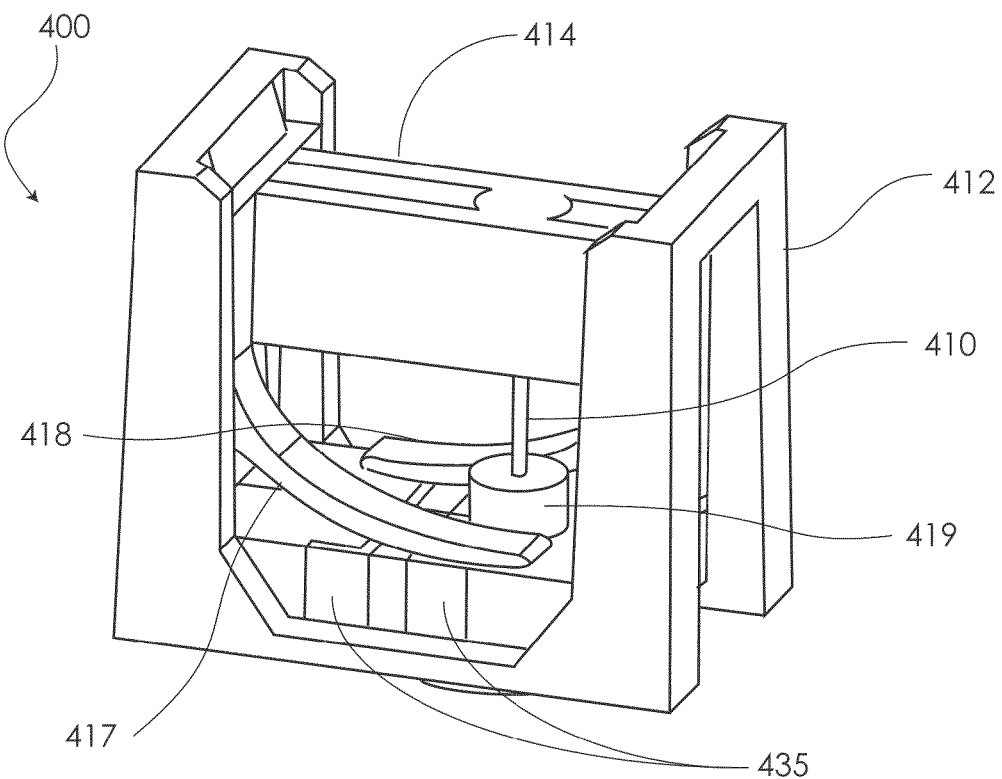
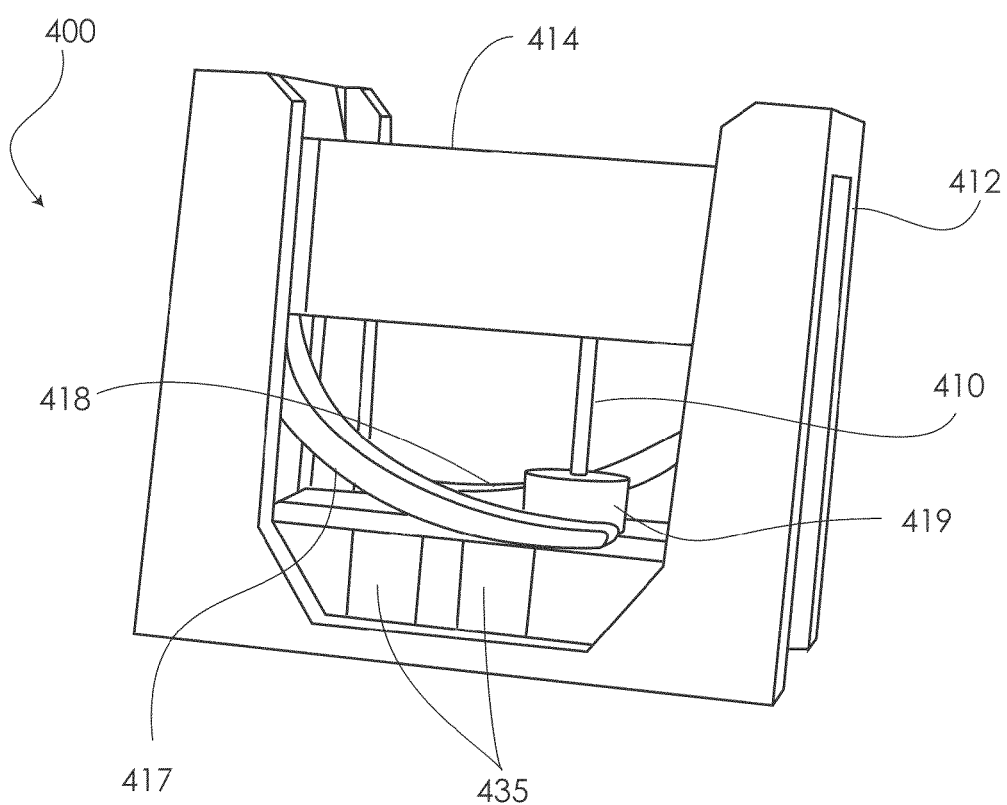
FIG. 21

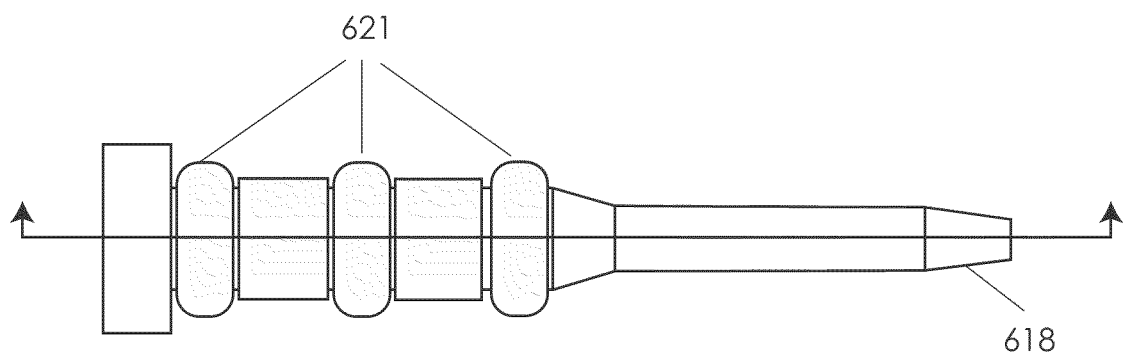
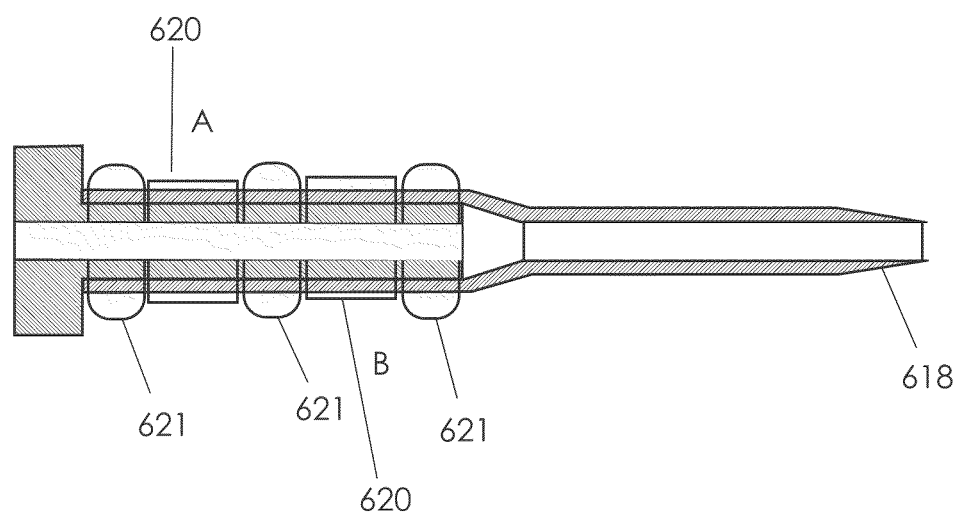
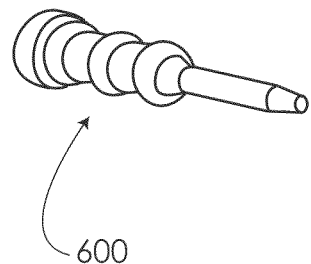
FIG. 49

Samples were cut into small strips. Both ends of each strip were tightly inserted into a gold-plated female connector for stable connection. Resistance was measured across the connectors using a Fluke multimeter.

| Sample Name | Carbon Black Ratio (%) | Dimension (cm) | | | Resistance (KΩ) | Resistivity (Ω·cm) | Mean Resistivity (Ω·cm) |
| --- | --- | --- | --- | --- | --- | --- | --- |
| | | L | W | H | | | |
| 7% Carbon Black | 7 | 12.1 | 0.095 | 0.079 | 28.55 | 17.7 | 21.6 |
| | 7 | 12.1 | 0.096 | 0.059 | 58 | 27.1 | |
| | 7 | 12.2 | 0.095 | 0.055 | 47 | 20.0 | |
| 10% Cardon Black | 10 | 9.7 | 0.094 | 0.07 | 8.88 | 6.1 | 6.3 |
| | 10 | 9.6 | 0.093 | 0.067 | 8.98 | 5.8 | |
| | 10 | 9.6 | 0.093 | 0.073 | 8.8 | 6.3 | |
| | 10 | 9.2 | 0.093 | 0.052 | 13.64 | 7.3 | |
| 13% Carbon Black | 13 | 9.18 | 0.145 | 0.057 | 4.8 | 4.3 | 4.9 |
| | 13 | 9.42 | 0.132 | 0.059 | 6.4 | 5.3 | |
| | 13 | 9.12 | 0.133 | 0.032 | 13 | 6.0 | |
| | 13 | 9.24 | 0.131 | 0.045 | 6.52 | 4.2 | |
| Maximum Required (±10%) | | | | | | 12 | <10.8 |

FIG. 70

EXTRUDED ANALYTE SENSORS AND METHODS OF USING SAME

BACKGROUND OF THE INVENTION

Electrode structures find use in a variety of applications, including, but not limited to, use in electrochemical analyte sensors. Many electrochemical analyte sensors include two or more electrodes in addition to various chemical or biochemical agents. The inclusion of multiple electrodes often requires multiple manufacturing steps which may complicate the manufacturing process and result in increased cost of production. As such, new approaches to the design and manufacture of electrode structures, which simplify the production process and/or reduce the cost of production, are of interest to the art.

SUMMARY OF THE INVENTION

The present disclosure provides electrode structures and integrated electrode structures having one or more conductive materials coextruded with one or more dielectric materials. The disclosed electrode structures can be configured for use as analyte sensors. Also provided, are methods of making and using the electrode structures and integrated electrode structures described herein. These and other objects, features and advantages of the present disclosure will become more fully apparent from the following detailed description of the embodiments, the appended claims and the accompanying drawings.

BRIEF DESCRIPTION OF THE DRAWINGS

The invention is best understood from the following detailed description when read in conjunction with the accompanying drawings. It is emphasized that, according to common practice, the various features of the drawings are not necessarily to-scale. The dimensions of the various features are arbitrarily expanded or reduced for clarity. Included in the drawings are the following figures:

FIG. 10 shows a deconstructed view of an embodiment of an electrode structure according to the present disclosure, wherein the electrode structure includes a first extruded body and a second extruded body;

FIG. 14 shows the integrated lancet and electrode structure of FIGS. 12 and 13 after extraction and collection of the fluid sample;

FIG. 18 shows portions of the integrated lancet and electrode structure shown in FIG. 15;

FIG. 19 shows two different perspective views of the housing for the integrated lancet and electrode structure shown in FIG. 15;

FIG. 20 shows two cross-section views of the integrated lancet and electrode structure shown in FIG. 15;

FIG. 21 shows two different side perspective views of an assembled version of the lancet and electrode structure shown in FIG. 15;

FIG. 24 also shows an exemplary conductive material configuration for the integrated lancet and electrode structure;

FIG. 26 also shows an exemplary conductive material configuration for the integrated lancet and electrode structure;

FIG. 40 also shows a connector suitable for connection to the hollow electrode structure;

FIG. 49 shows three views of a connection configuration in which an electrode structure according to the present disclosure, including a tapered tip, is configured for connection to a staggered connector;

FIG. 70 provides a table which shows the results of resistivity measurements for three blended conductive polymer materials with different percentages of carbon blending;

DETAILED DESCRIPTION OF THE INVENTION

Figure 1A:
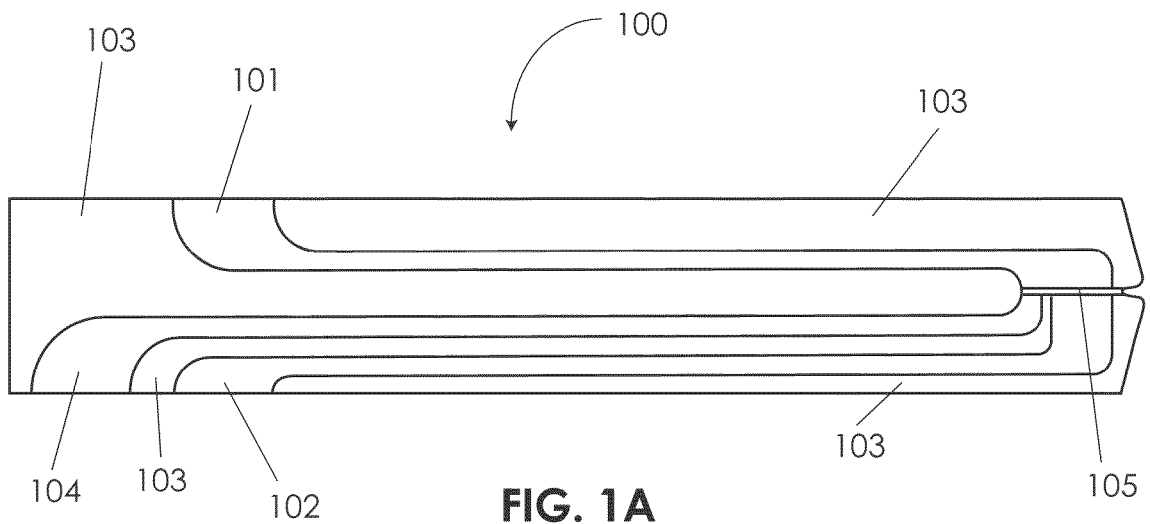
FIG. 1A and FIG. 1B show a cross-section (1A) and a perspective view (1B) of a substantially solid electrode configuration according to the present disclosure.

Before exemplary embodiments are described, it is to be understood that this invention is not limited to particular exemplary embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an electrode structure" includes a plurality of such electrode structures and reference to "the analyte sensor" includes reference to one or more analyte sensors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Extruded Electrode Structures

The present disclosure provides electrode structures which include one or more conductive materials coextruded with one or more dielectric materials. For example, the electrode structures can include 1, 2, 3, 4, or more conductive materials coextruded with 1, 2, 3, 4, or more dielectric materials. In some embodiments, where the electrode structures include a plurality of coextruded conductive materials, at least one coextruded dielectric materials serves to electrically isolate the conductive materials from one another, i.e., at least one dielectric material is coextruded with the plurality of conductive materials such that the plurality of conductive materials are not in electrical communication.

Conductive Materials

A variety of conductive materials are known in the art which may be utilized in connection with the electrode structures of the present disclosure. Generally, the conductive materials should have relatively low electrical resistance and should be electrochemically inert over the potential range of the electrode structure during operation. Suitable conductors include, but are not limited to, gold, carbon, platinum, ruthenium dioxide and palladium, as well as other non-corroding materials known to those skilled in the art. A conductive material for use in the electrode structures of the present disclosure can be a combination of two or more conductive materials, e.g., a blend. An example of a suitable conductive epoxy is ECCOCOAT CT5079-3 Carbon-Filled Conductive Epoxy Coating (available from W.R. Grace Company, Woburn, Mass.).

In some embodiments, conductive materials suitable for use in connection with the disclosed electrode structures include conductive wires or conductive polymers. For example, a suitable conductive material is a blended polymer, e.g., a carbon blended polymer or an Ag/AgCl blended polymer. In one embodiment, where the electrode structure includes a first conductive material and a second conductive material, both the first conductive material and the second conductive material include carbon black and/or carbon nanotube blended polymer. In one embodiment, in addition to carbon black and/or carbon nanotube blended polymer, the second conductive material also includes Ag/AgCl. In one embodiment, an electrode structure according to the present disclosure includes a first conductive material which includes a carbon-blended polymer, a second conductive material which includes a carbon and Ag/AgCl blended polymer, and a dielectric material which includes the same base polymer as the first and second conductive materials.

In one embodiment, a carbon-blended polymer, e.g., a carbon-blended Pebax® (polyether block amides) polymer, is utilized to produce one or more conductive materials of the electrode structures described herein. In one embodiment, a carbon-blended polymer includes from about 7% to about 20% carbon, e.g., carbon black. For example a carbon-blended polymer for use in the disclosed conductive materials can include about 7%, about 8%, about 9%, about 10%, about 11%, about 12%, about 13%, about 14%, about 15%, about 16%, about 17%, about 18%, about 19% or about 20%. In one embodiment, a carbon-blended polymer suitable for use in the electrode structures described herein includes greater than 7% carbon, e.g., greater than 7% carbon black. For example, in such an embodiment, the carbon-blended polymer can include between about 8% and about 20% carbon (e.g., about 8%, about 9%, about 10%, about 11%, about 12%, about 13%, about 14%, about 15%, about 16%, about 17%, about 18%, about 19% or about 20% carbon). In one particular embodiment, a carbon-blended Pebax® polymer having 10% carbon black is utilized. In another embodiment, a carbon-blended Pebax® polymer having 13% carbon black is utilized. Pebax® resin is available from Arkema Inc., Philadelphia, Pa.

Where a polymer is utilized in connection with one or more of the conductive materials, the polymer may be chosen so that the polymer can serve as a flux restricting agent thereby eliminating any potential need for a flux restricting membrane. The polymer may also be chosen for material characteristics that render the polymer relatively stiff when dry and relatively soft when wetted by various bodily fluids.

Conductive materials suitable for use in connection with the disclosed electrode configurations can be colored, e.g., to differentiate between a first conductive material and a second conductive material. In one such embodiment, the first conductive material includes a first color, the second conductive material includes a second color, and the first and second colors are different.

In some embodiments, as described herein, one or more conductive materials are coextruded with one or more dielectric materials.

Dielectric Materials

A variety of dielectric materials are known in the art which may be utilized in connection with the electrode structures of the present disclosure. Suitable dielectric materials include, for example, polymeric or plastic materials and ceramic materials. In some embodiments, the dielectric materials include non-conducting polymers such as polyethylene, polystyrene, polysulfone, and polypropylene. In one embodiment, a suitable dielectric material is a Pebax® polymer.

In some embodiments, the dielectric material or materials are flexible. For example, where an electrode structure as described herein is configured for implantation into a patient, the electrode structure may be made flexible (although rigid electrode structures may also be used for implantable electrode structures) to reduce pain to a patient and damage to the tissue caused by the implantation of and/or the wearing of the electrode structure. A flexible electrode structure can increases a patient's comfort and allow a wider range of activities. Suitable dielectric materials for a flexible electrode structure include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the electrode structures are made using relatively rigid dielectric materials, which, for example, provide structural support against bending or breaking. Examples of rigid dielectric materials include poorly conducting ceramics, such as aluminum oxide and silicon dioxide. Where an electrode structure is to be implanted, one advantage of using a rigid dielectric material is that the electrode structure may have a sharp point and/or a sharp edge to aid in implantation of the electrode structure without an additional insertion device.

It will be appreciated that for many electrode structures and electrode structure applications, both rigid and flexible electrode structures will operate adequately. The flexibility of the electrode structure may also be controlled and varied along a continuum by changing, for example, the composition and/or thickness of the substrate.

In addition to considerations regarding flexibility, it may be desirable, e.g., where the electrode structure is to be wholly or partially implanted under a skin layer of a subject, that the electrode structure include a dielectric material which is physiologically harmless or biocompatible, such as for example, a substrate approved by a regulatory agency or private institution for in vivo use. In some embodiments, suitable dielectric materials may include or be selected from one or more biocompatible materials. A variety of such materials are known in the art, including, but not limited to, High Strength Toughened Fluoropolymer (HSTF), available from WL Gore & Assoc. Inc., Elkton, Md.; and parylene-c.

In some embodiments, a semi-permeable dielectric material may be selected. In such embodiments, the dielectric material may serve as a membrane, e.g., a flux limiting membrane which is semi-permeable to an analyte, e.g., glucose.

In some embodiments of the electrode structures disclosed herein, one or more dielectric materials are coextruded with one or more conductive materials such that one or more of the dielectric materials electrically isolates one or more of the conductive materials.

Electrode Configurations

In one embodiment, an electrode structure according to the present disclosure includes a first conductive material, a second conductive material, and a dielectric material. The first conductive material, the second conductive material, and the dielectric material are coextruded to provide an electrode structure having the first conductive material and the second conductive material electrically isolated by the dielectric material.

The electrode structures described herein have broad utility and can be configured for a variety of in vitro and/or in vivo uses, including, but not limited to, use in analyte detection and/or monitoring, sample collection, and drug delivery. In some embodiments, at least a portion of the electrode structure is adapted for implantation in a subject. For example, the electrode structure can be configured such that at least a portion of the electrode structure can be subcutaneously positioned in a subject. The electrode structure may be wholly implantable in a user or may be configured so that only a portion is positioned within (internal) a user and another portion outside (external) a user. It should be noted that the terms "user," "subject," and "patient" are used interchangeably herein.

Where an electrode structure includes two or more conductive materials, e.g., a first conductive material and a second conductive material, the two or more conductive materials can be the same or different and can be selected from a variety of suitable conductive materials. For example, in one embodiment, the two or more conductive materials include conductive polymers. The electrode structures can be configured such that the two or more conductive materials include different colors which allow for visual differentiation of the two or more conductive materials.

In some embodiments, a biocompatible dielectric material is included in the electrode structures. This biocompatible dielectric material can be coextruded with the two or more conductive materials and/or included as a biocompatible outer layer which at least partially encloses a coextruded layer including two or more conductive materials and one or more dielectric materials.

As indicated above, the electrode structures of the present disclosure can be configured as analyte sensors for use in analyte detection and/or monitoring. In some such embodiments, the electrode structure includes a first conductive material, a second conductive, and a dielectric material, wherein the first conductive material includes a working electrode and the second conductive material includes a reference/counter electrode.

The working electrode includes a conductive material and a sensing layer disposed on, in or proximate thereto, wherein the sensing layer is in electrical communication with the conductive material. The sensing layer may be described as the active chemical area of the analyte sensor. The sensing layer formulation, which can include an analyte-transducing agent/analyte-responsive agent (e.g., a glucose-transducing agent) may include, for example, among other constituents, a redox mediator, such as, for example, a hydrogen peroxide or a transition metal complex, such as a ruthenium-containing complex or an osmium-containing complex, and an analyte response enzyme, such as, for example, a glucose responsive enzyme (e.g., glucose oxidase, glucose dehydrogenase, etc.). The sensing layer may also include other optional components, such as, for example, a polymer and a bi-functional, short-chain, epoxide cross-linker, such as polyethylene glycol (PEG). In some embodiments, the sensing layer includes a metal nanopowder, such as aluminum nanopowder, iron nanopowder, copper nanopowder, nickel nanopowder, magnesium nanopowder, titanium nanopowder, or titanium nitride nanopowder.

In some embodiments, the sensing layer includes an analyte responsive enzyme which is capable of catalyzing a reaction of the analyte. The analyte responsive enzyme can also, in some embodiments, act as an electron transfer agent. There are a variety of suitable analyte responsive enzymes which can be utilized in the sensing layers described herein. For example, glucose oxidase or glucose dehydrogenase (e.g., pyrroloquinoline quinone (PQQ) dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte. Nicotinamide adenine dinucleotide (NAD) dependent hydroxybutyrate dehydrogenase (HBDH) may be used where the analyte of interest is a ketone body.

In certain embodiments, an analyte responsive enzyme may be attached to a polymer, cross linking the analyte responsive enzyme with another electron transfer agent, which, as described below, may be polymeric. An additional catalyst may also be used in certain embodiments. This additional catalyst may be used, for example, to catalyze a reaction of a product compound resulting from the catalyzed reaction of the analyte. The additional catalyst may operate with an electron transfer agent to electrolyze the product compound to generate a signal at the working electrode. Alternatively, an additional catalyst may be provided in an interferent-eliminating layer to catalyze reactions that remove interferents.

In one embodiment, the analyte responsive enzyme is immobilized on an electrode. This is accomplished, for example, by cross linking the analyte responsive enzyme with a redox mediator on the electrode, thereby providing a sensing layer on the electrode, e.g., to create a working electrode.

In another embodiment, the analyte responsive enzyme is disposed adjacent to an electrode to create a working electrode. In such embodiments, the analyte responsive enzyme and redox mediator are generally positioned in close proximity to the electrode in order to provide for electrochemical communication between the analyte responsive enzyme, the redox mediator and the electrode.

In some embodiments, in order to facilitate the electrochemical reaction of the analyte sensor the sensing layer also includes an enzyme cofactor, such as nicotinamide adenine dinucleotide ($NAD^+$) and/or flavin adenine dinucleotide (FAD). For example, where the analyte responsive enzyme is glucose dehydrogenase suitable cofactors include pyrroloquinoline quinone (PQQ), $NAD^+$ and FAD. Additional analyte responsive enzymes and cofactors which may be used in connection with the disclosed sensors are described in U.S. Pat. No. 6,736,957, the disclosure of which is incorporated by reference herein.

A variety of analytes can be detected and quantified using the disclosed electrode structures. Analytes of particular interest include glucose and lactate. Additional analytes that may be determined include, for example, acetyl choline, amylase, bilirubin, cholesterol, chorionic gonadotropin, creatine kinase (e.g., CK-MB), creatine, DNA, fructosamine, glutamine, growth hormones, hormones, ketones (e.g., ketone bodies), oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. No. 6,281,006 and U.S. Pat. No. 6,638,716, the disclosures of each of which are incorporated by reference herein. An analyte monitoring system according to the present disclosure may be configured to monitor a variety of analytes at the same time or at different times.

As indicated above, in some embodiments, in addition to the analyte responsive enzyme, the sensing layer includes a redox mediator. The redox mediator mediates a current between the working electrode and the analyte when present, functioning as an electron transfer agent between the electrode and the analyte. In one embodiment, the redox mediator is immobilized on the working electrode. Materials and methods for immobilizing a redox mediator on an electrode are provided in U.S. Pat. No. 6,592,745, the disclosure of which is incorporated by reference herein. In another embodiment, the redox mediator is disposed adjacent to the working electrode.

Electron transfer agents that may be employed are electroreducible and electrooxidizable ions or molecules having redox potentials that are a few hundred millivolts above or below the redox potential of the standard calomel electrode (SCE). In some embodiments, electron transfer agents having a redox potential ranging from about −200 mV to about +200 mV versus the SCE are utilized. The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine etc. Additional examples include those described in U.S. Pat. No. 6,736,957 and U.S. Patent Publication Nos. 2004/0079653 and 2006/0201805, the disclosures of each of which are incorporated herein by reference.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer including quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents include osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono-, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole). In one specific embodiment, the redox mediator is 1,10 Phenanthrolene-5,6-dione (PQ).

In some embodiments, an analyte responsive enzyme as described herein is crosslinked to a redox polymer as described herein. Addition description of redox polymers, including redox polymers having analyte responsive enzymes crosslinked thereto, can be found in U.S. Pat. Nos. 5,262,035; 5,264,105; 6,605,200; 5,593,852; and 5,356,786; and U.S. patent application Ser. No. 12/051,835, filed Mar. 19, 2008; and Ser. No. 12/172,589, filed Jul. 14, 2008; the disclosures of each of which are incorporated by reference herein.

To prevent electrochemical reactions from occurring on portions of the working electrode not coated by the mediator, a dielectric may be deposited on the electrode over, under, or surrounding the region with the bound redox mediator. Suitable dielectric materials include, e.g., waxes and non-conducting organic polymers such as polyethylene. Dielectric may also cover a portion of the redox mediator on the electrode. The covered portion of the mediator will not contact the sample, and, therefore, will not be a part of the electrode's working surface.

Although it can be advantageous to minimize the amount of redox mediator used, the range for the acceptable amount of redox mediator typically has a lower limit. The minimum amount of redox mediator that may be used is the concentration of redox mediator that is necessary to accomplish the assay within a desirable measurement time period, for example, no more than about 5 minutes or no more than about 1 minute.

The electrode structure can be configured (e.g., by selection of redox mediator, positioning of electrodes, etc.) such that a sensor signal is generated at the working electrode with a measurement period of no greater than about 5 minutes and such that a background signal that is generated by the redox mediator is no more than five times a signal generated by oxidation or reduction of 5 mM glucose. In some embodiments, the analyte sensor is configured such that the background signal that is generated by the redox mediator is the same or less than the signal generated by oxidation or reduction of 5 mM glucose. In some embodiments, the background that is generated by the redox mediator is no more than 25% of the signal generated by oxidation or reduction of 5 mM glucose, e.g., no more than 20%, no more than 15% or no more than 5%.

As indicated above, in some embodiments in which the disclosed electrode structures are configured as analyte sensors, the electrode structures include a first conductive material, a second conductive material, and a dielectric material, wherein the first conductive material includes a working electrode and the second conductive material includes a reference/counter electrode. The term "reference/counter electrode" as used herein refers to an electrode which functions as a reference electrode, a counter electrode, or both a reference and a counter electrode. Generally, the analyte responsive enzyme and redox mediator are positioned relative to the reference and/or counter electrode such that electrochemical communication between the analyte responsive enzyme and the redox mediator and the reference and/or counter electrode is minimized. In one embodiment, the signal at the reference/counter electrode may correspond to background signal which may be removed from the analyte signal obtained from one or more working electrodes by, for example, subtracting the signal.

Where an extruded electrode structure as described herein has been configured for use as an in vivo analyte sensor, a mass transport limiting layer, e.g., an analyte flux modulating layer, may be included with the sensor to act as a diffusion-limiting barrier to reduce the rate of mass transport of the analyte, for example, glucose or lactate, into the region around the working electrode. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating, etc.

Figure 31:
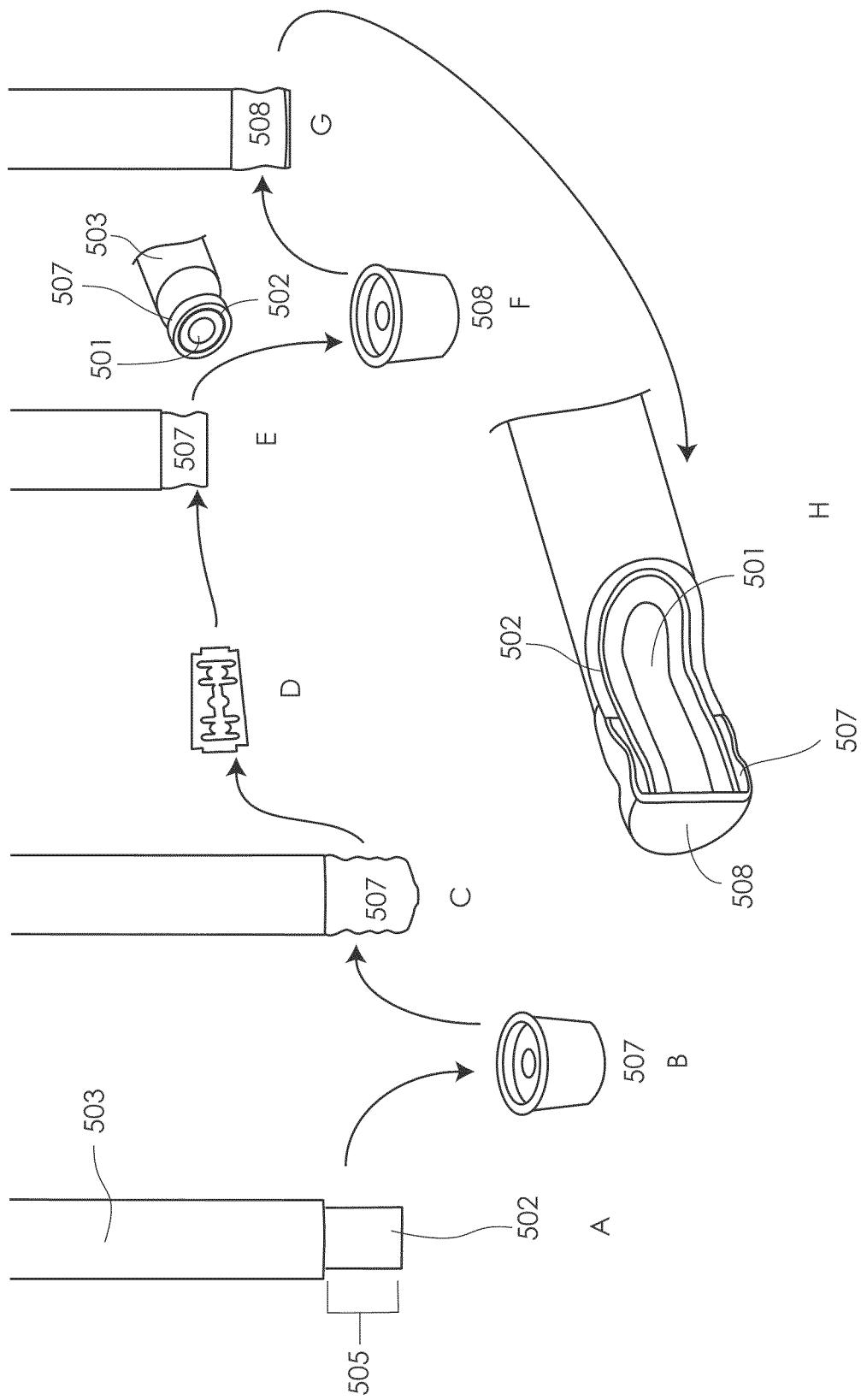
FIG. 31 shows an embodiment, in which an end of a solid, cylindrical electrode structure is configured as a sensing end of an analyte sensor.
Figure 32:
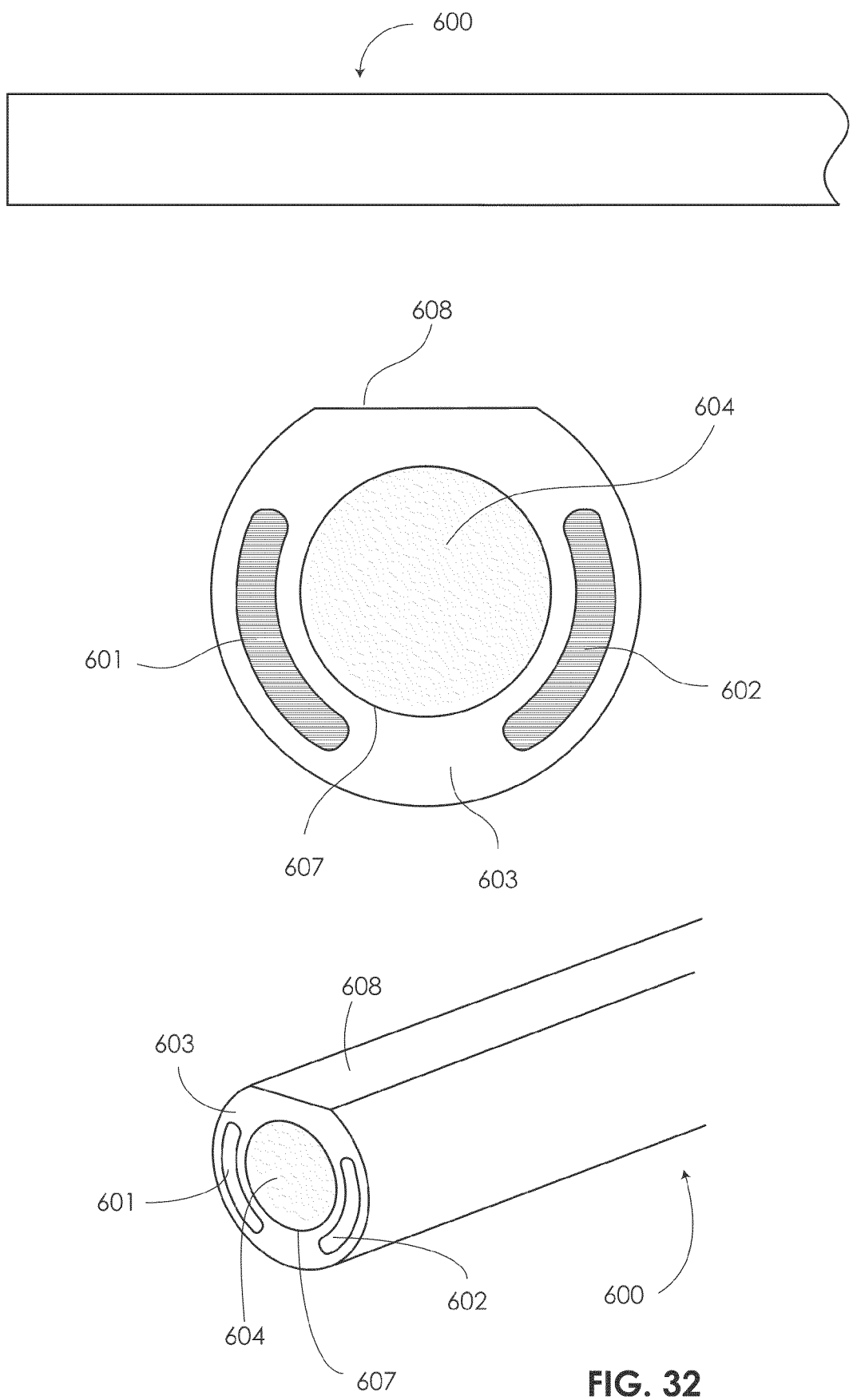
FIG. 32 shows a cross-section and a perspective view of an exemplary hollow electrode structure having a tubular configuration in accordance with the present disclosure.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like. FIG. 31 shows an exemplary embodiment including such a membrane.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over an enzyme-containing sensing layer and allowing the solution to cure for about one to two days or other appropriate time period. The crosslinker-polymer solution may be applied to the sensing layer by placing a droplet or droplets of the solution on the sensor, by dipping the sensor into the solution, or the like. Generally, the thickness of the membrane is controlled by the concentration of the solution, by the number of droplets of the solution applied, by the number of times the sensor is dipped in the solution, or by any combination of these factors. A membrane applied in this manner may have any combination of the following functions: (1) mass transport limitation, i.e., reduction of the flux of analyte that can reach the sensing layer, (2) biocompatibility enhancement, or (3) interferent reduction.

In certain embodiments, the sensing system detects hydrogen peroxide to infer glucose levels. For example, a hydrogen peroxide-detecting sensor may be constructed in which a sensing layer includes enzyme such as glucose oxidase, glucose dehydrogenase, or the like, and is positioned proximate to the working electrode. The sensing layer may be covered by one or more layers, e.g., a membrane that is selectively permeable to glucose. Once the glucose passes through the membrane, it is oxidized by the enzyme and reduced glucose oxidase can then be oxidized by reacting with molecular oxygen to produce hydrogen peroxide.

In some embodiments, electrode structures according to the present disclosure include an indicator element capable of providing a service history for an electrochemical sensor as described in U.S. patent application Ser. No. 12/431,669, filed Apr. 28, 2009, the disclosure of which is incorporated herein by reference.

In some embodiments, electrode structures according to the present disclosure include three or more electrically isolated conductive materials. In some such embodiments, a third conductive material is coextruded with first and second conductive materials. In one embodiment, the electrode structure includes first, second and third conductive materials, wherein the first and second conductive materials include working and reference/counter electrodes respectively and the third conductive material includes a fill-indicator electrode. In another embodiment, the third conductive material includes a thermistor or thermocouple.

In some embodiments, the electrode structures of the present disclosure have a solid or substantially solid configuration. In other embodiments, the electrode structures have a hollow configuration. The electrode structures of the present disclosure can be configured in a variety of shapes and sizes depending on the desired application. Where the electrode structures have a solid or substantially solid configuration, suitable shapes may include, for example, solid or substantially solid cylindrical configurations, or solid or substantially solid rectangular box configurations. Rectangular box configurations may have a configuration which is substantially rectangular. Similarly cylindrical configurations may have a configuration which is substantially cylindrical, and tubular configurations may have a configuration which is substantially tubular. Where the electrode structures have a hollow configuration they can be configured as tubes, i.e., hollow, elongated cylinders. Additional configurations are possible, including, but not limited to, hollow, elongated, rectangular, box configurations. Various configurations and suitable applications for the electrode structures are described in greater detail below with reference to the figures.

Extruded Electrode Structures for In Vitro Use

As indicated above, the present disclosure provides electrode structures, which, in some embodiments, are configured for in vitro use. As used herein, "in vitro use" refers to an extracorporeal use of the electrode structure. For example, use of an electrode structure to detect and/or quantify the level of an analyte in the blood of a subject, wherein the skin of the subject is lanced to produce a blood drop and the electrode structure is brought into contact with the blood drop, is considered an in vitro use. Thus, an electrode structure according to the present disclosure can be configured as an in vitro analyte sensor (i.e., a discrete monitoring sensor). A variety of suitable configurations is available for such electrode structures including, but not limited to, electrode structures having solid or substantially solid configurations, and electrode structures having hollow configurations. Exemplary embodiments of these configurations are described in greater detail below with reference to the figures.

Solid Configurations

Figure 1B:
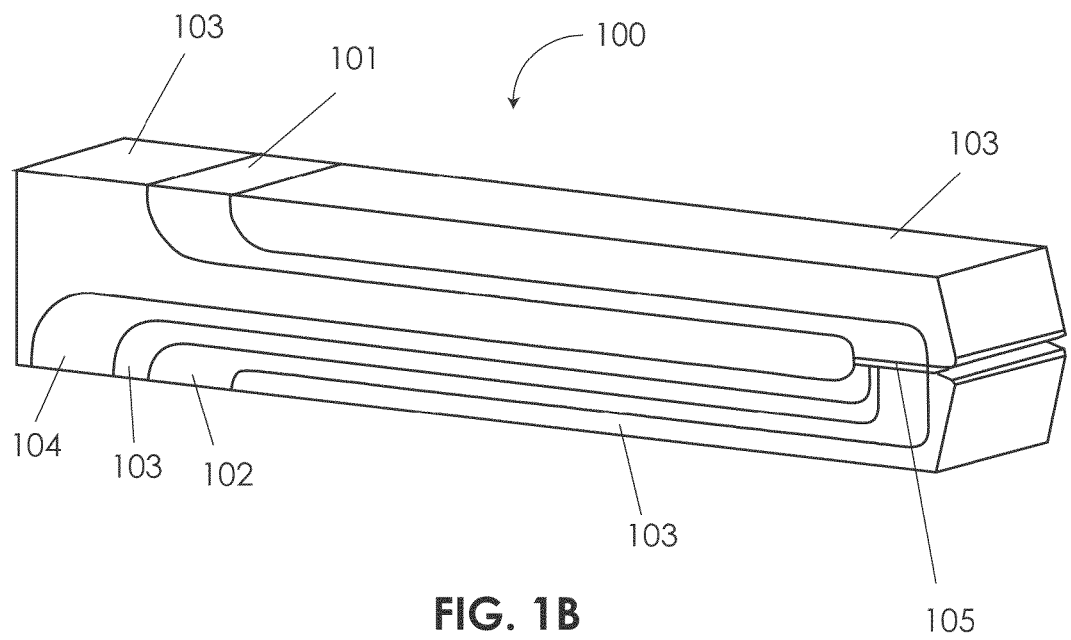

In some embodiments, the electrode structures of the present disclosure have a solid or substantially solid configuration. One such embodiment is depicted in FIGS. 1A and 1B, which show an electrode structure 100, which includes a first conductive material 101, a second conductive material 102, and a dielectric material 103. The electrode structure 100 depicted in FIGS. 1A and 1B also includes an optional third conductive material 104. The conductive materials and the dielectric material are coextruded to provide an electrode structure having the first conductive material 101 and the second conductive material 102 electrically isolated by the dielectric material 103. In the embodiment shown in FIGS. 1A and 1B, optional conductive material 104 is also electrically isolated by dielectric material 103.

It is not necessary that the dielectric material completely surround the conductive materials in order to electrically isolate the conductive materials. Instead, the dielectric material may serve to separate portions of the conductive materials from each other while remaining portions of the conductive materials are separated via their physical spacing in the electrode configuration. For example, as shown in FIGS. 1A and 1B, the conductive materials (101, 102 and 104) can be separated from one another by the dielectric material 103 as well as by the physical spacing of the conductive materials themselves. In FIGS. 1A and 1B, the first conductive material 101 is separated from the second and third conductive materials by dielectric material 103. The first conductive material 101 is also separated form the second and third conductive materials (102 and 104) by a gap 105 between the first conductive material 101 and the second and third conductive materials (102 and 104). When the electrode structure is configured for use as an analyte sensor, this gap or space can provide a reaction chamber for reaction of a fluid sample with components of the analyte sensor.

In exemplary embodiments, the thickness of the reaction chamber is small to promote rapid electrolysis of the analyte, as more of the sample will be in contact with the electrode surface for a given sample volume. Typically, the thickness of the reaction chamber is no more than about 0.2 mm. In some embodiments, the thickness of the reaction chamber is no more than about 0.1 mm, no more than about 0.05 mm, or less.

Where the electrode structures have a solid or substantially solid configuration, suitable shapes may include, for example, solid or substantially solid cylindrical configurations; and solid or substantially solid rectangular box configurations.

The electrode structure of FIGS. 1A and 1B can be configured for use as an analyte sensor. In such an embodiment, the first conductive material 101 can include a working electrode which includes a sensing layer disposed on, in or proximate thereto, the second conductive material 102 can include a reference/counter electrode, and the optional third conductive material 104 can be configured as a fill-indicator electrode. Analyte sensors according to the present disclosure can be configured to measure the level of an analyte in a small sample volume, e.g., a sample volume of less than about 1 µL, e.g., no more than about 500 nL, no more than about 100 nL, no more than about 75 nL, or no more than about 50 nL.

Hollow Configurations

Figure 2:
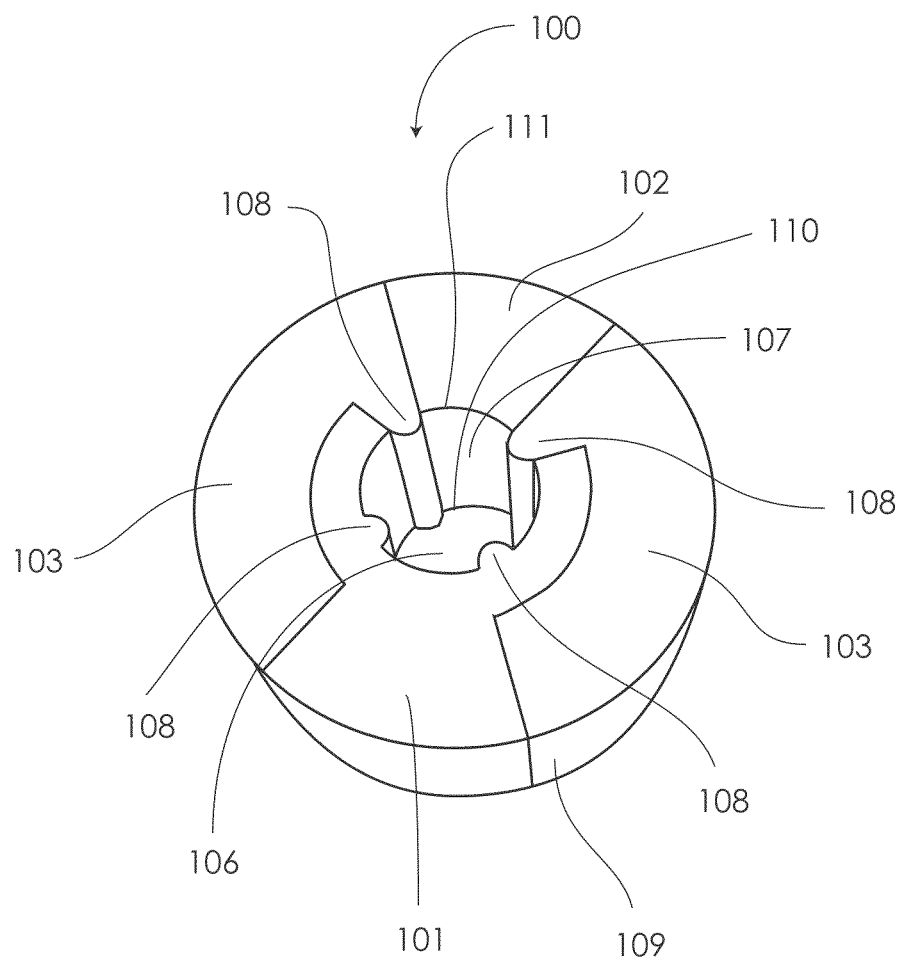
FIG. 2 shows a perspective view of a hollow, cylindrical extruded electrode configuration.

In some embodiments, the electrode structures of the present disclosure have a hollow configuration. In one such embodiment, as shown in FIG. 2, an electrode structure 100 according to the present disclosure includes a first conductive material 101, a second conductive material 102, and a dielectric material 103. The conductive materials and the dielectric material are coextruded to provide an electrode structure having the first conductive material and the second conductive material electrically isolated by the dielectric material. In addition, where the electrode structure has a hollow configuration, the electrode structure includes one or more lumens 106, where each of the one or more lumens includes a first opening 110, a second opening 111, and a lumen wall 107. In some embodiments, e.g., as shown in FIGS. 2-7, the lumen extends the length of the electrode structure with the first opening 110 positioned at one end and the second opening 111 positioned at the opposite end. In some embodiments, hollow electrode structures according to the present disclosure include multiple lumens, e.g., 2, 3, 4, or more lumens. The electrode structures can be configured such that these lumens extend the length of the electrode structures thereby providing multiple passageways through the electrode structures. The lumens described in connection with the embodiments discussed herein are not limited to a particular cross-sectional size or shape as a variety of different cross-sectional sizes and shapes may be utilized.

As with the solid configurations described above, a variety of configurations is possible for the hollow electrode structures described herein. These include, for example, rectangular box configurations and cylindrical configurations, among others.

In FIGS. 2-7, exemplary hollow, cylindrical configurations are described which are suitable, for example, for in vitro use.

With reference to FIGS. 2-7, an electrode structure 100 is provided, wherein the first conductive material 101 and the second conductive material 102 are coextruded with the dielectric material 103 such that each of the first conductive material 101, the second conductive material 102, and the dielectric material 103 define a portion of a lumen wall 107.

Figure 3:
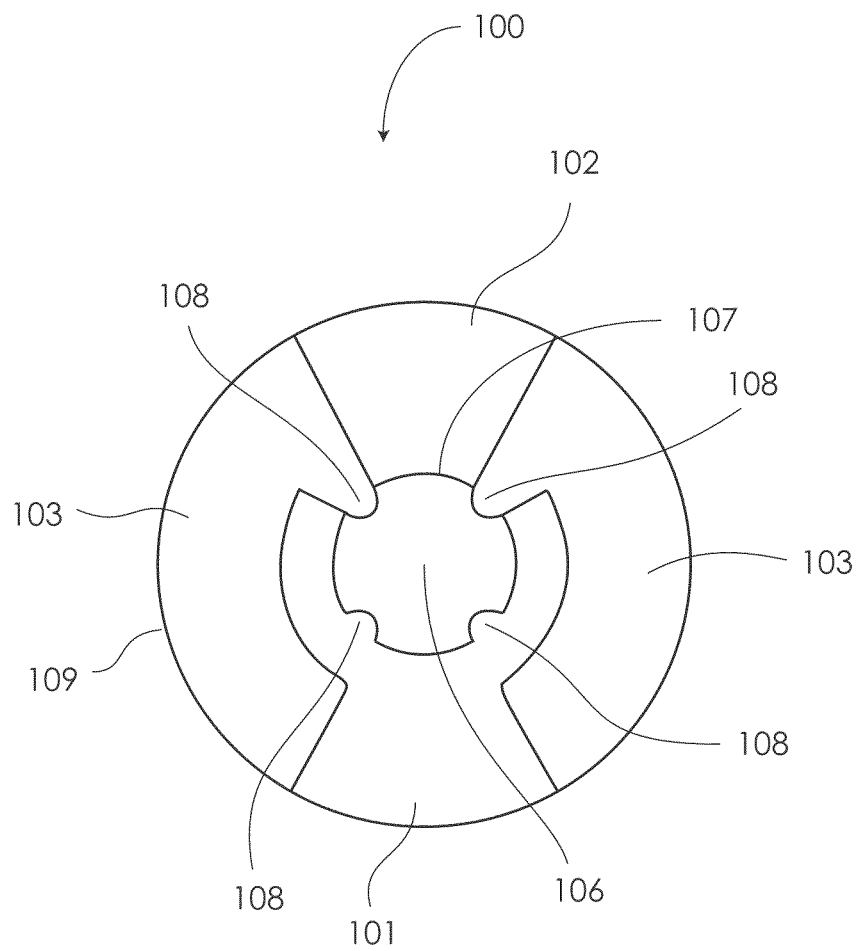
FIG. 3 shows a side view of the hollow, cylindrical configuration shown in FIG. 2.

FIGS. 2 and 3 show two different views of an electrode structure 100. In some embodiments, as shown in FIGS. 2 and 3, the electrode structure is extruded such that the surface area of lumen wall 107 defined by first conductive material 101 is significantly greater than the surface area of lumen wall 107 defined second conductive material 102. In addition, in the embodiment shown in FIGS. 2 and 3, the dielectric material 103 defines a smaller portion of the surface area of the lumen wall 107 relative to the portion defined by conductive materials 101 and 102.

In some embodiments, the electrode structure 100 includes a plurality of optional lancet stand-offs 108. These lancet stand-offs allow the electrode structure 100 to be used with a lancet (not shown), e.g., a lancet designed to lance the skin of a patient in connection with the monitoring of glucose levels. The lancet stand-offs are positioned such that a lancet can slidably engage the lumen wall 107 without simultaneously contacting conductive materials 101 and 102. This may be important, for example, where simultaneous contact between the lancet and conductive materials 101 and 102 would cause an electrical short. In the embodiment shown in FIGS. 2 and 3, the lancet stand-offs 108 are portions of first conductive material 101 and dielectric material 103 which extend inward towards the cylinder axis.

In one embodiment of the electrode structure 100, e.g., as shown in FIGS. 2 and 3, the electrode structure 100 is configured to detect and/or quantitate an analyte in a fluid sample. In such an embodiment, first conductive material 101 includes a working electrode and second conductive material 102 includes a reference/counter electrode. In such embodiments, the electrode structure can be configured such that a fluid sample is drawn through the lumen 106 of the electrode structure by capillary action during analyte detection and/or quantitation. In these embodiments, the lumen 106, or a portion thereof, provides a reaction chamber for reaction of the fluid sample with components of the analyte sensor.

In such embodiments, the dimensions of the reaction chamber can vary based on the volume of the lumen and the location of the sensing layer relative to the conductive materials. In one embodiment, the reaction chamber has a volume of about 75 nl to about 125 nl, e.g., about 80 nl to about 120 nl, about 85 nl to about 115 nl, about 90 nl to about 110 nl, about 95 nl to about 105 nl, or about 100 nl.

Figure 4:
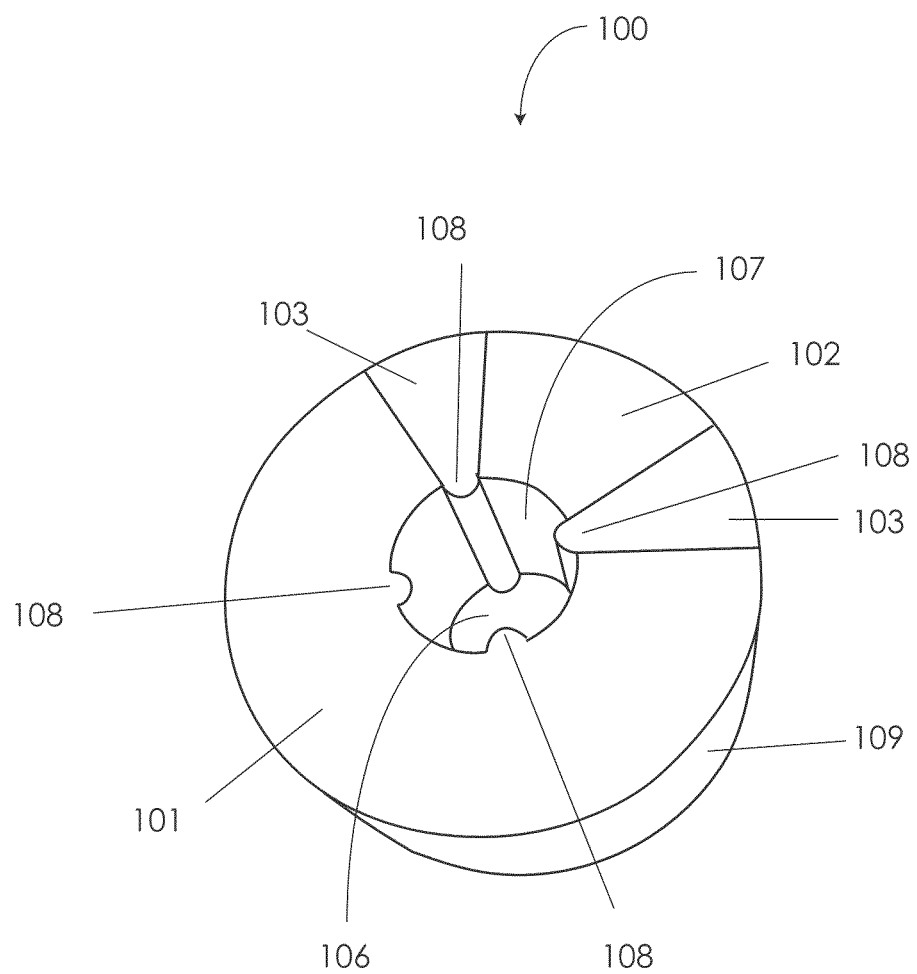
FIG. 4 shows a perspective view of another embodiment of a hollow, cylindrical electrode configuration.
Figure 5:
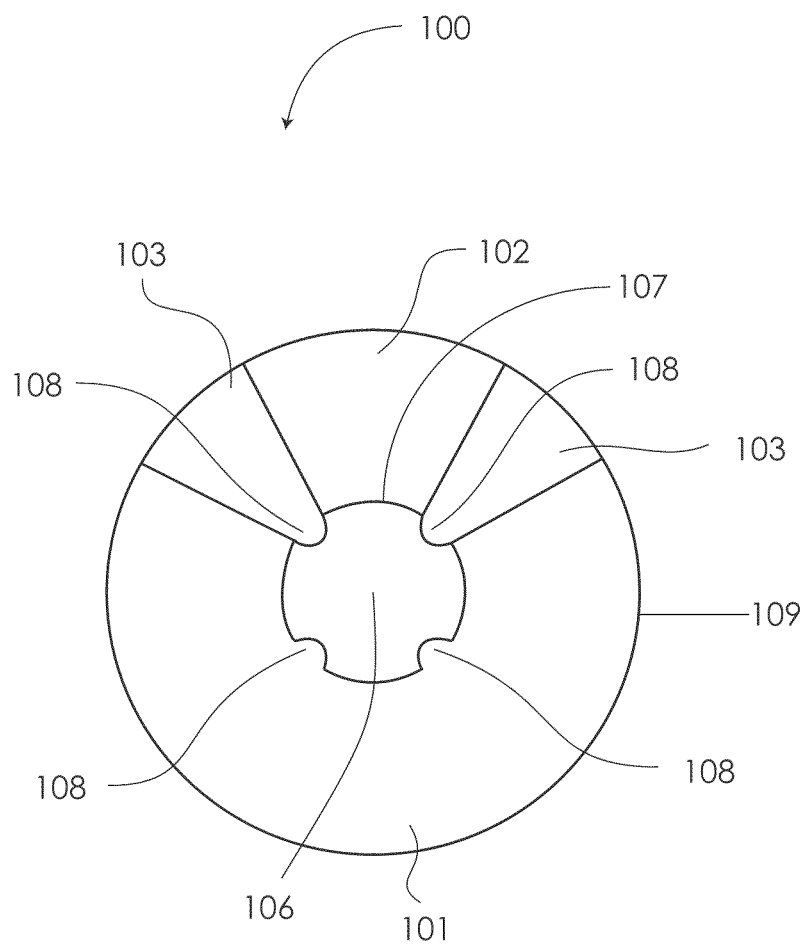
FIG. 5 shows a side view of the hollow, cylindrical electrode configuration shown in FIG. 4.

FIGS. 4 and 5 show two different views of a hollow, cylindrical electrode structure 100 having a lumen 106 and a lumen wall 107. In some embodiments, as shown in FIGS. 4 and 5, the electrode structure is extruded such that the surface area of lumen wall 107 defined by first conductive material 101 is significantly greater than the surface area of lumen wall 107 defined second conductive material 102. In addition, in the embodiment shown in FIGS. 4 and 5, the dielectric material 103 defines a smaller portion of the surface area of the lumen wall 107 relative to the portion defined by conductive materials 101 and 102. The embodiment shown in FIGS. 4 and 5 differs from that shown in FIGS. 2 and 3 in that in FIGS. 4 and 5 the dielectric material 103 makes up less of the outer surface 109 of the electrode structure 100.

As with the electrode structure depicted in FIGS. 2 and 3, the electrode structure 100 shown in FIGS. 4 and 5 includes a plurality of optional lancet stand-offs 108.

In one embodiment of the electrode structure 100 shown in FIGS. 4 and 5, the electrode structure 100 is configured to detect and/or quantitate an analyte in a fluid sample. In such an embodiment, first conductive material 101 includes a working electrode and second conductive material 102 includes a reference/counter electrode.

Figure 6:
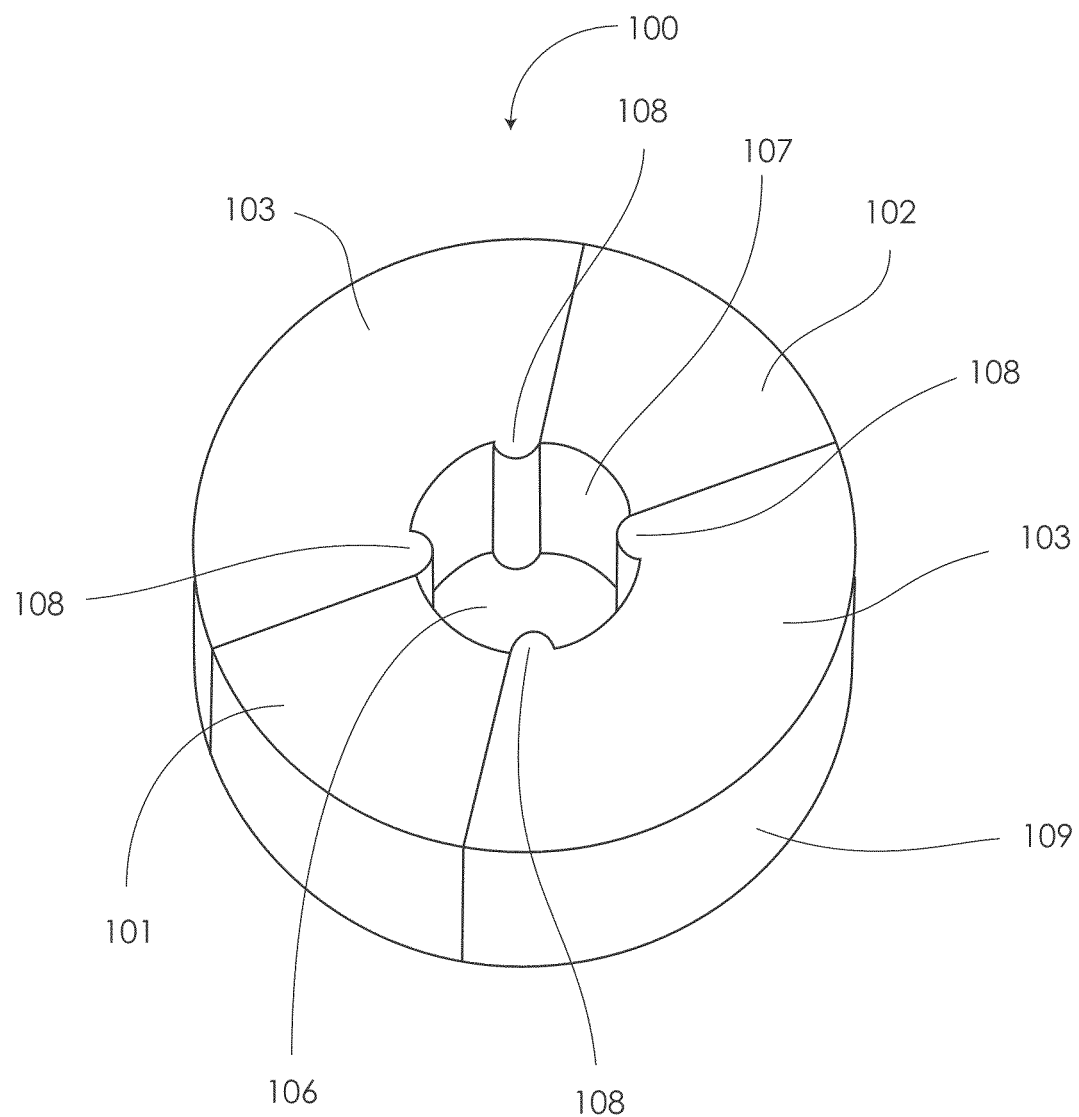
FIG. 6 shows a perspective view of another embodiment of a hollow, cylindrical electrode configuration.
Figure 7:
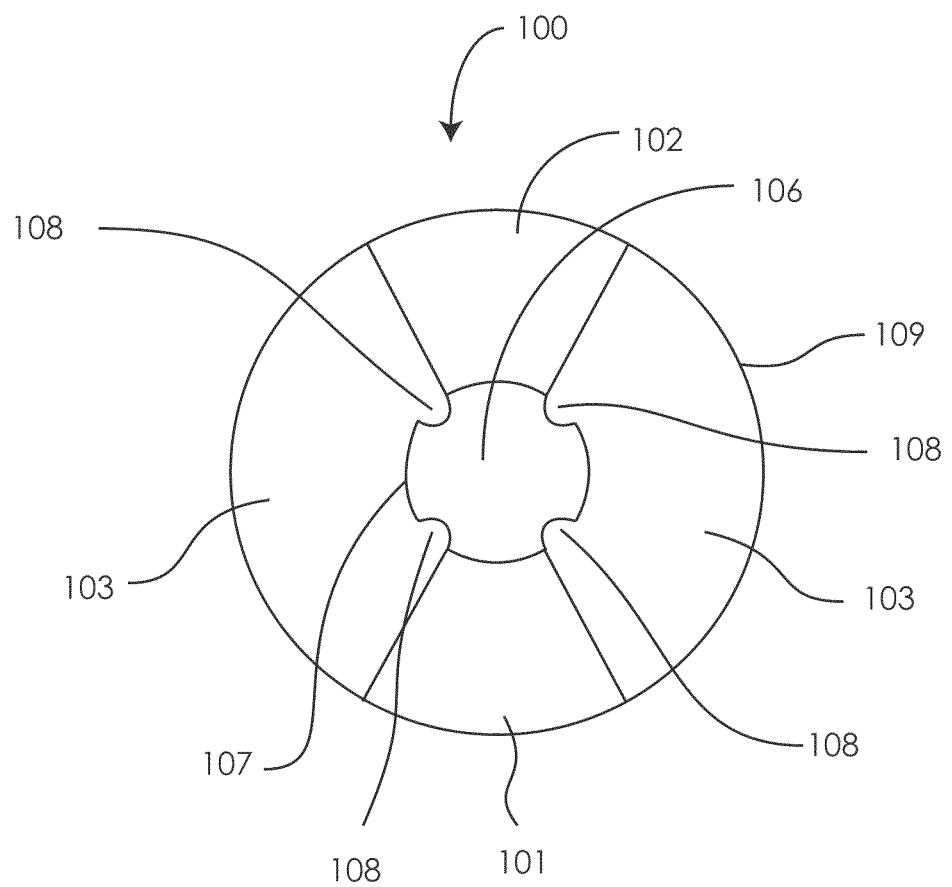
FIG. 7 shows a side view of the hollow, cylindrical electrode configuration shown in FIG. 6.

FIGS. 6 and 7 show two different views of another hollow, cylindrical electrode structure 100 having a lumen 106 and a lumen wall 107. The embodiment shown in FIGS. 6 and 7 differ from those of FIGS. 2-5 in that the surface area of lumen wall 107 defined by first conductive material 101 is not significantly greater than the surface area of lumen wall 107 defined by second conductive material 102. In addition, in the embodiment shown in FIGS. 6 and 7, the dielectric material 103 does not defines a smaller portion of the surface area of the lumen wall 107 relative to the portion defined by conductive materials 101 and 102. Finally, the embodiment shown in FIGS. 6 and 7 differs from those of FIGS. 2-5 in that the optional lance stand-offs 108 are formed from dielectric material 103 and not from either of conductive materials 101 or 102.

In one embodiment of the electrode structure 100 shown in FIGS. 6 and 7, the electrode structure 100 is configured to detect and/or quantitate an analyte in a fluid sample. In such an embodiment, first conductive material 101 includes a working electrode and second conductive material 102 includes a reference/counter electrode.

In some embodiments, where the hollow electrode structures are configured for in vitro use, they include a hole which extends through the dielectric material of the electrode structure and is at least substantially perpendicular to the lumen. This hole can be created in a variety of ways, including, but not limited to, mechanical or laser drilling. The hole can serve to disrupt the capillary effect that occurs when one end of the electrode structure is placed in contact with a fluid sample, e.g., a blood drop. The distance from the holes to the fluid sample-collecting end of the electrode structure can be selected so that the total uptake volume of fluid sample due the capillary effect can be controlled.

Additional components can be added to the hollow electrode structures to enhance their functionality. For example, in one embodiment, the electrode structure includes one or more rigid materials provided, e.g., embedded, in the dielectric material and coextruded with the first conductive material, the second conductive material, and the dielectric material. In one embodiment, the rigid material extends from the proximal end of an electrode structure having proximal and distal ends and functions as a lancet.

In another embodiment, the rigid material includes a third conductive material. This third conductive material can be the same or different as the first and second conductive materials which are coextruded with the dielectric material to produce the hollow electrode structure. In one embodiment, the one or more rigid materials include a third conductive material and the electrode structure includes a hole extending through the dielectric material and at least substantially perpendicular to the lumen. The hole exposes the one or more rigid materials which can serve as a fill indicator. In one such embodiment, when a fluid sample fills the electrode structure up to the hole, the fluid sample contacts the portion of the one or more rigid materials exposed by the hole thereby creating an electrical short which indicates filling of the electrode structure.

Figure 8:
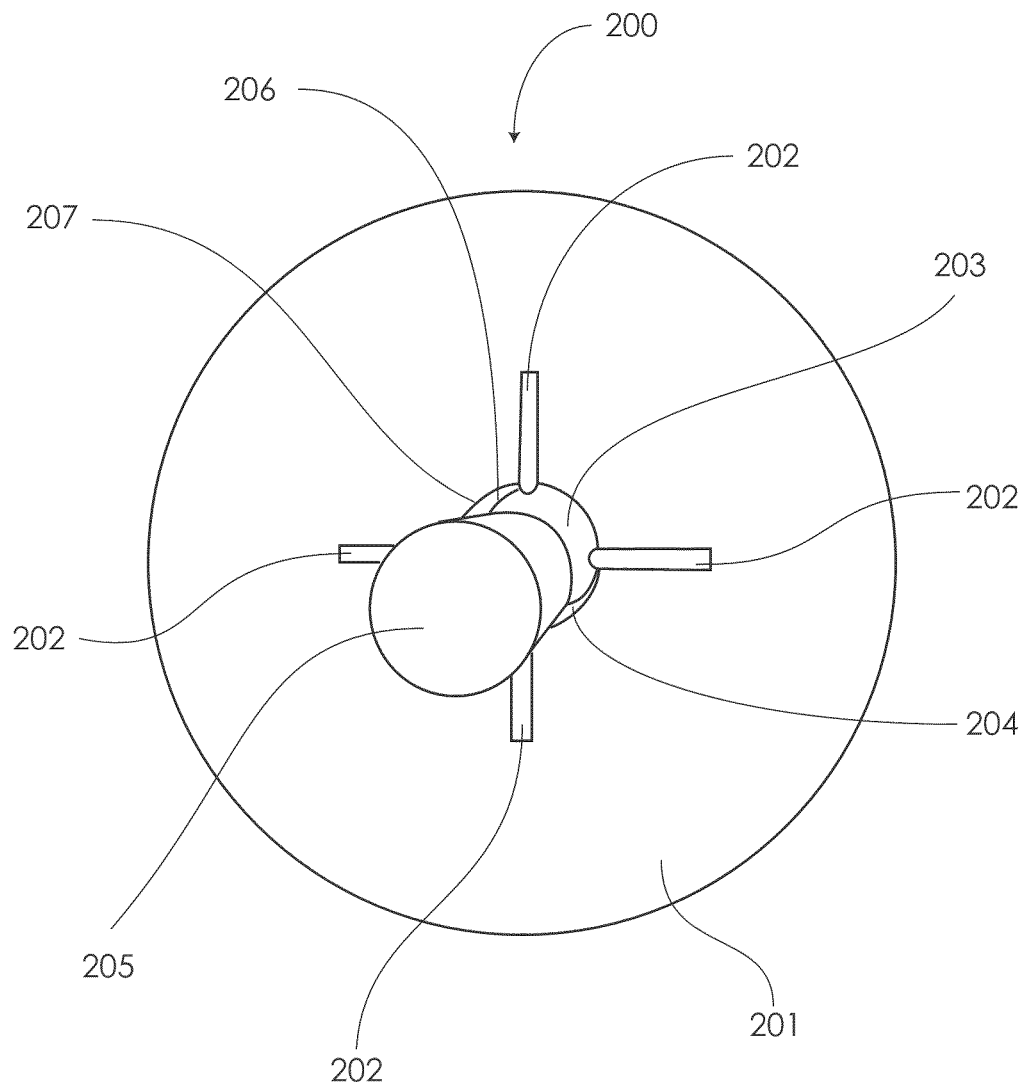
FIG. 8 shows a perspective view of another embodiment of a hollow, cylindrical electrode configuration, including an integrated lancet.
Figure 9:
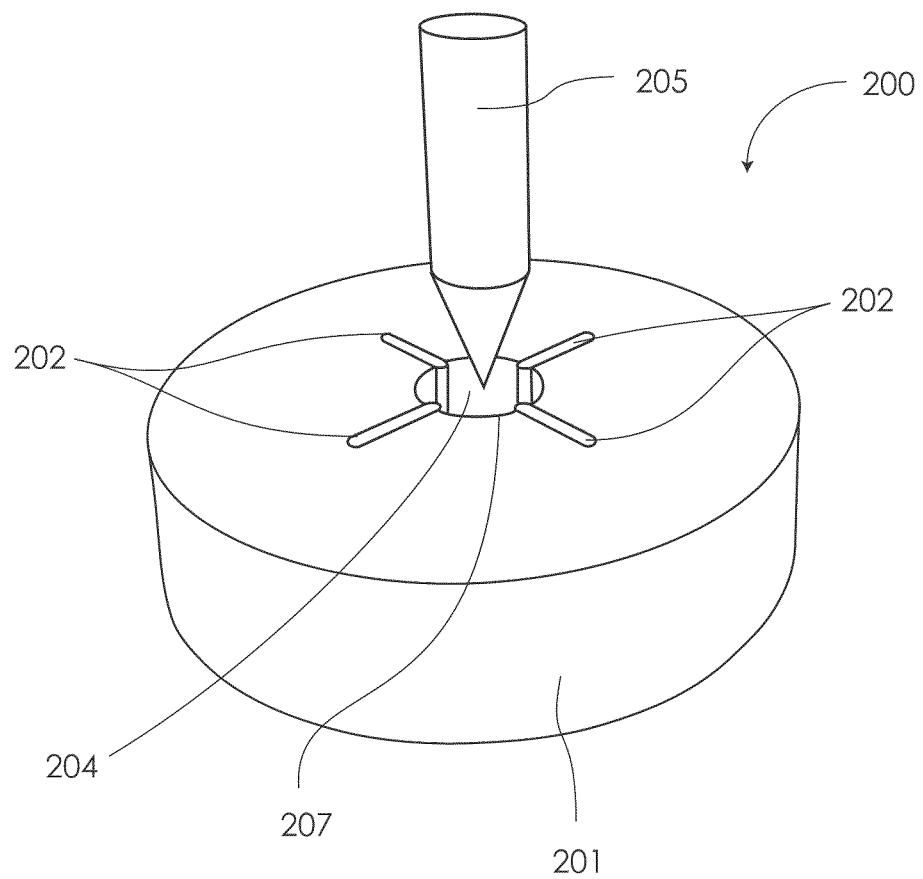
FIG. 9 shows a second perspective view of the cylindrical electrode configuration shown in FIG. 8.

A variation on the embodiments shown in FIGS. 2-7 is provided in FIGS. 8 and 9. FIGS. 8 and 9 show two different views of an integrated electrode structure 200 which includes a first conductive material 201 and a dielectric material 202. The first conductive material 201 and the dielectric material 202 are coextruded to provide an electrode structure which includes a lumen 203, wherein the lumen includes a first opening 206, a second opening 207 and a lumen wall 204. The first conductive material 201 and the dielectric material 202 each define a portion of the lumen wall 204, and the portion of the lumen wall 204 defined by the dielectric material 202 extends into the lumen beyond the portion of lumen wall 204 defined by the first conductive material 201 thereby providing a dielectric stand-off. Integrated electrode structure 200 also includes a lancet 205 which includes a second conductive material. The lancet 205 is slidably positioned within the lumen 203 such that it contacts the portion of lumen wall 204 defined by the dielectric material 202 and not the portion of lumen wall 204 defined by the first conductive material 201. In other words, the conductive lance is positioned to slidably engage the dielectric stand-off provided by dielectric material 202.

In one embodiment, the integrated electrode structure 200 is configured to detect and/or quantitate an analyte in a fluid sample. In such an embodiment, the first conductive material includes a working electrode, and the lancet 205 includes a reference/counter electrode.

Additional Configurations

Where the electrode structures are designed for in vitro use, a variety of additional configurations are possible. For example, in one embodiment, an electrode structure according to the present disclosure includes a first extruded body which includes a first conductive material coextruded with a first dielectric material. The electrode structure also includes a second extruded body which includes a second conductive material coextruded with a second dielectric material. The electrode structure is configured such that the first conductive material is electrically isolated from the second conductive material. In one such embodiment, the first extruded body and the second extruded body are snapedly engaged.

Figure 11A:
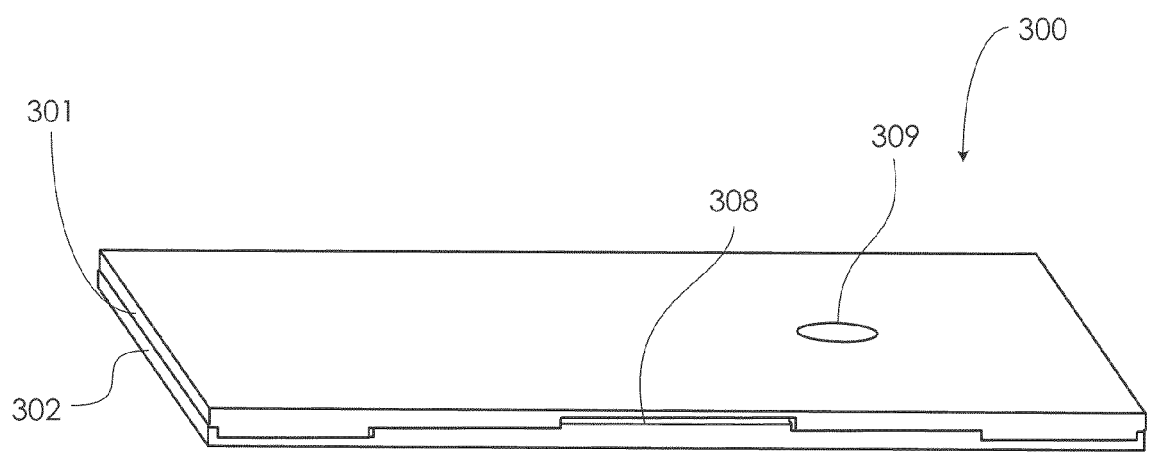
FIG. 11A shows an electrode structure formed from the first and second extruded bodies shown in FIG. 10.
Figure 11B:
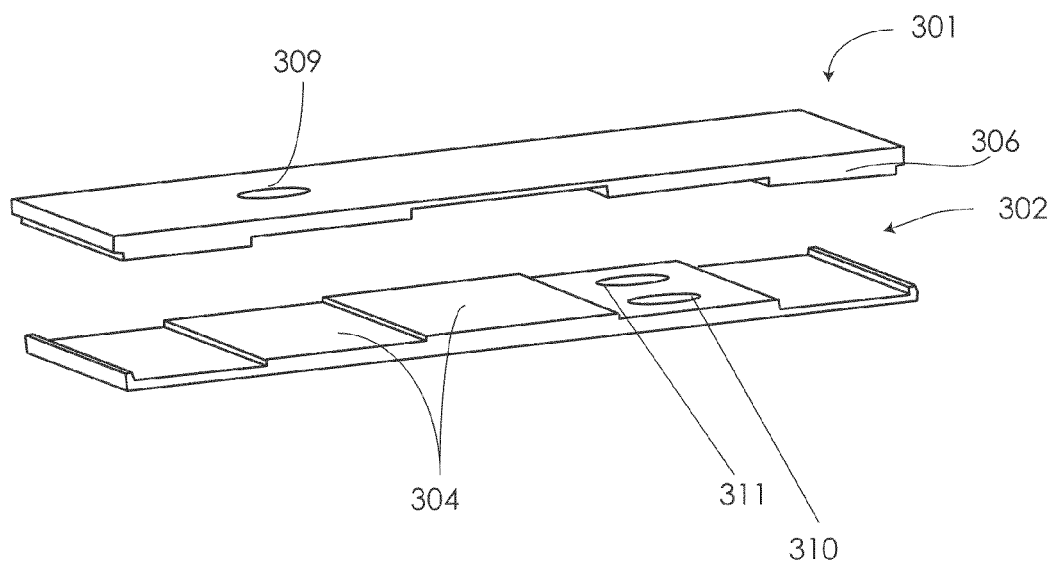
FIG. 11B shows a first extruded body positioned over a second extruded body prior to formation of the electrode structure in FIG. 11A.

One such embodiment is depicted in FIGS. 10, 11A and 11B. Electrode structure 300 is formed by snapedly engaging first extruded body 301 with second extruded body 302. FIG. 10 shows first extruded body 301 and second extruded body 302 prior to engagement. FIG. 11B shows first extruded body 301 positioned above second extruded body 302 prior to engagement to form electrode structure 300 as shown in Panel A. First extruded body 301 includes a first conductive material 303 coextruded with a first dielectric material 306. Second extruded body 302 includes a second conductive material 304 coextruded with a second dielectric material 307. Optionally, electrode structure 300 can include a third conductive material 305 as depicted in FIG. 10.

In one embodiment, as an alternative, or in addition to, snapedly engaging first extruded body 301 with second extruded body 302, the two extruded bodies can be attached to each other via an adhesive material, or other suitable interlocking features.

In some embodiments, the electrode structure is configured to detect and/or quantitate an analyte in a fluid sample. In such embodiments, first conductive material 303 can include a working electrode, second conductive material 304 can include a reference/counter electrode, and third conductive material 305 can include an indicator electrode when present. A gap 308 provides a reaction chamber into which a fluid sample can be introduced for quantitation and/or analysis. When introduced into the reaction chamber, the fluid sample comes into electrolytic contact with the working electrode, the reference/counter electrode and optionally the indicator electrode when present.

In some embodiments, as shown in FIG. 10, first extruded body 301 includes a hole 309. Hole 309 is positioned such that when first extruded body 301 and second extruded body 302 are engaged, hole 309 provides access to second conductive material 304, e.g., for connection to a power source and/or analyte meter. Similarly, second extruded body 302 can include holes 310 and 311, which provide access to first conductive material 303 and third conductive material 305 respectively.

While the embodiment depicted in FIGS. 10 and 11 has been described with respect to coextruded structures, it should be noted that in alternative embodiments the conductive materials can be deposited on first and second engageable bodies using standard deposition techniques known in the art.

Integrated Electrode Structures for In Vitro Use

Figure 12:
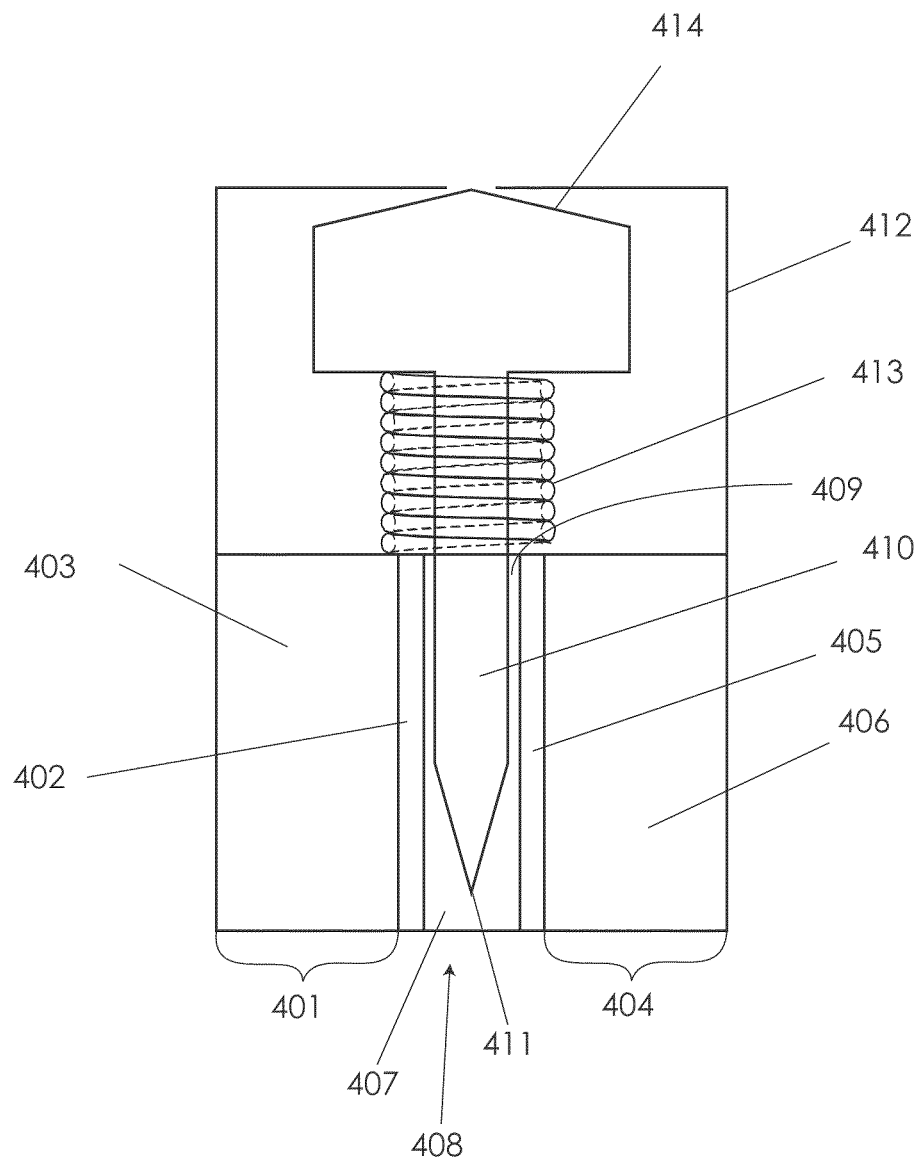
FIG. 12 shows an embodiment of an integrated lancet and electrode structure according to the present disclosure.
Figure 13:
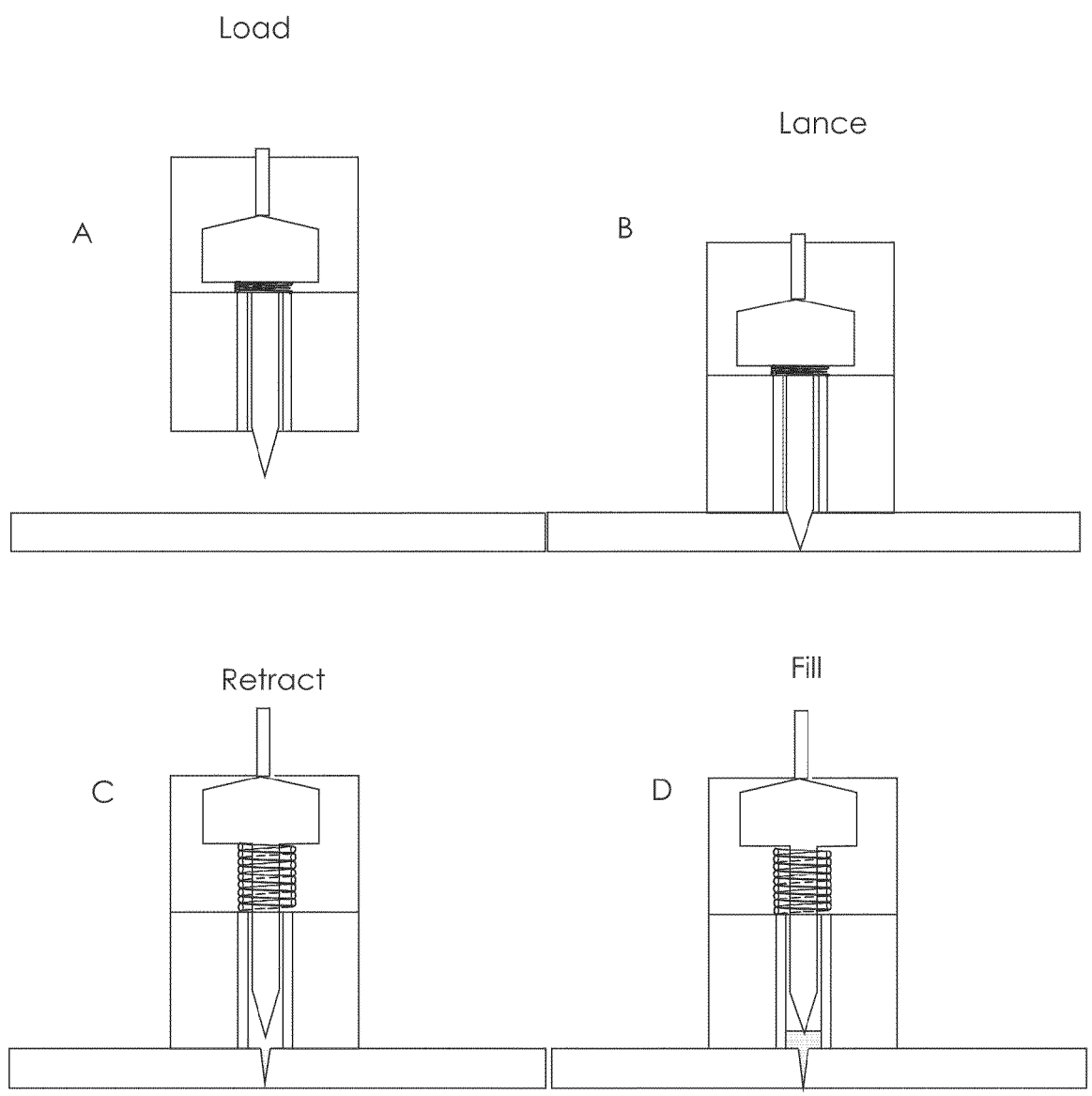
FIG. 13 illustrates a fluid sample extraction and collection process using the integrated lancet and electrode structure shown in FIG. 12.

The present disclosure provides integrated electrode structures for in vitro use. In one such embodiment, an integrated lancet and electrode structure is provided. The integrated structure is configured to lance the skin of a subject thereby providing fluid, e.g., blood, for analysis using the integrated electrode structure. In one embodiment, as shown in FIGS. 12-14, an integrated lancet and electrode structure 400 includes a first extruded body 401 which includes a first conductive material 402 coextruded with a first dielectric material 403. The first extruded body defines a first channel (not shown). The integrated lancet and electrode structure also includes a second extruded body 404 which includes a second conductive material 405 coextruded with a second dielectric material 406. The second extruded body defines a second channel (not shown). The integrated lancet and electrode structure 400 is configured such that the first conductive material 402 is electrically isolated from the second conductive material 405 and the first and second channels together define a lumen 407 having a first opening 408 and a second opening 409. The integrated lancet and electrode structure includes a lancet 410 slidably positioned within the lumen 407, wherein the lancet comprises a lancet tip 411. The integrated lancet and electrode structure 400 also includes a housing 412 and a spring 413 positioned in the housing 412 and engaged with the lancet 410, such that when the spring 413 is compressed (FIGS. 13, A and B), the lancet 410 extends through the lumen 407 to expose the lancet tip 411, and when the spring 413 is uncompressed (FIGS. 13, C and D), the lancet tip 411 is retracted to a position within the lumen 407. As shown in FIGS. 12-14, an optional lancet carrier 414 coupled to lancet 410 can be used to compress spring 413 during the lancing process. In some embodiments, the spring 413 is a molded component of the lancet carrier 414. It should be noted that use of a spring is exemplary as a variety of structures could be utilized to facilitate movement of the lancet 410 within the lumen 407. For example, mechanical means such as a piston, rotating arm, etc., could be coupled to the lancet 410 to facilitate movement of the lancet through the lumen 407. Such mechanical means could be a component of the electrode structure or alternatively a component of a separate device configured to engage the electrode structure.

It should be noted that an integrated lancet and electrode structure could also be configured by modifying one or more of the electrode structures depicted in FIGS. 2-7 (i.e., electrode structures where the first conductive material, second conductive material and dielectric material are coextruded) to include a lancet. In one embodiment, one or more of the electrode structures depicted in FIGS. 2-7 is modified to include a lancet, a spring (or other suitable structure) and a housing as described with respect to FIGS. 12-14.

Specific embodiments of an integrated lancet and electrode structure are now described with reference to FIGS. 15-28. The integrated lancet and electrode structure 400 includes a first extruded body 401 which includes a first conductive material 402 coextruded with a first dielectric material 403. The first extruded body defines a first channel 415. The integrated lancet and electrode structure also includes a second extruded body 404 which includes a second conductive material 405 coextruded with a second dielectric material 406. The second extruded body defines a second channel 416. The integrated lancet and electrode structure 400 is configured such that the first conductive material 402 is electrically isolated from the second conductive material 405 and the first and second channels together define a lumen 407 having a first opening 408 and a second opening 409. The integrated lancet and electrode structure includes a lancet 410 slidably positioned within the lumen 407, wherein the lancet 410 comprises a lancet tip 411. The lancet 410 is slidably positioned within the lumen 407, such that the lancet 410 is capable of being extended through the lumen 407 to expose the lancet 410 and retracted to a position within the lumen 407 such that the lancet 410 is not exposed.

The integrated lancet and electrode structure 400 can also include a housing 412 and an optional spring 413 positioned in the housing 412 and engaged with the lancet 410, such that when the spring 413 is compressed, the lancet 410 extends through the lumen 407 to expose the lancet tip 411, and when the spring 413 is uncompressed, the lancet tip 411 is retracted to a position within the lumen 407. Housing 412 includes an opening 429 through which lancet tip 411 is exposed during the lancing process. A lancet carrier 414 coupled to lancet 410 can be used to compress spring 413 during the lancing process. As indicated above, use of a spring is merely exemplary as a variety of structures could be utilized to facilitate movement of the lancet 410 within the lumen 407. For example, mechanical means such as a piston, rotating arm, etc., could be coupled to the lancet 410 to facilitate movement of the lancet through the lumen 407.

Figure 15:
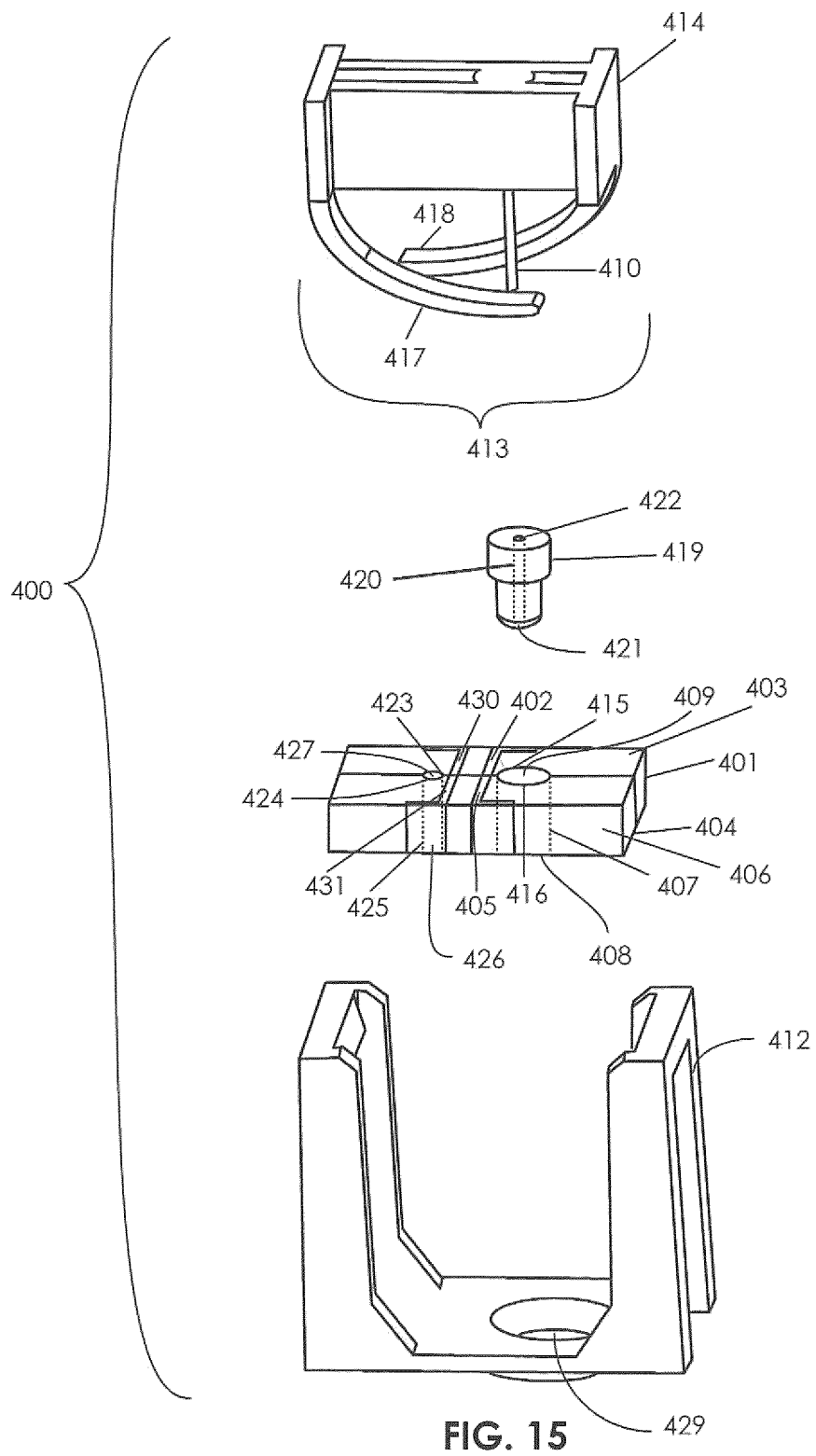
FIG. 15 shows an exploded view of a specific embodiment of an integrated lancet and electrode structure according to the present disclosure.

In the embodiment depicted in FIG. 15, the optional spring 413 is a molded component of the lancet carrier 414, i.e., the spring 413 and the lancet carrier 414 are molded from the same material to produce a unitary structure. Furthermore, in the embodiment depicted in FIG. 15, an optional configuration is shown in which spring 413 includes a first spring arm 417 and a second spring arm 418.

The embodiment depicted in FIG. 15 also includes an optional bung 419. Bung 419 is slidably positioned within the lumen 407. The bung 419 includes a lumen 420 with a first opening 421 and a second opening 422. The integrated lancet and electrode structure 400 is configured such that the lancet 410 is slidably positioned within the lumen 420. Bung 419 operates as a lancet guide and to keep the lancet 410 in a protected and/or sterile condition prior and/or subsequent to the lancing procedure. This can serve as a safety measure to prevent accidental contact with the lancet, e.g., by a user or health care provider. In exemplary embodiments, bung 419 comprises an elastomeric material.

Figure 16A:
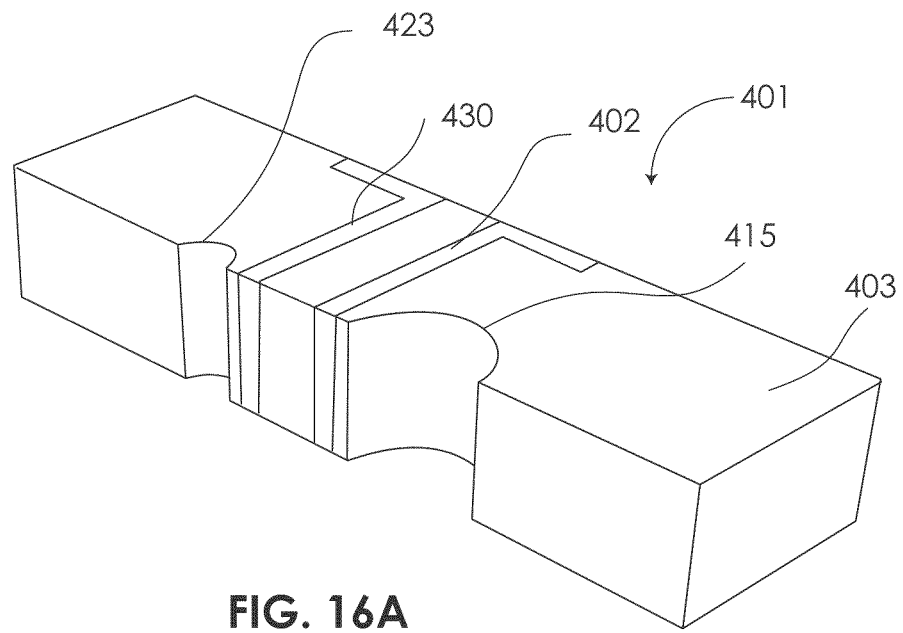
FIG. 16A and FIG. 16B show perspective views of a first extruded body (16A) and a first extruded body joined with a second extruded body (16B) in connection with the description of an integrated lancet and electrode structure according to the present disclosure.
Figure 16B:
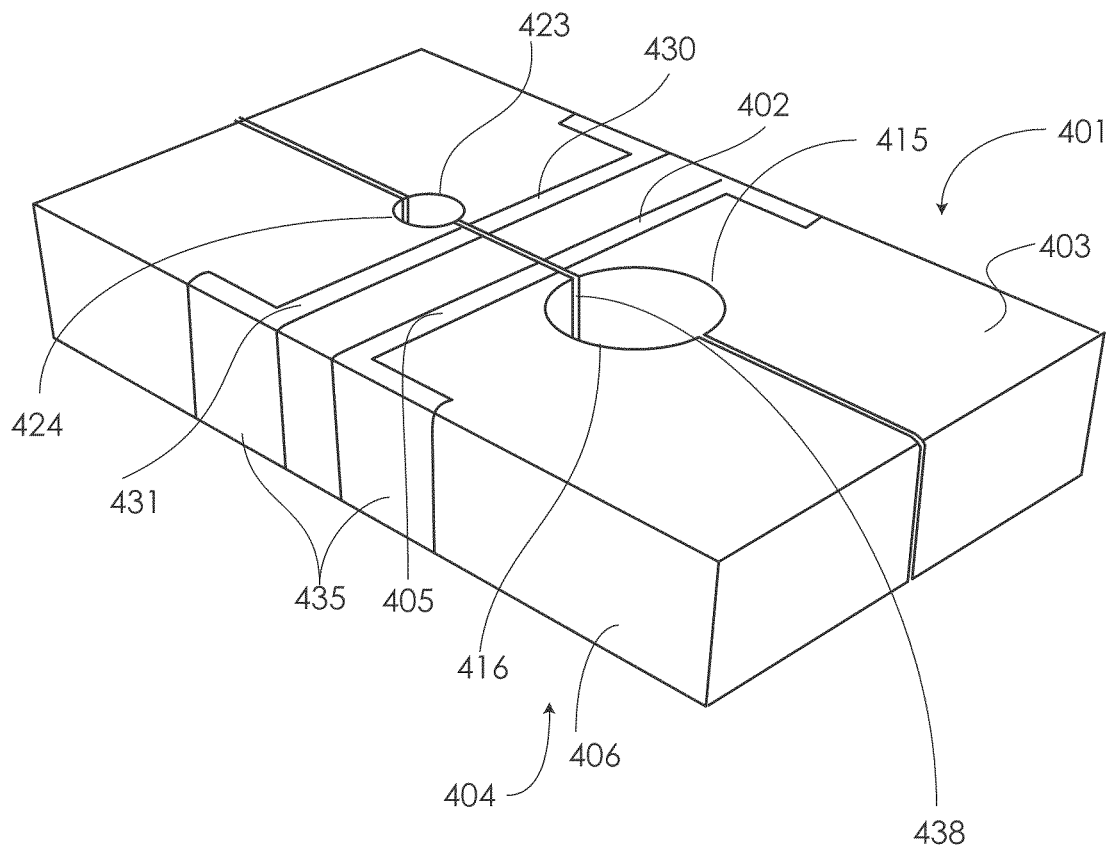
Figure 26:
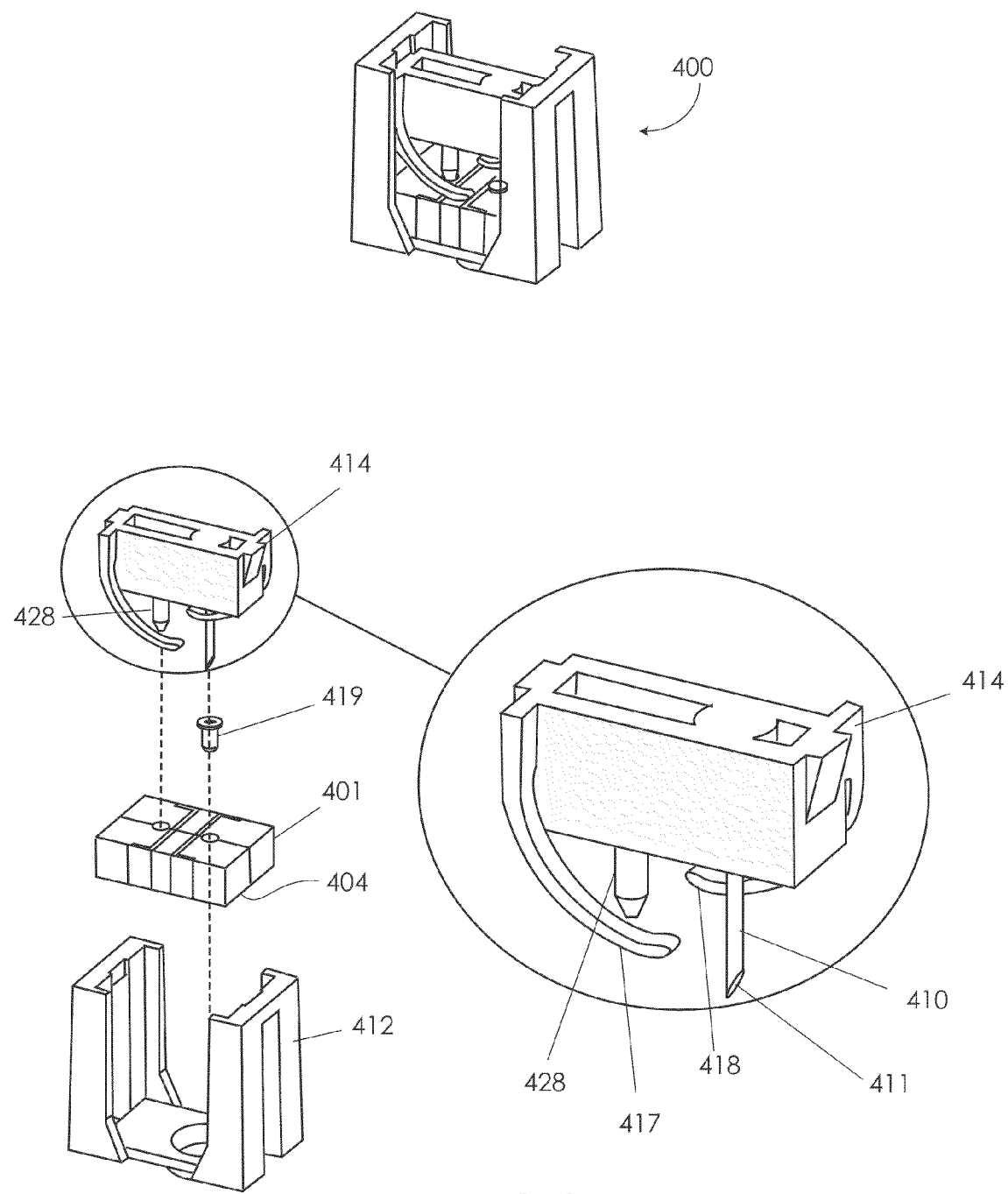
FIG. 26 shows an embodiment of an integrated lancet and electrode structure according to the present disclosure, wherein the integrated lancet and electrode structure includes a first lumen and a second lumen, the first lumen having approximately the same diameter as the second lumen.
Figure 27:
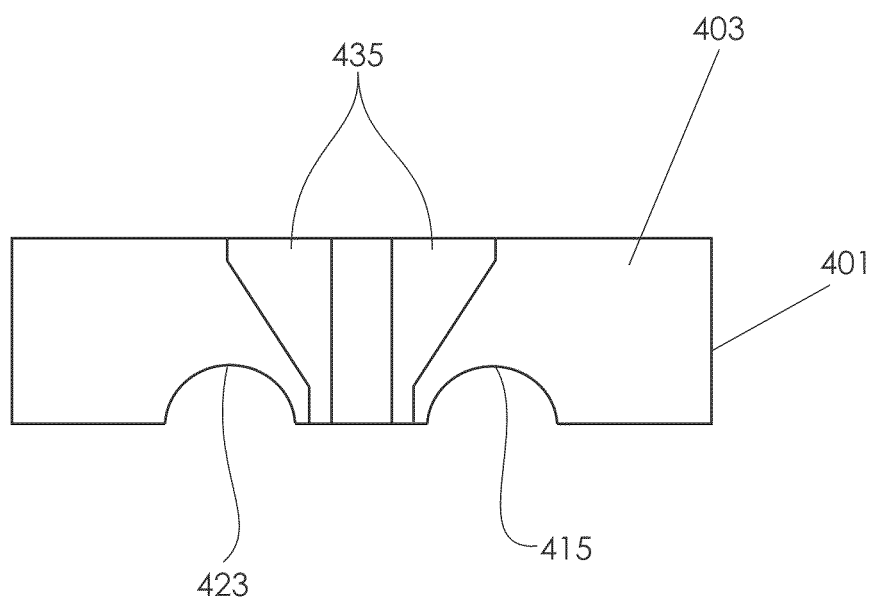
FIG. 27 shows a top view of one half of a conductive material configuration of an integrated lancet and electrode structure according to the present disclosure, wherein the integrated lancet and electrode structure includes a first lumen and a second lumen, the first lumen having approximately the same diameter as the second lumen.

The embodiment depicted in FIG. 15 includes optional modifications to the structure of the extruded bodies. Specifically, FIG. 15 shows an embodiment in which the first extruded body 401 and the second extruded body 404 include a third channel 423 and a fourth channel 424 respectively. The third channel 423 and the fourth channel 424 together define a lumen 425 having a first opening 426 and a second opening 427. This lumen 425 provides a path for optional guide 428 shown in FIG. 26. In some embodiments, lumen 425 may also facilitate the capillary movement of fluid sample from lumen 407 into a reaction chamber where the fluid sample comes into electrolytic contact with a conductive material configured as a working electrode. Lumen 425 can have the same or a different diameter as lumen 407. In some embodiments, as shown in FIGS. 16A and 16B, lumen 407 has a greater diameter than lumen 425. In other embodiments, as shown in FIGS. 26 and 27, lumen 407 has the same diameter as lumen 425.

FIGS. 16A and 16B shows first extruded body 401 individually (16A) and first extruded body 401 and second extruded body 404 positioned together (16B). With reference to FIGS. 16A and 16B, an optional embodiment is disclosed wherein first extruded body 401 includes a second conductive material 430 which is coextruded with conductive material 402 and dielectric material 403. Similarly, second extruded body 404 includes a second conductive material 431 which is coextruded with conductive material 405 and dielectric material 406. This configuration provides two extruded bodies, wherein each extruded body includes two conductive leads. Portions of these conductive leads can be modified as discussed further herein to include working, reference/counter, and indicator electrodes.

In one embodiment, dielectric material 403 and dielectric material 406 are the same and include a polymeric base resin, e.g., polyamide (nylon) polyimide, polyvinylchloride, Pbax®, PTFE, and the like. The polymeric base resin can be coextruded with carbon filled polymeric base resin, e.g., carbon filled Pbax® to provide conductive materials 402, 405, 430 and 431.

Figure 17A:
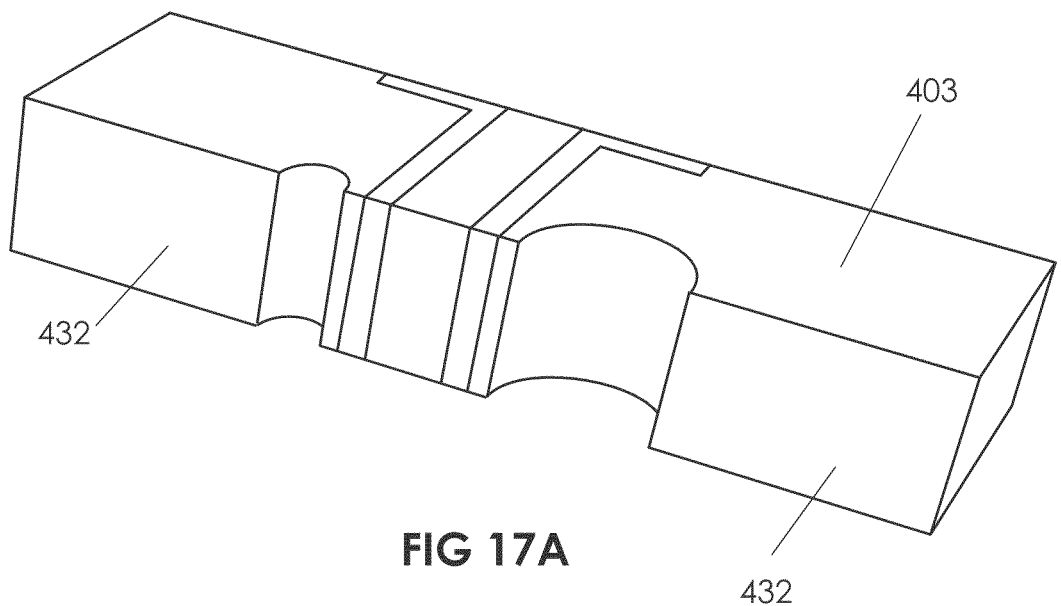
FIG. 17A shows the first extruded body of FIGS. 16A and 16B with adhesive material applied to facilitate the joining of the first extruded body with the second extruded body.
Figure 17B:
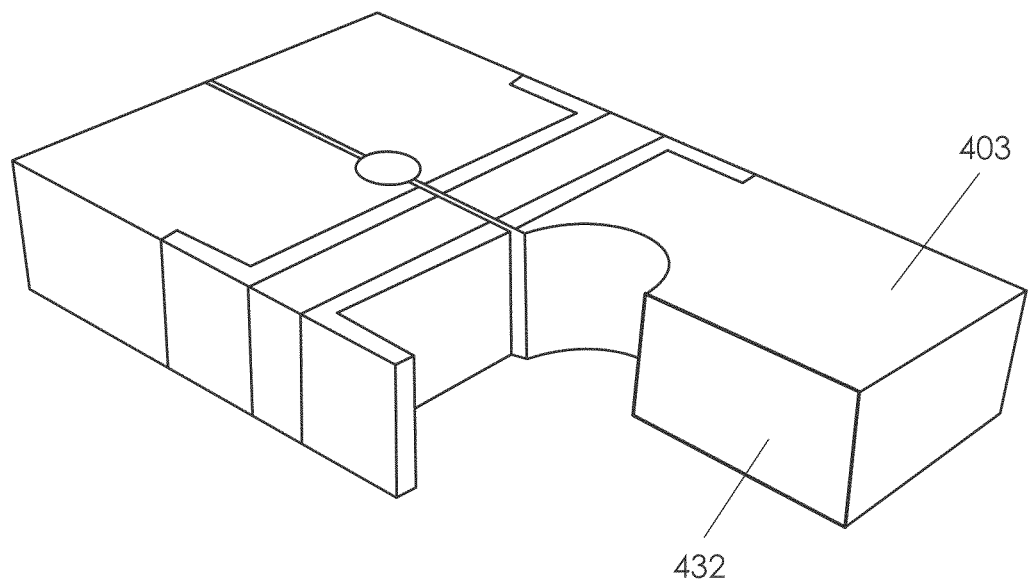
FIG. 17B shows the first extruded body and the second extruded body joined via the adhesive material; a portion of the second extruded body is not shown so that the location of the adhesive material can be seen.
Figure 22:
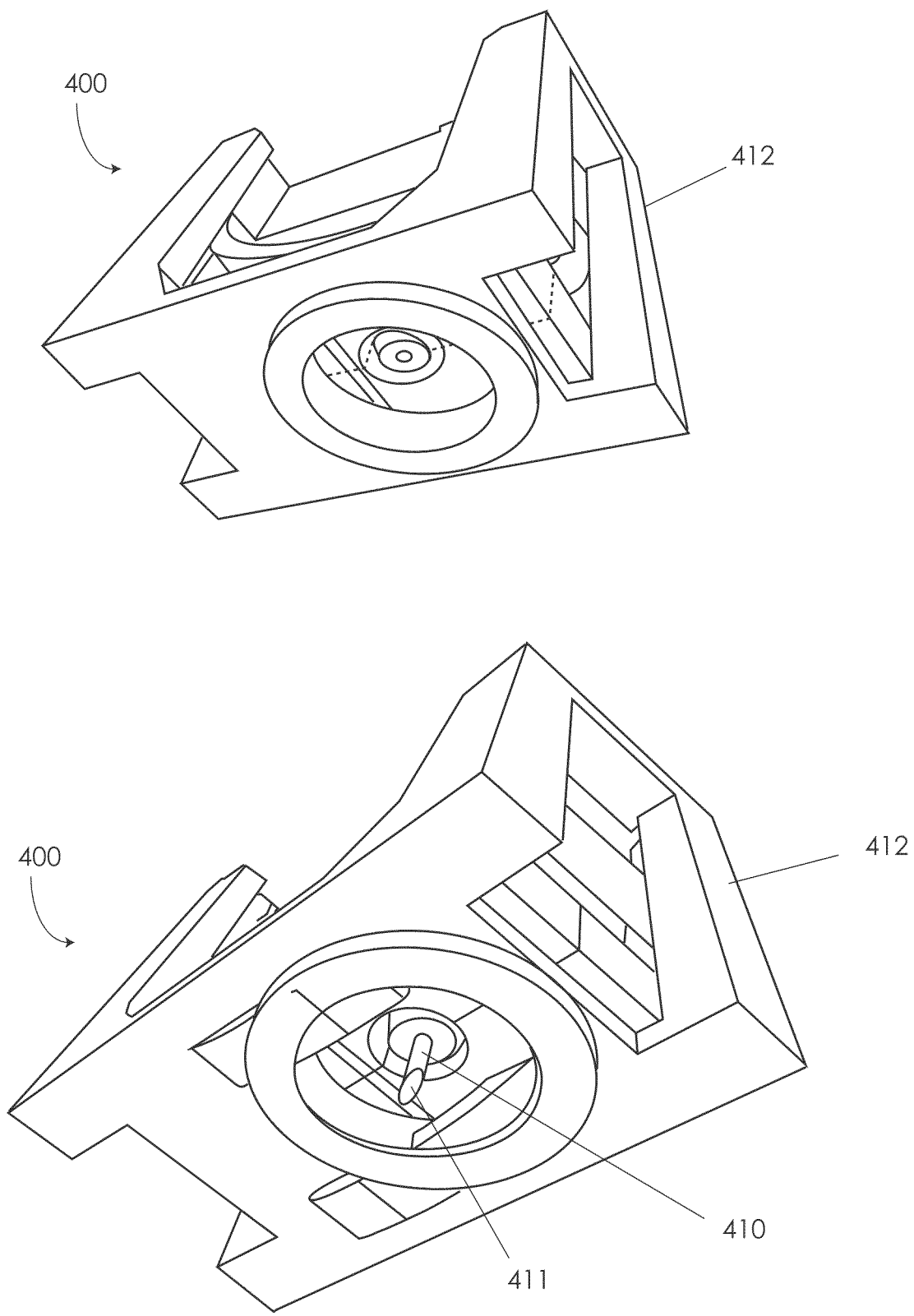
FIG. 22 shows two different bottom perspective views of an assembled version of the lancet and electrode structure shown in FIG. 15.

The first extruded body 401 and second extruded body 404 are joined to produce an electrode structure having lumens 407 and 425. As shown in FIGS. 17A and 17B, this can be accomplished via the use of an adhesive material 432, e.g., two-sided tape, glue or epoxy. In some embodiments, the thickness of the adhesive material 432 corresponds to the thickness of a reaction chamber 438 in which fluid sample comes into electrolytic contact with a working electrode. In exemplary embodiments, this thickness is small to promote rapid electrolysis of the analyte, as more of the sample will be in contact with the electrode surface for a given sample volume. Typically, the thickness of the reaction chamber is no more than about 0.2 mm. In some embodiments, the thickness of the reaction chamber is no more than about 0.1 mm, no more than about 0.05 mm, or less.

Figure 23:
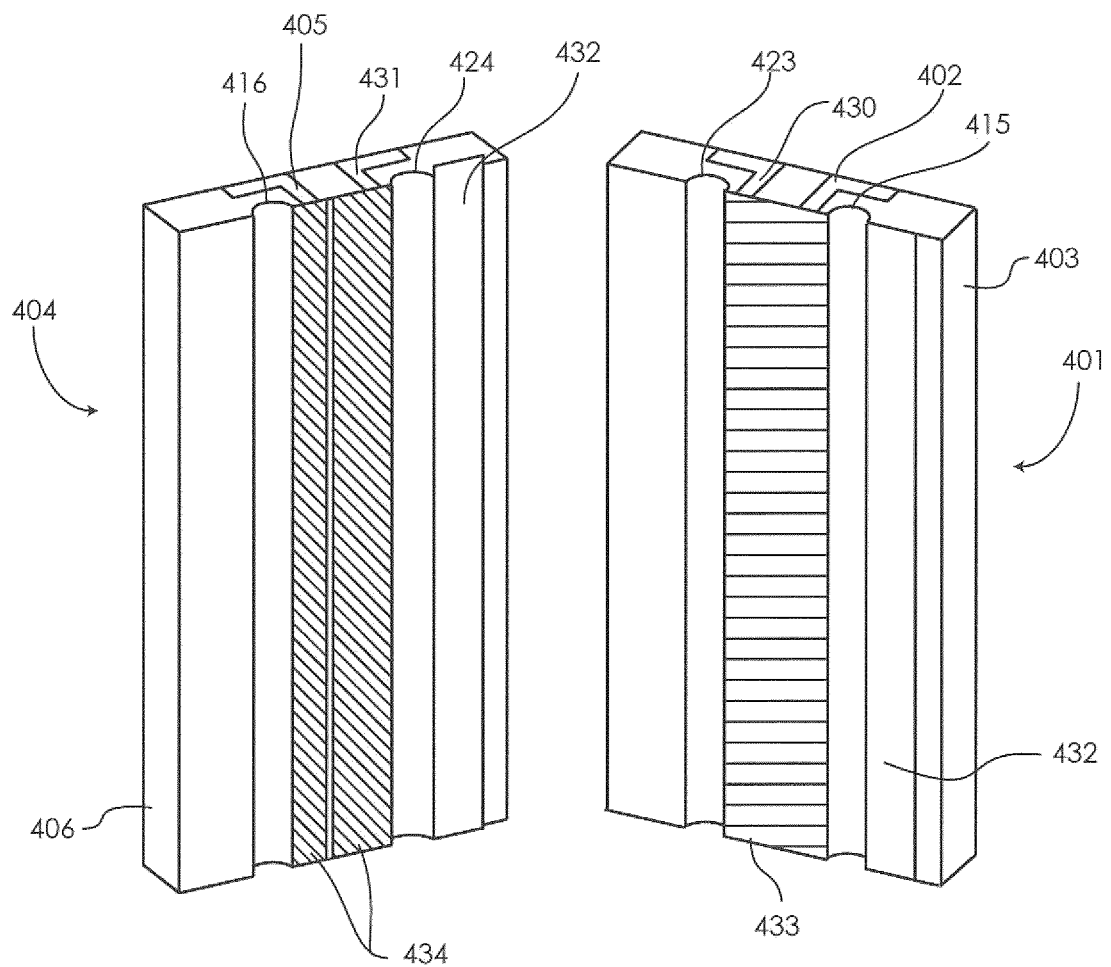
FIG. 23 shows first and second extruded bodies, wherein each of the first and second extruded bodies includes two conductive leads; a carbon based electrode ink is shown deposited over the conductive leads of the first extruded body to produce a working electrode; Ag/AgCl electrode ink is shown deposited over the conductive leads of the second extruded body to produce reference/counter and indicator electrodes.
Figure 24:
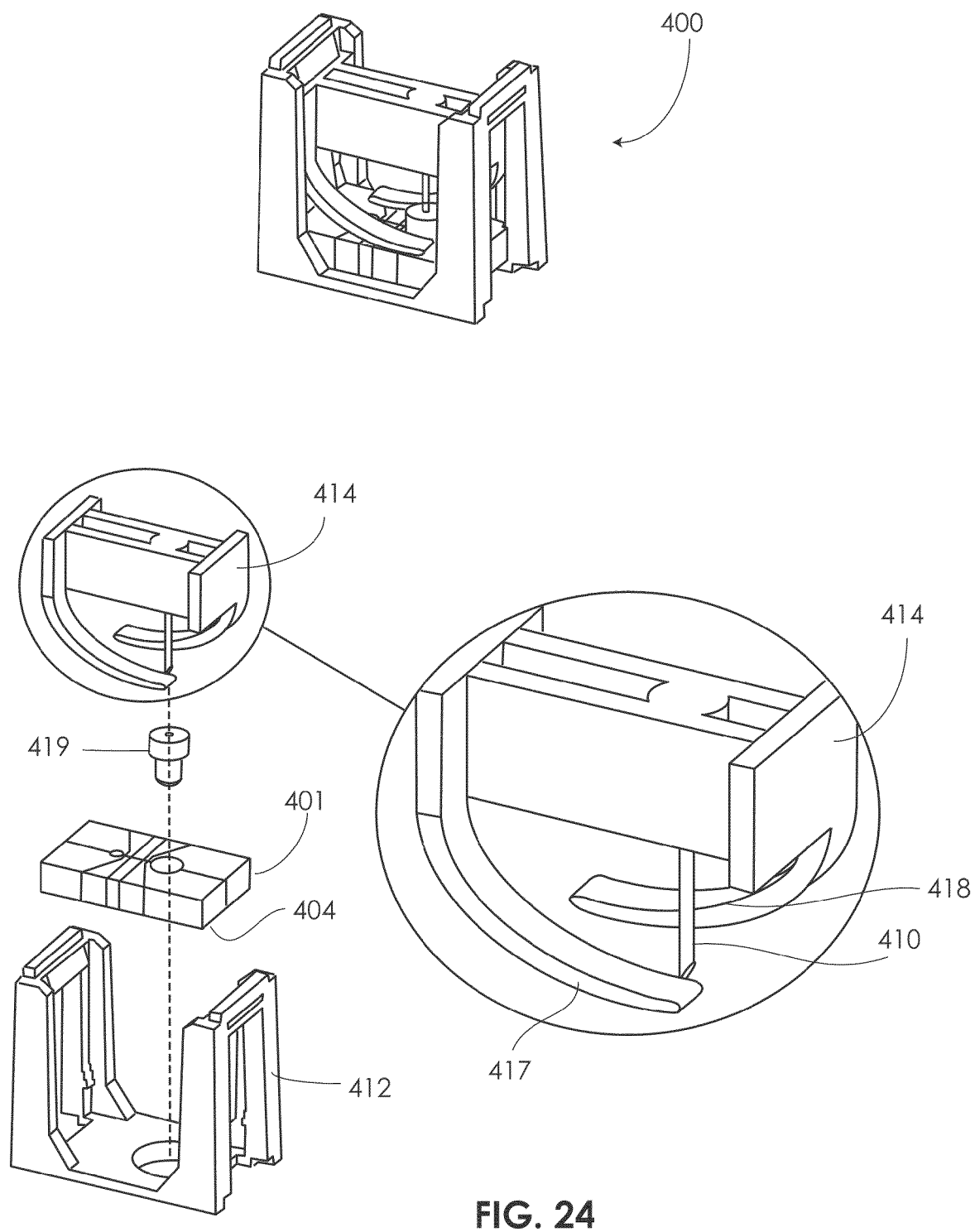
FIG. 24 shows an embodiment of an integrated lancet and electrode structure according to the present disclosure, wherein the integrated lancet and electrode structure includes a first lumen and a second lumen, the first lumen having a larger diameter than the second lumen.

As indicated above, in some embodiments, integrated lancet and electrode structure 400 includes two extruded bodies, wherein each of the two extruded bodies includes two conductive leads. In one embodiment, these conductive leads are modified to include working, reference/counter, and indicator electrodes as shown in FIG. 23. For example, a carbon based electrode ink 433 can be deposited over conductive materials 402 and 430 as shown in FIG. 23 to produce a working electrode. Similarly, Ag/AgCl electrode ink 434 can be deposited over conductive materials 405 and 431 to produce reference/counter and indicator electrodes respectively. As shown in FIG. 23, there is a non-conductive space between the Ag/AgCl conductive ink deposited over conductive material 405 and that deposited over conductive material 431. This allows for the formation of two different electrodes, e.g., a reference/counter electrode and an indicator electrode.

It should be noted that while first extruded body 401 has been described above as including conductive materials 402 and 430, such a configuration is only exemplary. In other embodiments, a single conductive material is included in first extruded body 401 and carbon based electrode ink is deposited over the single conductive material to produce the working electrode.

Figure 25:
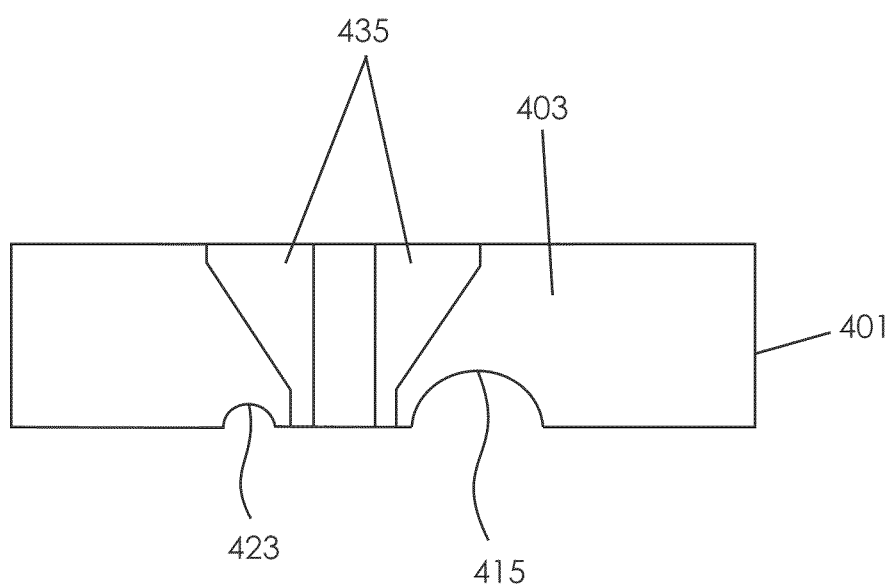
FIG. 25 shows a top view of one half of the conductive material configuration shown in FIG. 24.

With reference to, e.g., FIGS. 21 and 25, the integrated lancet and electrode structure 400 can include electrode contacts 435 which provide an electrical connection to a device of interest, e.g., an analyte meter. Electrode contacts 435 can be configured in a variety of ways depending on the desired connection geometry. In some embodiments, electrode contacts 435 are made up of the same materials used to extrude one or more of conductive materials 402, 430, 405 and 431. Contacts 435 can also be coextruded as a portion of one or more of conductive materials 402, 430, 405 and 431.

In some embodiments, as shown in FIG. 26, lancet carrier 414 includes a guide element 428, which is configured to slidably engage lumen 425. The guide element 428 may serve to stabilize engagement of lancet carrier 414 with the electrode structure.

Figure 28:
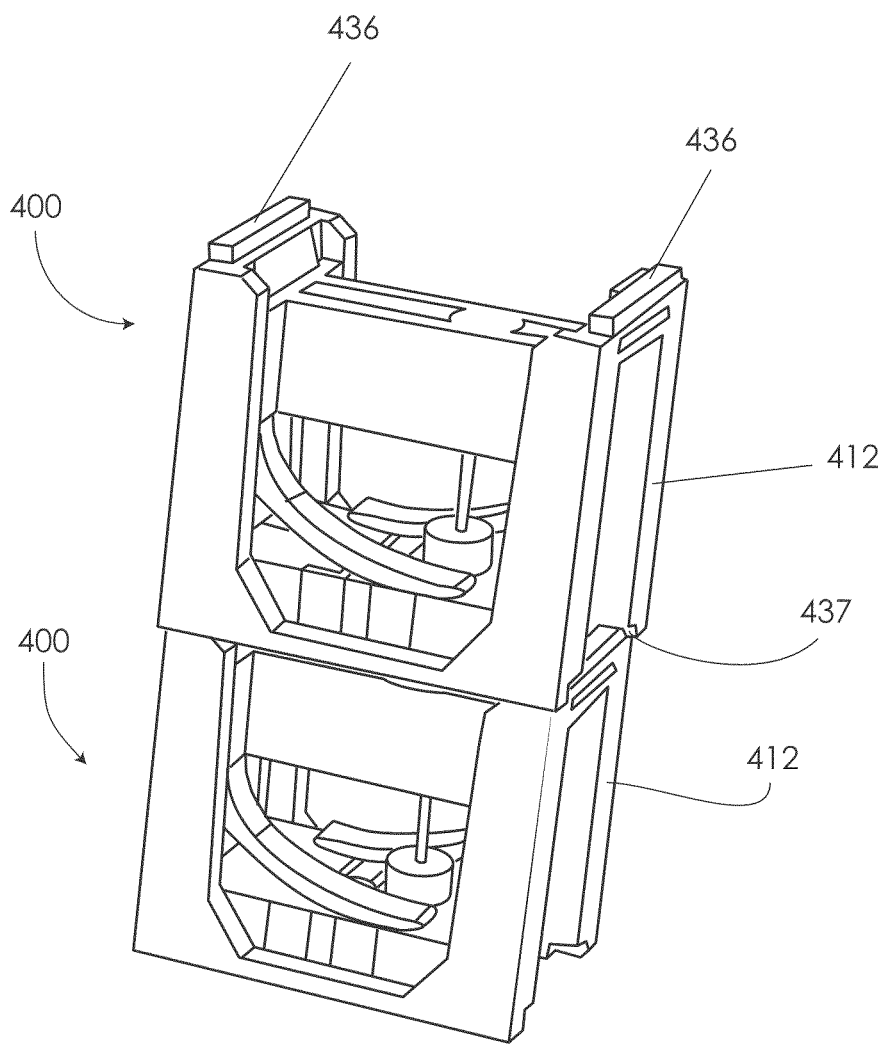
FIG. 28 shows two integrated lancet and electrode structures stackably engaged with each other.

It may be of interest to configure an integrated lancet and electrode structure 400 such that multiple integrated lancet and electrode structure can be stackably engaged. In such an embodiment, as depicted in FIG. 28, housing 412 can include one or more protrusions 436 positioned at the top end of a first integrated lancet and electrode structure 400. The one or more protrusions 436 can be configured to engage one or more indentations or notches 437 positioned at the bottom end of a second integrated lancet and electrode structure 400. These stackable integrated lancet and electrode structures may be useful for integration with an analyte meter configured to hold multiple integrated electrode structures. Stackable integrated lancet and electrode structures may also facilitate the packaging and/or sterilization of multiple integrated lancet and electrode structures.

Extruded Electrode Structures for In Vivo Use

The present disclosure provides extruded electrode structures, which, in some embodiments, are configured for in vivo use. As used herein, "in vivo use" refers to a use wherein the electrode structure is at least partially positioned within the body of a subject. For example, use of an electrode structure to detect and/or quantify the level of an analyte in the blood and/or interstitial fluid of a subject, wherein the electrode structure is at least partially implanted through the skin of the subject, is considered an in vivo use. Accordingly, the present disclosure includes analyte monitoring electrode structures (i.e., sensors) at least a portion of which are positionable beneath the skin surface of the user for the in vivo detection, of an analyte, including glucose, lactate, and the like, in a body fluid. Embodiments include wholly implantable analyte sensors and analyte sensors in which only a portion of the electrode structure is positioned under the skin surface and a portion of the electrode structure resides above the skin surface, e.g., for contact to a sensor control unit (which may include a transmitter), a receiver/display unit, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors of the present disclosure may be configured for monitoring the level of the analyte over a time period which may range from seconds, minutes, hours, days, weeks, to months, or longer.

Many suitable configurations are available for the in vivo electrode structures described herein including, but not limited to, electrode structures having solid or substantially solid configurations, and electrode structures having hollow configurations. Exemplary embodiments of these configurations are described in greater detail below with reference to the figures.

Solid Configurations

Figure 29:
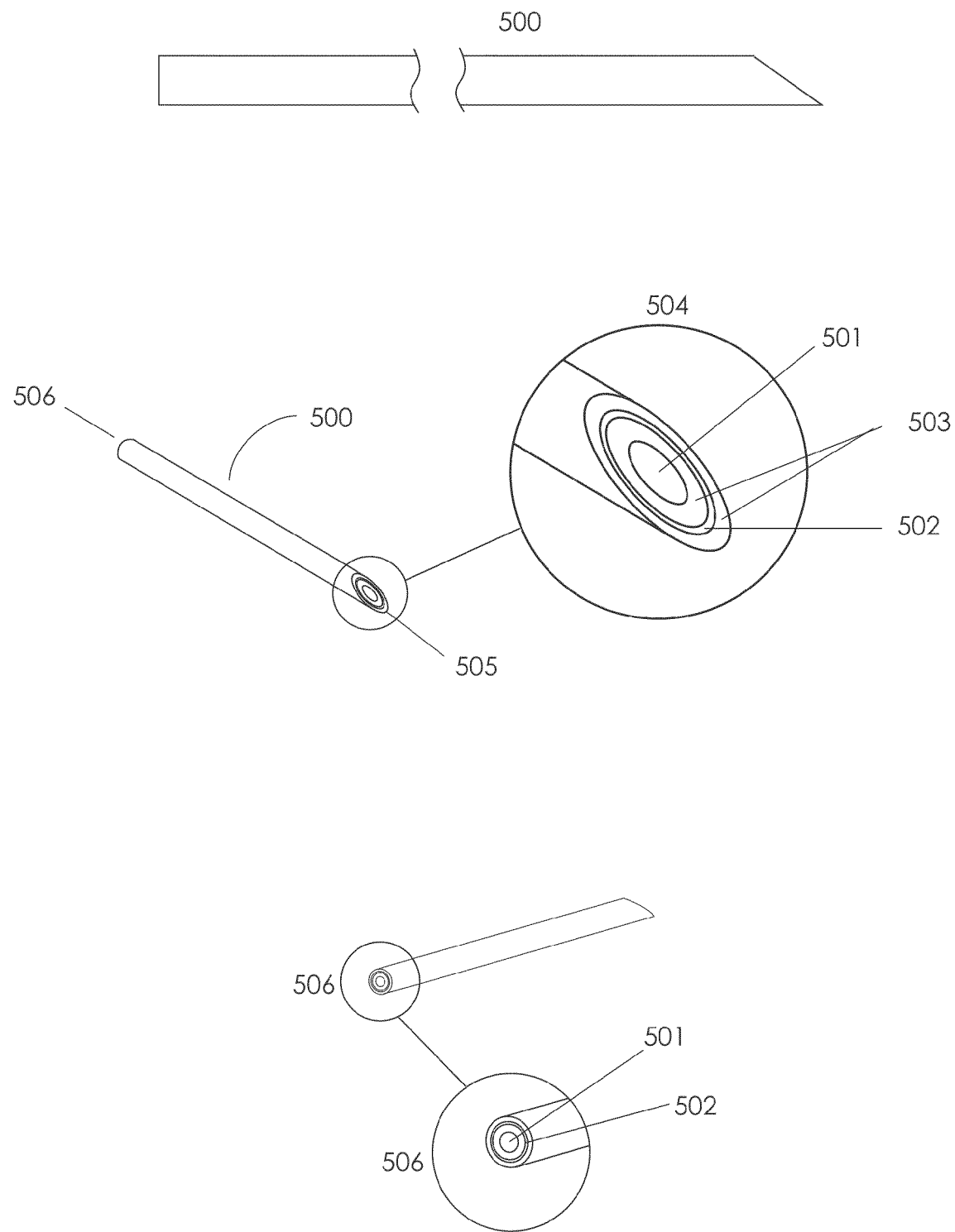
FIG. 29 shows a solid, cylindrical electrode structure in which a first conductive material and a second conductive material are coextruded with a dielectric material so as to provide a cylindrical electrode structure having a conductive center core and a conductive ring in a coaxial configuration.

Solid or substantially solid electrode configurations suitable for in vivo use can be prepared in a variety of configurations. For example, solid or substantially solid electrode structures suitable, for example, for in vivo use and having a cylindrical configuration are provided in FIGS. 29, 30, and 31. FIG. 29 shows a solid, cylindrical electrode structure 500 in which first conductive material 501 and second conductive material 502 are coextruded with a dielectric material 503 so as to provide a cylindrical electrode structure 500 having a conductive center core and a conductive ring in a coaxial configuration. The conductive ring and the conductive center core are electrically isolated by the dielectric material 503. In the embodiment shown in FIG. 29, first conductive material 501 is extruded as the conductive center core and second conductive material 502 is extruded as the coaxial conductive ring. It should be noted that this configuration can be reversed with first conductive material 501 being extruded as the coaxial conductive ring and second conductive material 502 being extruded as the conductive center core.

Figure 30:
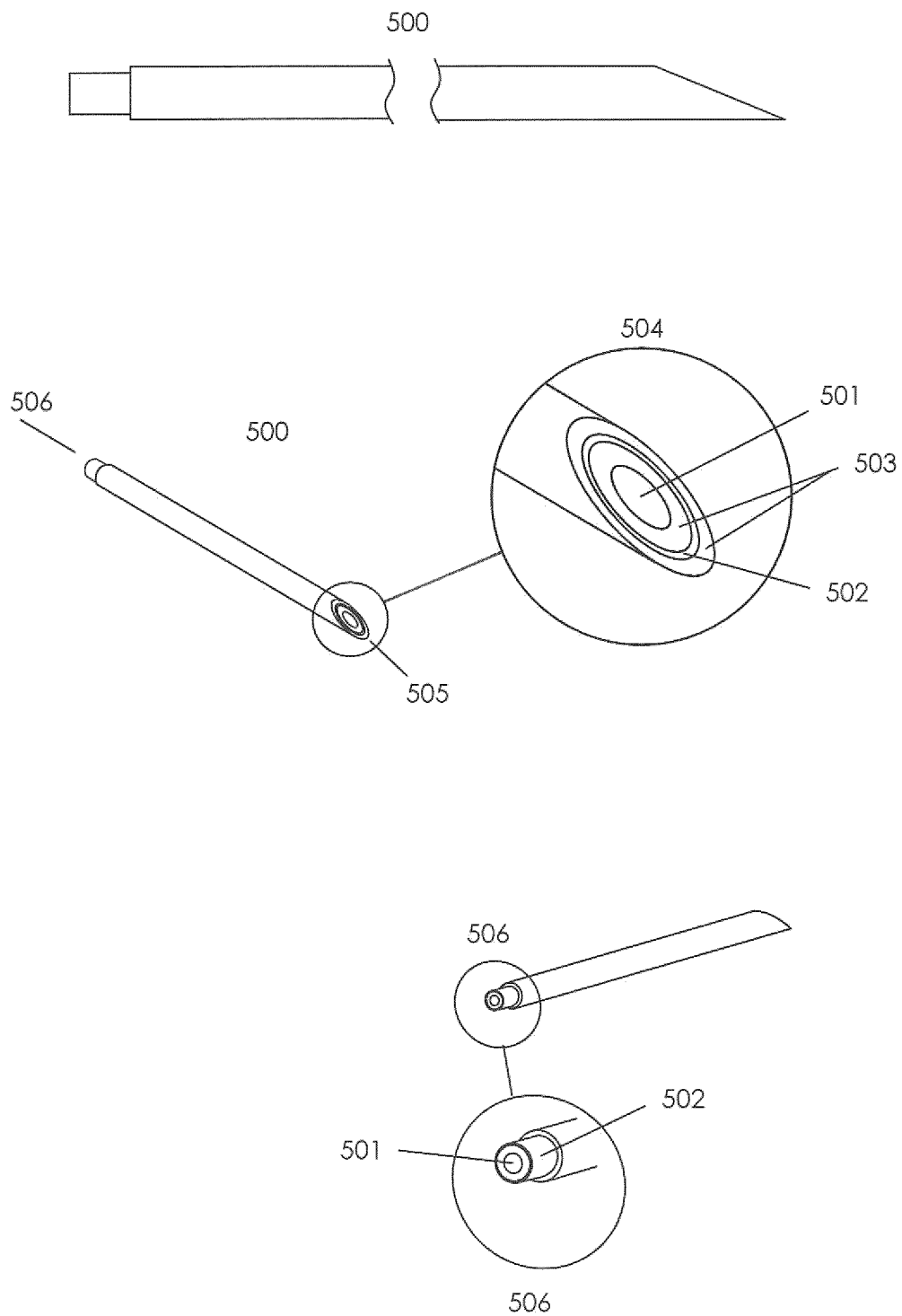
FIG. 30 shows a solid, cylindrical electrode structure as shown in FIG. 29 wherein the second end of the electrode structure is modified via stripping of the dielectric material to provide greater surface area exposure for the coaxial conductive ring relative to the embodiment shown in FIG. 29.

In addition, as shown in FIGS. 29-31, the dielectric material 503 can be coextruded so as to cover the outside surface of the conductive ring as a protection and/or insulation measure. While FIGS. 29-31 illustrate cylindrical configurations including first and second conductive materials, it should be noted that these configurations can be readily modified to include third, fourth or $n^{th}$ conductive materials. In the context of the solid cylindrical configurations, these additional conductive materials can be included as additional coaxial conductive rings separated from each other by one or more dielectric materials.

In the embodiment shown in FIGS. 29 and 30, the electrode structure 500 includes an optional angled end or tip 504 at first end 505. As used herein, the terms "angled end" and "angled tip" are used interchangeably to refer to an end having an angle of less than 90° relative to the horizontal plane of the electrode structure (for example, the plane defined by the length of the electrode structure 500). Inclusion of such an angled end serves to increase the exposed surface areas of the conductive materials relative to an end having a 90° angle relative to the horizontal plane of the electrode structure. In addition, depending on the properties of the conductive materials and/or the dielectric, e.g., depending on the rigidity, the angled end can serve as a sharp to facilitate insertion of the electrode structure through the skin layer of a subject and/or into, e.g., the tissue of the subject.

In one embodiment, as an alternative, or in addition to, inclusion of the angled end or tip at first end 505, the various conductive layers can be exposed by stripping away portions of the dielectric material from first end 505 to create electrode surfaces in various geometries that can be exposed to the surrounding environment.

In some embodiments, second end 506 of the electrode structure 500 includes a flat face having an at least substantially 900 angle relative to the horizontal plane of the electrode structure as shown in FIG. 29. In such embodiments, the conductive core and the coaxial conductive ring are exposed at second end 506 as shown in FIG. 29.

In other embodiments, second end 506 is modified to provide greater exposure for the conductive core and/or the coaxial conductive ring. This can be accomplished, for example, by stripping the dielectric layers 503 covering the conductive core and/or the coaxial conductive ring from second end 506 as shown in FIG. 30. Such modification configures each of the conductive materials for connection, e.g., to a connector or cable, which can simplify the manufacturing process and eliminate a potential need for keyed connectors commonly used for connection with some analyte sensors.

In some embodiments, the electrode structure 500 is configured for use as an analyte sensor. In these embodiments, the conductive core can be configured as a reference/counter electrode while the coaxial conductive ring is configured as a working electrode. Alternatively, the conductive core can be configured as a working electrode while the coaxial conductive ring is configured as a reference/counter electrode.

FIG. 31 shows a specific embodiment, in which first conductive material 501 is extruded as the conductive center core and second conductive material 502 is extruded as the coaxial conductive ring. First end 505 of electrode structure 500 is configured as a sensing end of the analyte sensor. In the method outlined in FIG. 31, dielectric material 503 is removed from first end 505 to expose an area of the coaxial conductive ring (A). The electrode structure 500 is contacted with a solution containing suitable sensing chemistry 507 (B). The sensing chemistry solution is allowed to dry (C). Excess sensing chemistry is then removed from end 505 (D) to expose the conductive center core and the coaxial conductive ring (E). A membrane 508 is applied to end 505 (F) which covers the previously applied sensing chemistry as well as the exposed region of the conductive center core and the coaxial conductive ring (G and H). Application of the sensing chemistry to conductive material 502, which has been extruded as the coaxial conductive ring, configures conductive material 502 as a working electrode. Conductive material 501, which has not had the sensing chemistry applied, is available for use as a reference/counter electrode. In some embodiments, it may be desirable to add an additional conductive material, e.g. Ag/AgCl, to conductive material 501 to configure it as a reference/counter electrode. This could be done, for example, prior to the addition of sensing chemistry 507 and/or prior to the addition of membrane 508.

A variety of additional configurations for the solid or substantially solid electrode structures described herein are possible. These include, e.g., flexible or rigid configurations and configurations in the form of strings, strips or rods. In addition, while FIGS. 29-31 depict electrode structures having conductive materials in coaxial configurations, it should be noted that non-coaxial embodiments are also possible. For example, in one such embodiment, the electrode structure can include a first conductive material in the form of a conductive stripe or zone and a second conductive material in the form of a conductive stripe or zone, wherein the first conductive material and the second conductive material are not positioned coaxially with respect to each other. In such an embodiment, the conductive materials are coextruded to provide an electrode structure have the first conductive material and the second conductive material electrically isolated by the dielectric material.

Hollow Configurations

Extruded, hollow electrode structures have wide applicability for in vivo use and can be prepared in a variety of configurations. For example, FIGS. 32-39 show exemplary hollow electrode structures having a tubular configuration. These tubular electrode structures 600 include a first conductive material 601, a second conductive material 602, and a dielectric material 603. The first conductive material 601, the second conductive material 602, and the dielectric material 603 are coextruded to provide an electrode structure 600 having the first conductive material 601 and the second conductive material 602 electrically isolated by the dielectric material 603. The electrode structure 600 includes a lumen 604, wherein the lumen includes a first opening 605, a second opening 606, and a lumen wall 607. In the embodiments shown in FIGS. 32-39, the dielectric material 603 defines the lumen wall 607, and the first and second conductive materials (601 and 602) are provided, e.g., embedded or positioned, in the dielectric material 603.

In some embodiments, e.g., as shown in FIGS. 32-39, the lumen extends the length of the electrode structure with the first opening 605 positioned at one end and the second opening 606 positioned at the opposite end. In some embodiments, hollow electrode structures according to the present disclosure include multiple lumens, e.g., 2, 3, 4, or more lumens. The electrode structures can be configured such that these lumens extend the length of the electrode structures thereby providing multiple passageways through the electrode structures. The lumens described in connection with the embodiments discussed herein are not limited to a particular cross-sectional size or shape as a variety of different cross-sectional sizes and shapes may be utilized.

In one embodiment, hollow electrode structures having a tubular configuration as described above have an outer diameter of about 0.60 mm to about 0.90 mm and a lumen diameter of about 0.40 mm to about 0.50 mm. For example, in some embodiments, a hollow electrode structure according to the present disclosure has an outer diameter of about 0.60 mm, 0.65 mm, 0.70 mm, 0.75 mm, 0.80 mm, 0.85 mm, or 0.90 mm. In some embodiments, a hollow electrode structure according to the present disclosure has a lumen diameter of about 0.40 mm, 0.45 mm, or 0.50 mm.

The length of the extruded, hollow electrode structures can vary significantly depending on the desired application. In some embodiments, an extruded, hollow electrode structure according to the present disclosure has a length of about 10 mm to about 20 mm, e.g., 15 mm.

The extruded electrode structures of the present disclosure can include one or more optional orientations features which allow a user and/or subject to differentiate between the first and second conductive materials. For example, the embodiment shown in FIG. 32 includes an optional orientation feature in the form of a planar face 608 which extends the length of the electrode structure. The positioning of the planar face allows a user and/or subject to determine the identity of the first and second conductive materials based on their position relative to the planar face 608.

As shown, for example, in FIGS. 32-39 electrode structures according to the present disclosure can be configured such that a first conductive material 601 and a second conductive material 602 extend the length of extruded electrode structure 600. Such a configuration allows for the communication of electrical signals from one end of the electrode structure, e.g. a proximal end, to another end of the electrode structure, e.g. a distal end. Where the electrode structure is configured as an analyte sensor, such a configuration allows a sensor signal to be generated at one end of the electrode structure, e.g., an end inserted into the body of a subject, and communicated to another end of the electrode structure, e.g., an end positioned outside the body of the subject for connection to another device.

Differentiation between conductive materials, e.g., first and second conductive materials, can also be facilitated by configuring the conductive materials to include different colors which allow for visual differentiation between the conductive materials. This may be accomplished, for example, by including one or more dyes along with the conductive materials during the extrusion process.

In some embodiments, the extruded electrode structure 600 is configured as an analyte sensor, wherein the first conductive material 601 includes a working electrode and the second conductive material 602 includes a reference/counter electrode. In such embodiments, the working electrode includes a sensing layer disposed on, in or proximate thereto.

Figure 33:
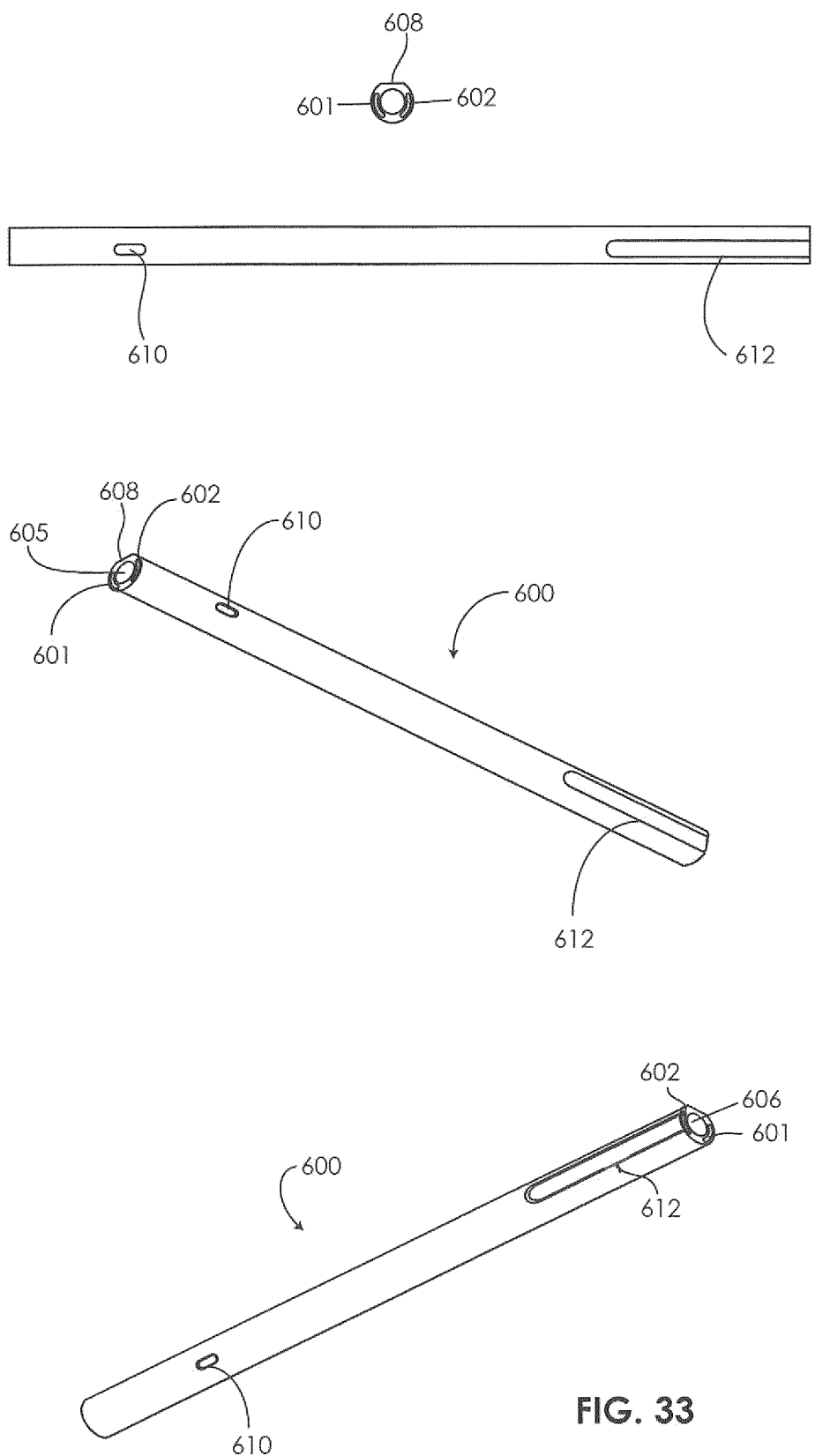
FIG. 33 shows an exemplary hollow electrode structure having a tubular configuration as shown in FIG. 32, wherein the hollow electrode structure has cutouts which exposes a working electrode and a reference/counter electrode.
Figure 34:
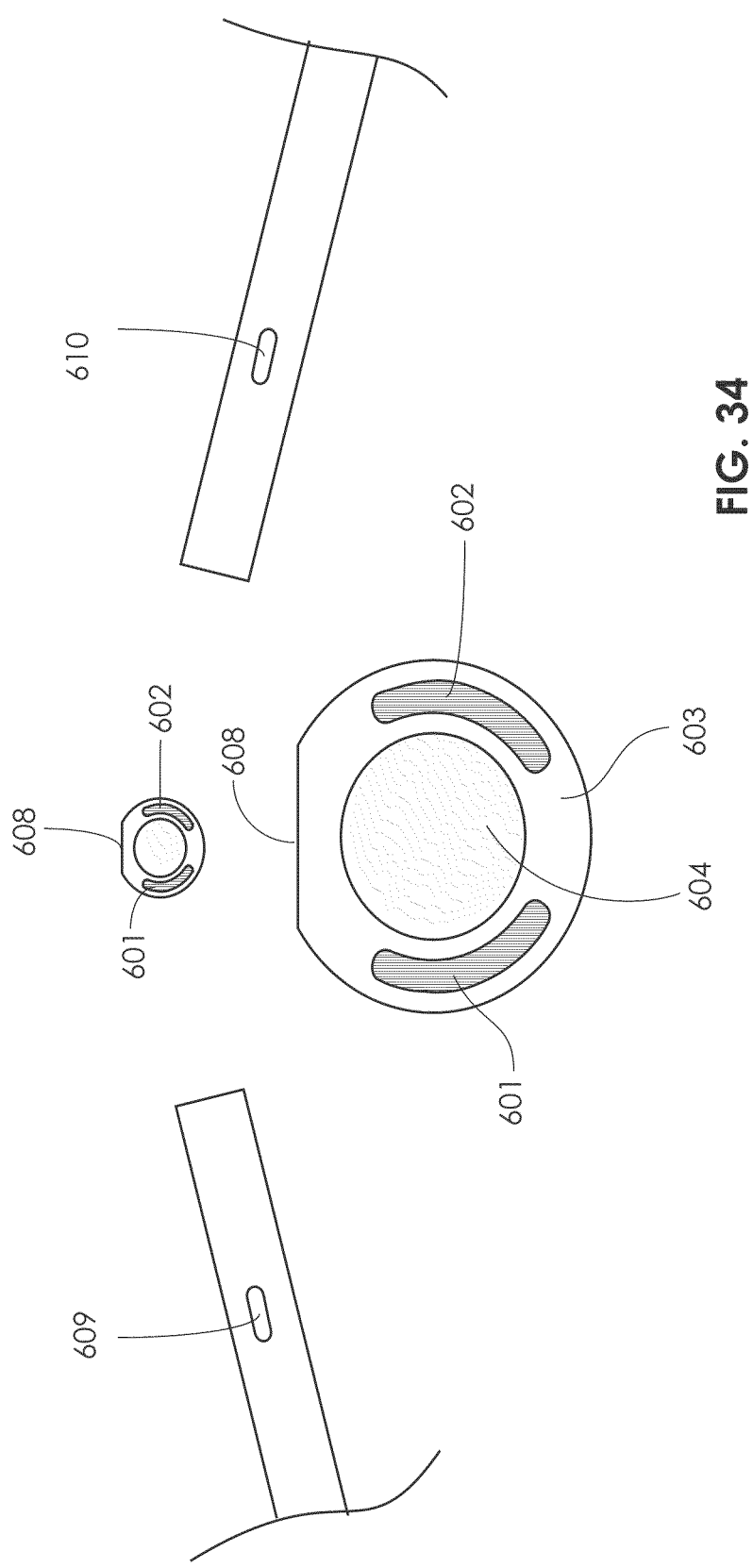
FIG. 34 shows a cross-section view of the sensor end of the hollow electrode structure shown in FIG. 33.

As shown in FIGS. 33 and 34, the electrode structure 600 can include a first cutout 609 in the dielectric material 603 which exposes the working electrode and a second cutout 610 in the dielectric material 603 which exposes the reference/counter electrode. These cutouts provide regions for contact between a sample, e.g., an analyte containing fluid, and the working and reference/counter electrodes. In addition, the cutout 609 which exposes the working electrode provides a location for the deposition of the sensing layer of the working electrode.

Figure 35:
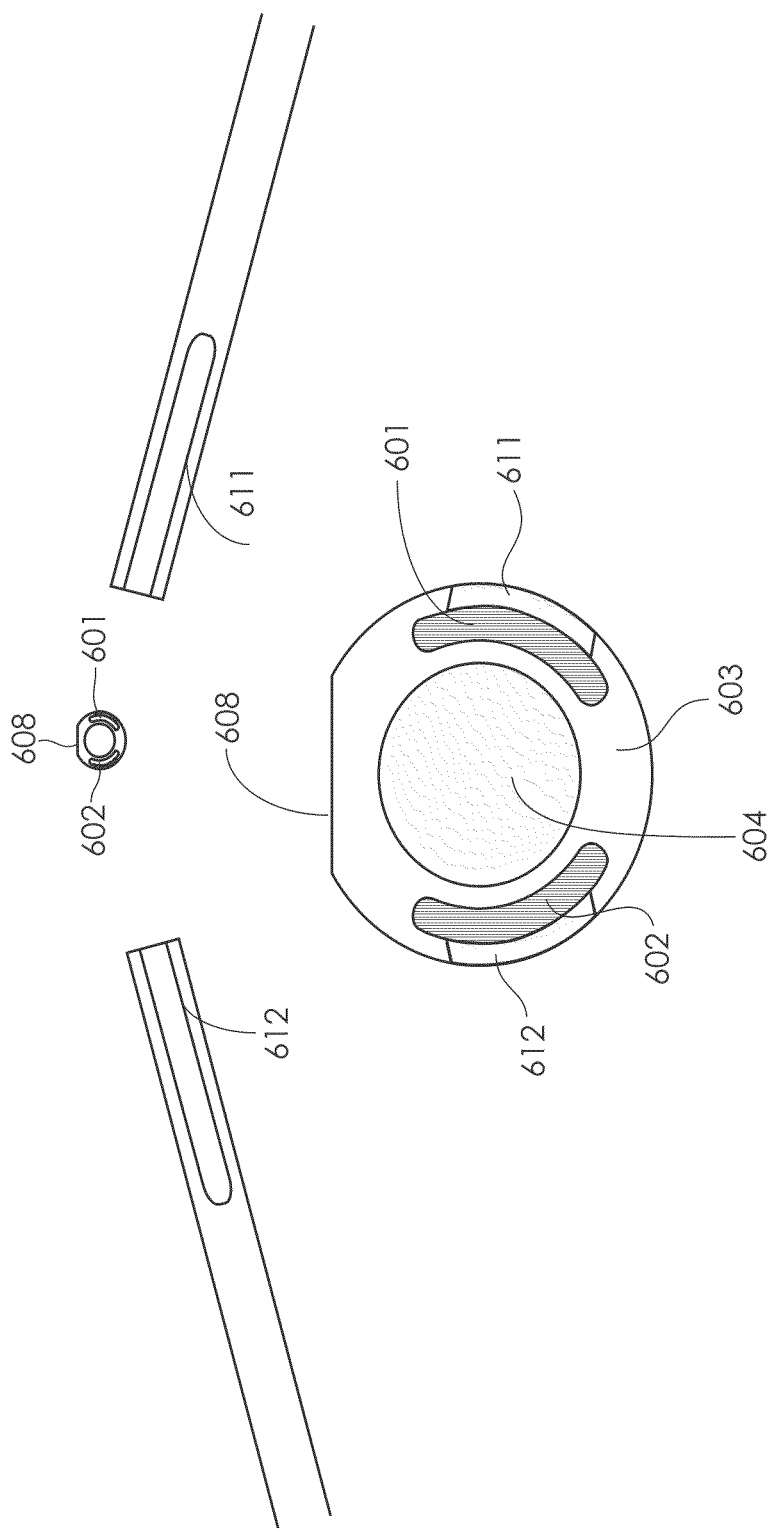
FIG. 35 shows a cross-sectional view of the connection end of the hollow electrode structure shown in FIG. 33.

In some embodiments, as shown for example in FIGS. 33 and 35, electrode structure 600 includes a third cutout portion 611 and a fourth cutout portion 612. The third cutout portion 611 exposes a portion of the first conductive material 601 and the fourth cutout portion 612 exposes a portion of the second conductive material 602. Cutout portions 611 and 612 provide exposed portions of their respective conductive materials which can facilitate electrical connection of the electrode structure to a device, e.g., electronics for processing signals from the analyte sensor such as, an analog interface including a potentiostat, a data processing component (such as one or more microprocessors), and/or a power source.

It should be noted that the dimensions of the cutout portions of the electrode structure can vary based on the particular application and/or connection intended for the electrode structure. The cutouts can be produced, for example, by cutting, drilling, laser etching, skiving, or any other suitable method. In some embodiments, the process used to produce the cutouts (or alternatively an independent process) can be used to manipulate the topography of one or more of the conductive materials exposed by the cutouts, for example, to manipulate the surface energy and/or increase the surface area of one or more of the conductive materials. For example, one or more hills, valleys, rows, etc., could be created in the surface of the conductive material exposed by a cutout to increase the surface area of the conductive material exposed by the cutout. Where the electrode structure is configured as an analyte sensor, such a manipulation of the electrode structure may serve to increase the sensitivity of the analyte sensor.

In some embodiments, where the electrode structure is configured as an analyte sensor, a membrane, e.g., a flux limiting membrane, may be disposed over the sensing layer. In such embodiments, a cutout exposing the sensing layer may be modified to facilitate retention of the membrane. For example, the cutout in the in the dielectric material can create one or more groves or channels in the dielectric material which facilitate retention of the membrane. In some embodiments, the membrane may be deposited as a liquid, e.g., in a dropwise manner, which subsequently solidifies forming the membrane. In such embodiments, the membrane may be effectively "locked" in position once it fills and then solidifies in the one or more grooves or channels created in the dielectric material.

Figure 39:
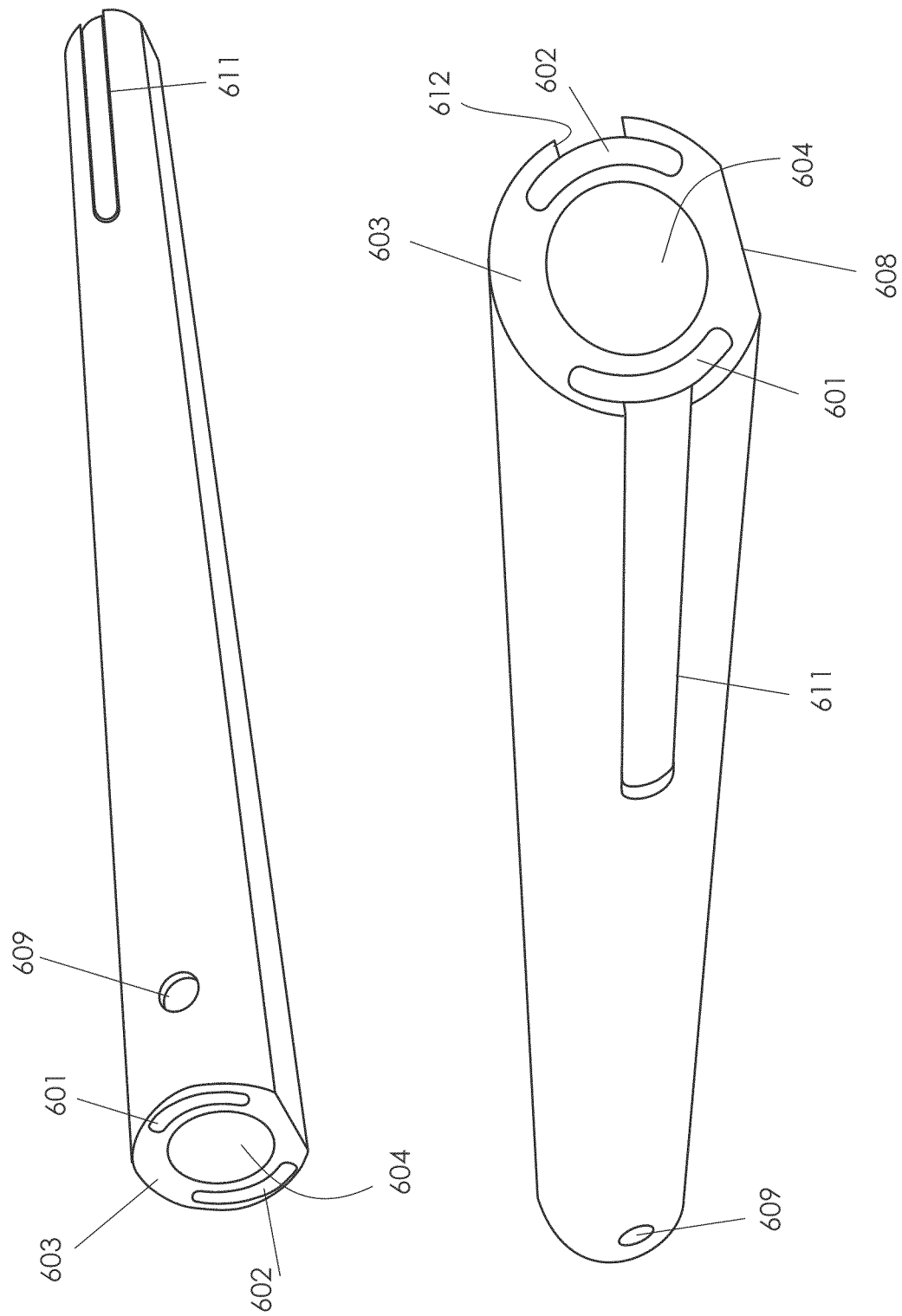
FIG. 39 shows two different views of an exemplary hollow electrode structure having a tubular configuration in accordance with the present disclosure.

The locations of the cutout portions of the electrode structure can also be varied depending on the particular application. For example, cutouts exposing the working and/or reference/counter electrode can be positioned in varying proximity to the proximal or distal end of electrode structure. In some embodiments, as shown in FIGS. 33 and 39, cutouts 609 and 610 are positioned at a proximal end of electrode structure 600, while cutouts 611 and 612 are positioned at a distal end of electrode structure 600.

For some embodiments, where the electrode structure is configured as an analyte sensor, use of a semi-permeable dielectric material may eliminate the need to expose a working electrode and/or a reference/counter electrode through the use of cutouts or other modification of the dielectric material as described above.

The hollow electrode structures described herein have a variety of potential uses and can be configured for use in any application where it would be desirable to utilize a tube having conductive capabilities, for example, as a medication delivery cannula/analyte sensor or as electrically conductive medical tubing. Where an electrode structure according to the present disclosure is configured as a medication delivery cannula/analyte sensor it may be desirable to position cutouts or other means of exposing the working and/or reference/counter electrode at a distance from a dispensing end of the medication delivery cannula. This allows for analyte detection at a distance from the point of medication delivery which may be beneficial where delivery of the medication causes a change in analyte concentration in the immediate vicinity. Accordingly, in some embodiments, cutouts or other means of exposing the working and/or reference/counter electrode are positioned at least 5 mm to at least 15 mm, e.g., 6 mm to 14 mm, 7 mm to 13 mm, 8 mm to 12 mm, 9 mm to 11 mm or 10 mm, from the site of medication delivery.

Insertion of Hollow Electrode Configurations

With reference to FIGS. 32-39, 40, 44, and 45, insertion of an electrode structure 600 into the body of a subject can be accomplished via use of an insertion needle 613 which extends through lumen 604 of electrode structure 600. After insertion is completed, insertion needle 613 can be withdrawn, leaving at least a portion of the electrode structure 600 implanted or positioned under the skin surface in the body of the subject.

Figure 45:
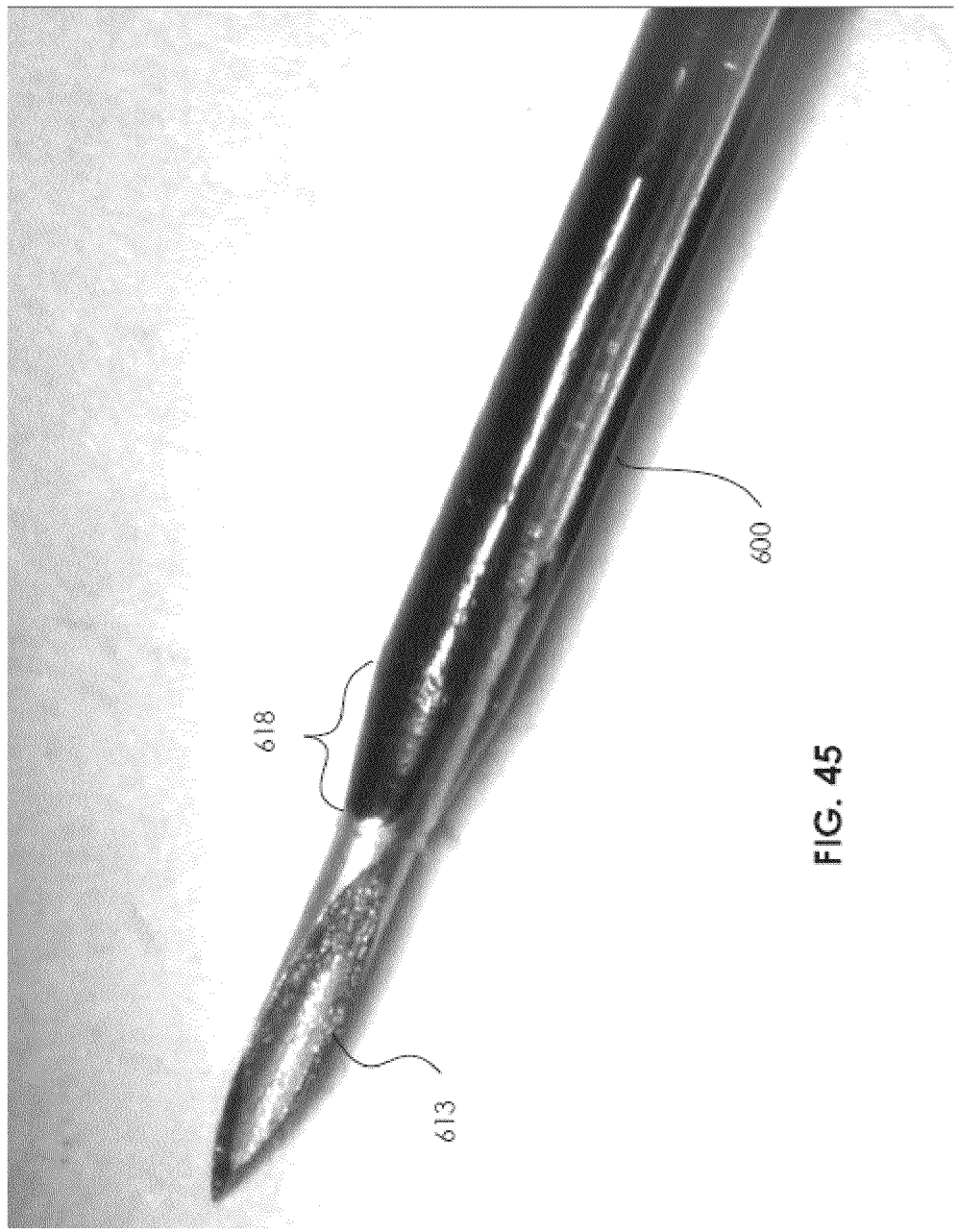
FIG. 45 shows a photograph of a hollow electrode structure and an insertion needle in accordance with the present disclosure; wherein the hollow electrode structure includes a tapered tip.
Figure 46:
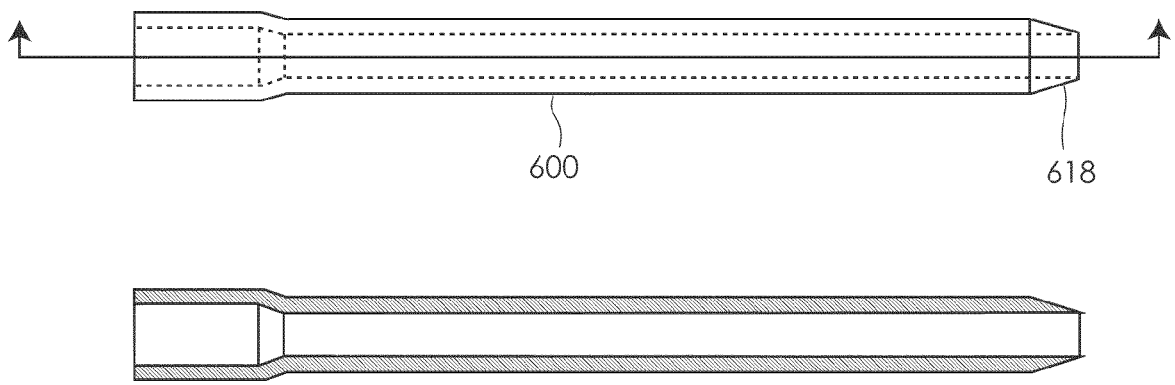
FIG. 46 shows two views of an exemplary external configuration for a hollow electrode structure having a tapered tip and a flared end.

In some embodiments, electrode structure 600 includes a tapered tip 618, as shown in FIGS. 45 and 46, which can facilitate insertion, e.g., via an insertion needle 613 as described above.

Connection Geometry for Hollow Electrode Configurations

Figure 40:
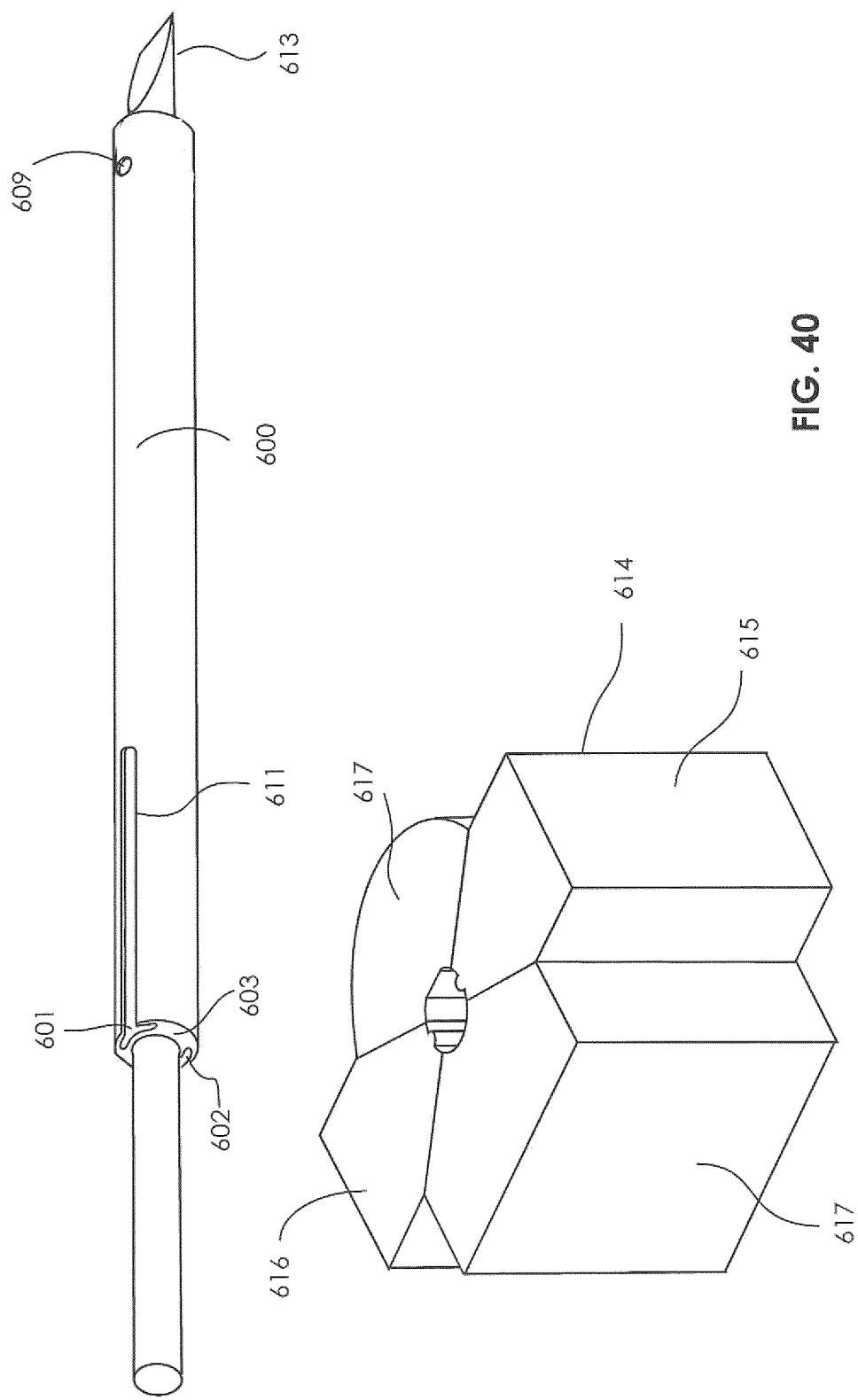
FIG. 40 shows an exemplary hollow electrode structure having a tubular configuration and an insertion needle.
Figure 41:
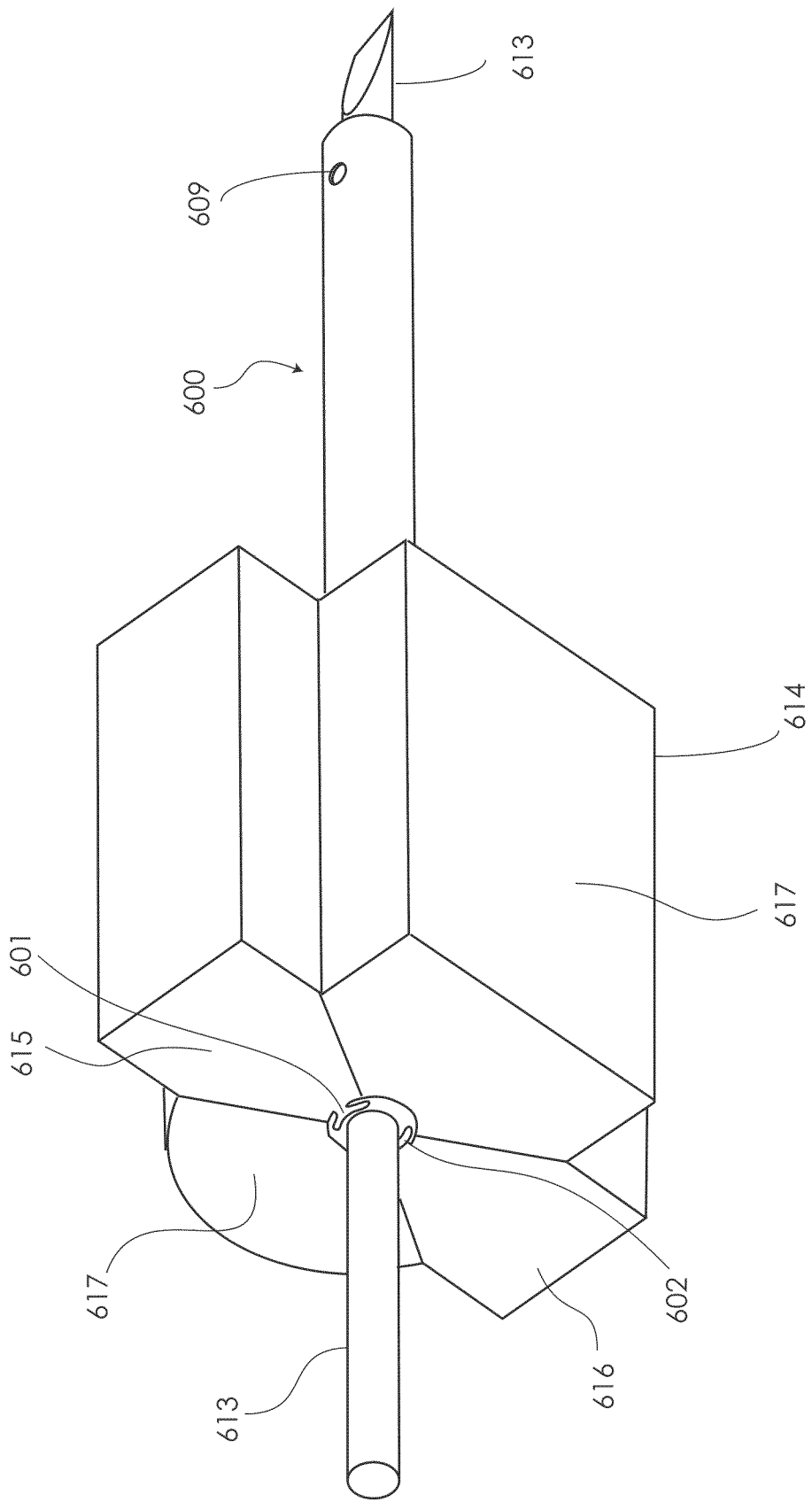
FIG. 41 shows the exemplary hollow electrode structure of FIG. 40 engaged with the connector of FIG. 40.
Figure 42:
FIG. 42 shows a photograph of a hollow electrode structure having a tubular configuration in accordance with the present disclosure.
Figure 43:
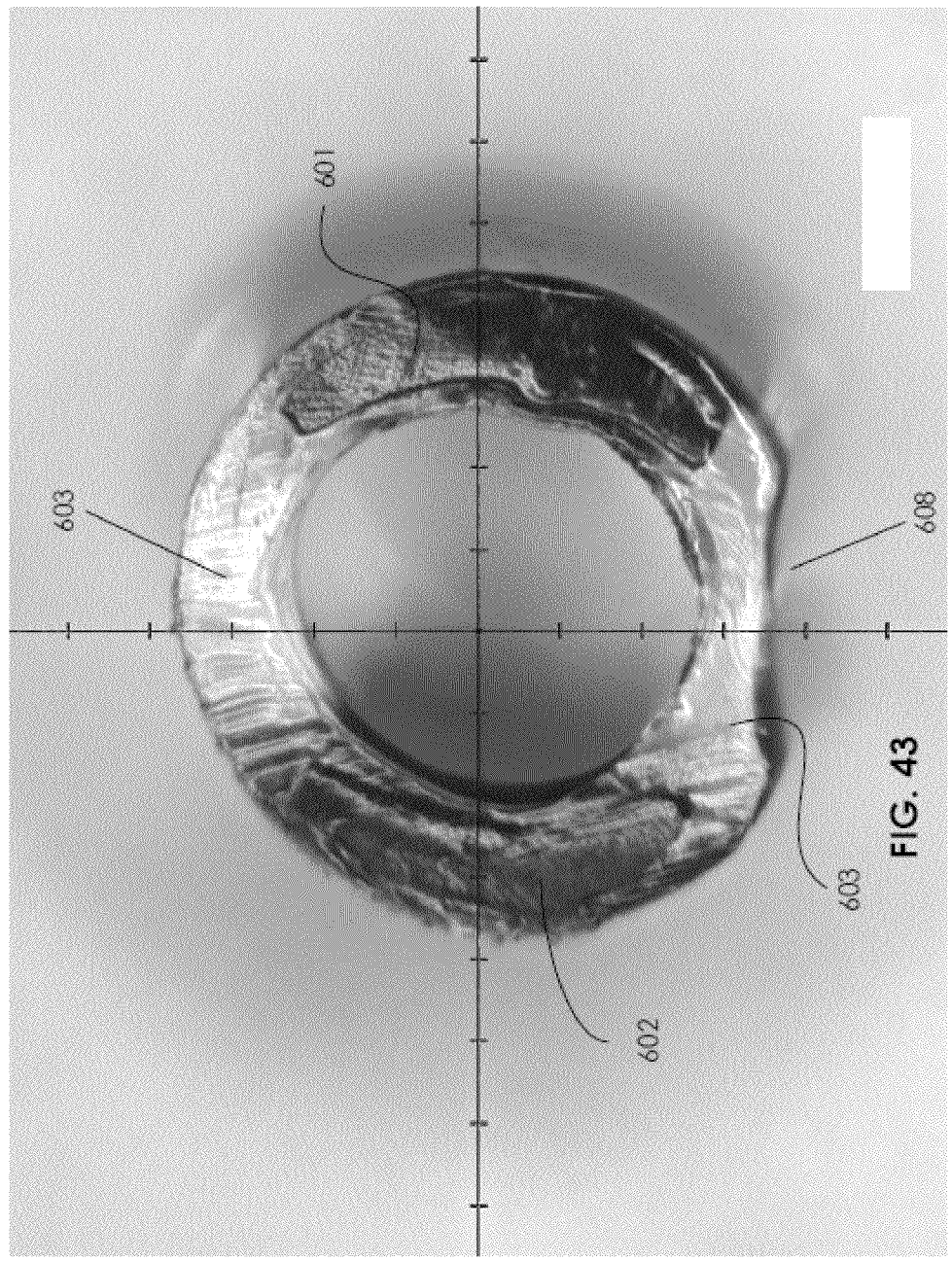
FIG. 43 shows a photographic cross section of the hollow electrode structure shown in FIG. 42.
Figure 44:
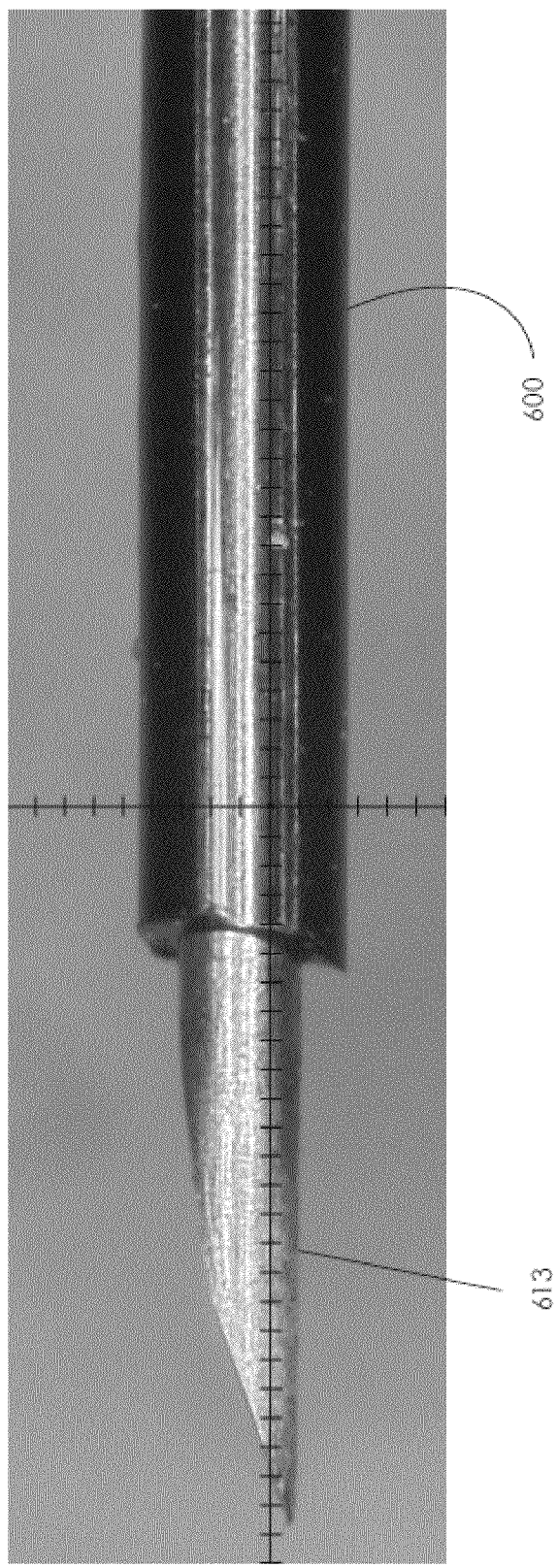
FIG. 44 shows a photograph of a hollow electrode structure and an insertion needle in accordance with the present disclosure.

In some embodiments, a hollow electrode structure according to the present disclosure will be connected via a connector to one or more devices and/or power sources. Such a connector can be configured using any of a wide variety of suitable materials. For example, in one embodiment, a suitable connector includes an elastomeric material. Suitable connectors can include one or more conductive materials which serve as electrode contacts as described in more detail below. An exemplary connector embodiment is provided with reference to FIGS. 40 and 41, wherein the electrode structure 600 is configured to engage a connector 614. The connector 614 includes first electrode contact 615 and second electrode contact 616 for engaging the first conductive material 601 and the second conductive material 602 respectively. As shown in FIGS. 40 and 41, connector 614 also includes non-conductive components 617 separating electrode contacts 615 and 616.

Figure 47:
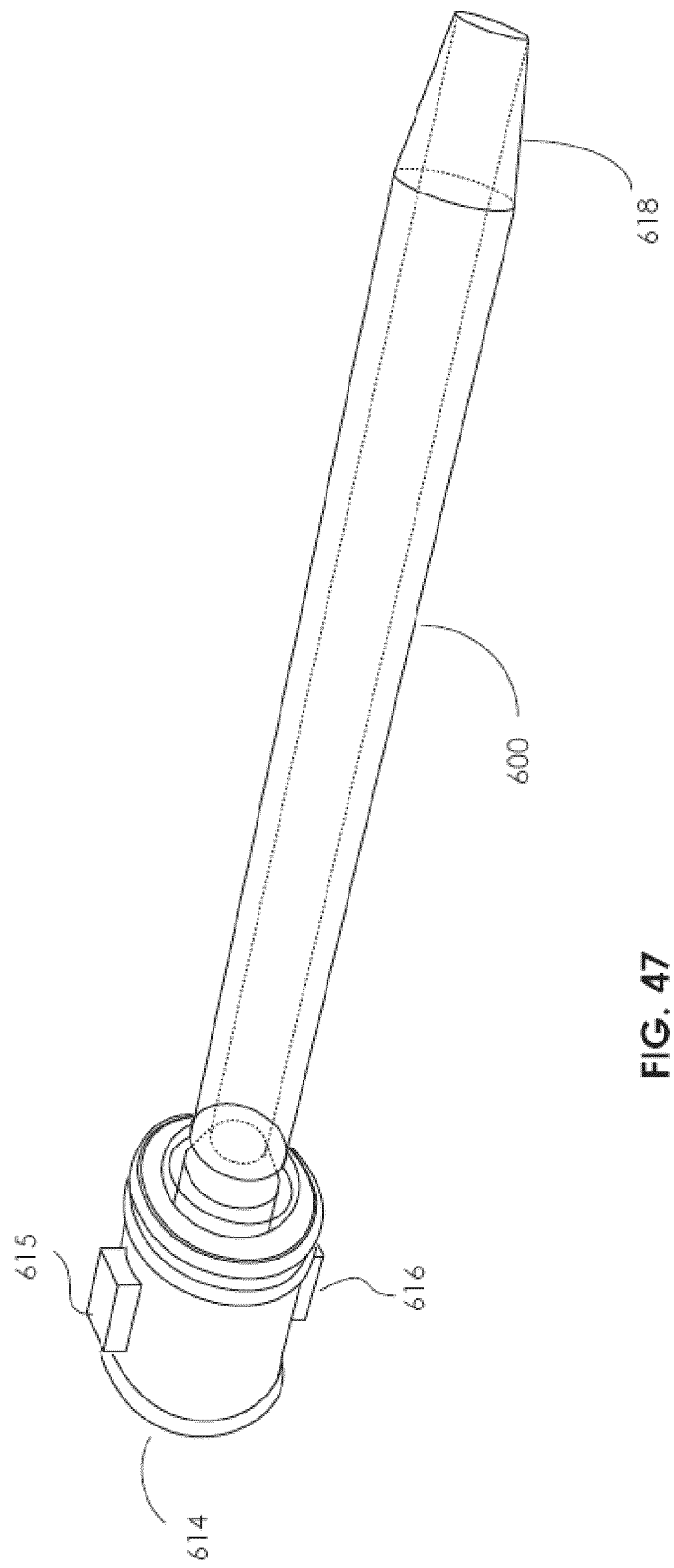
FIG. 47 shows an illustration of a hollow electrode structure having a tapered tip and engaged with a connector having electrode contacts for contacting the conductive materials of the hollow electrode structure.
Figure 48:
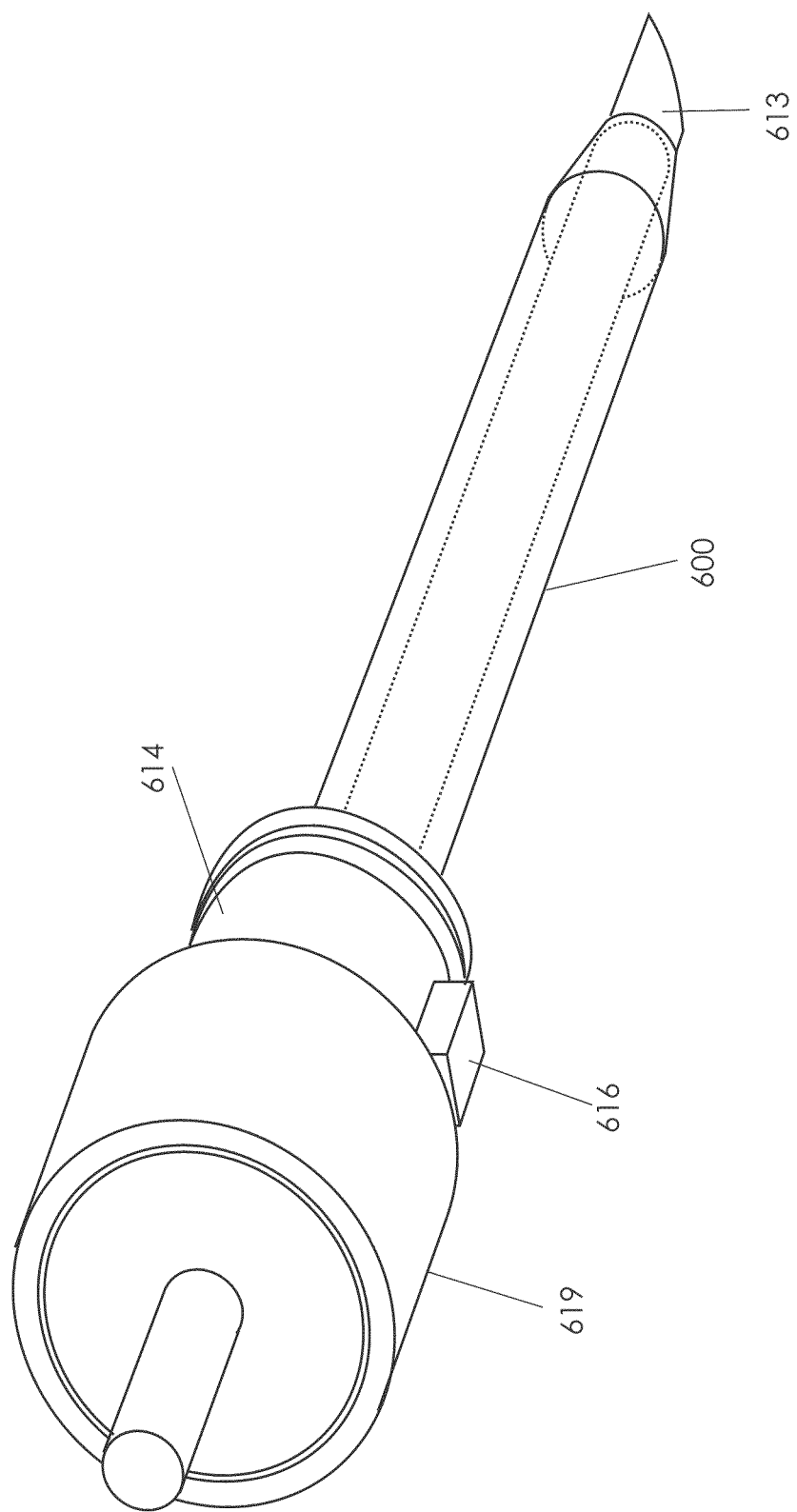
FIG. 48 shows the hollow electrode structure and connector of FIG. 47 engaged with an insertion needle and an insertion needle carrier.

FIG. 47 shows an embodiment in which electrode structure 600, including a tapered tip 618, is engaged with connector 614 having first electrode contact 615 and second electrode contact 616. FIG. 48 shows a further embodiment, in which the electrode structure 600 depicted in FIG. 47 is engaged with insertion needle 613 and insertion needle carrier 619.

An additional connection configuration is depicted in FIG. 49. An electrode structure 600, including a tapered tip 618, is configured for connection to a staggered connector (not shown). The electrode structure 600 includes a series of electrode contact bands 620, e.g., gold electrode contact bands, which contact exposed portions of conductive materials 601 and 602 (not shown in FIG. 49) in a staggered manner, e.g., at positions A and B respectively. The exposed portions of conductive materials 601 and 602 can be formed by skiving dielectric material 603 in appropriate locations. The series of electrode contact bands 620 are separated by a series of sealing rings 621 which provide a sealed connection when electrode structure 600 is inserted into a staggered connector (not shown).

Figure 50:
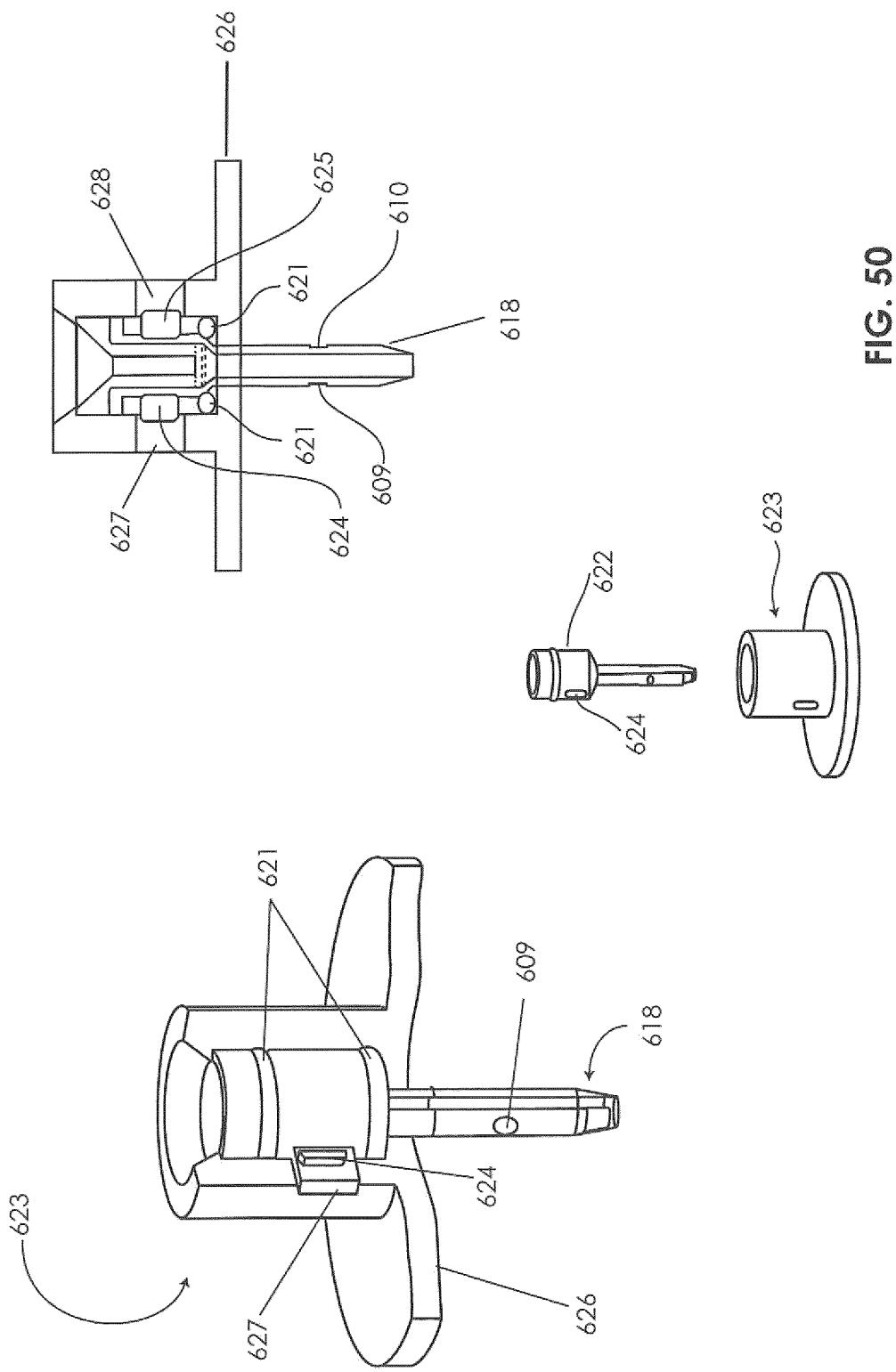
FIG. 50 shows three views of a connection configuration involving an electrode structure, a primary connector and a secondary connector.

FIG. 50 depicts a further connection configuration involving a primary connector 622 and a secondary connector 623. Primary connector 622 includes a first electrode contact 624 and a second electrode contact 625 which contact cutout portions of electrode structure 600 such that electrode contacts 624 and 625 contact first conductive material 601 and second conductive material 602 respectively. Primary connector 622 also includes sealing rings 621 which provide for a sealed connection between primary connector 622 and secondary connector 623. Any suitable conductive material can be used for first electrode contact 624 and second electrode contact 625, including, e.g., gold plated electrode contacts.

Secondary connector 623 includes a connector base 626 and electrode contacts 627 and 628. Connector base 626 can be injection molded and, in some embodiments, serves as an adhesive mount for attachment of electrode structure 600 to a suitable surface, e.g., the skin of a subject and/or patient. Electrode contacts 627 and 628 can be made of any suitable conductive material, e.g., conductive silicone, and provide an electrical connection to electrode contacts 624 and 625 respectively. In another embodiment, first electrode contact 624 and second electrode contact 625 extend a sufficient distance from primary connector 622 such that electrode contacts 627 and 628 are unnecessary and connection to a suitable device or power source can occur directly through electrode contacts 624 and 625.

Figure 51:
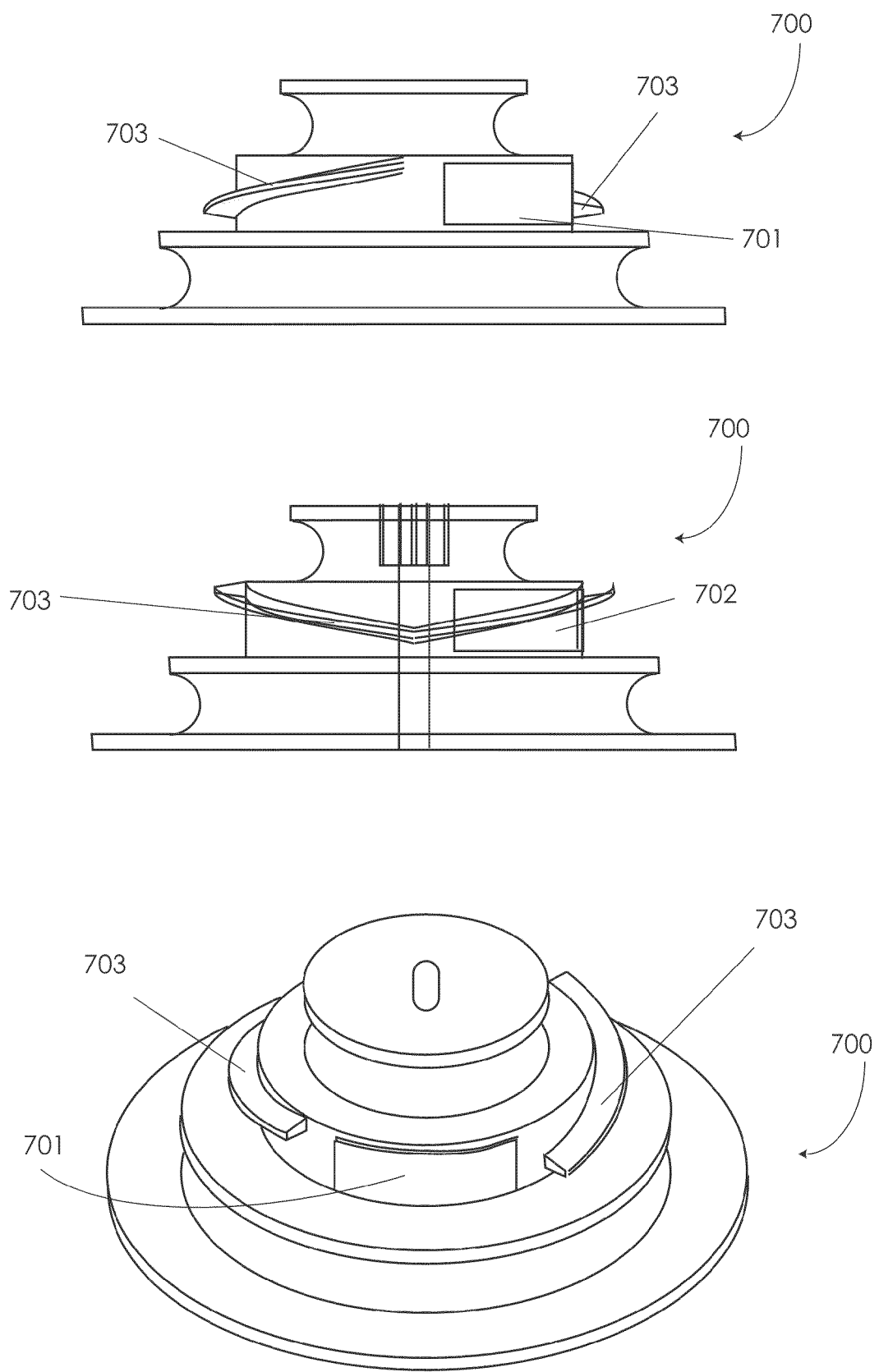
FIG. 51 shows an example of a connector for engaging an electrode structure according to the present disclosure, wherein the connector includes a first electrode contact and a second electrode contact for contacting a first conductive material and a second conductive material of electrode structure respectively; the connector includes screw threads for engaging corresponding screw threads on an additional device, e.g., a power source.

In one embodiment, a connector for engaging an electrode structure 600 has the configuration set forth in FIG. 51, wherein a connector 700 includes a first electrode contact 701 and a second electrode contact 702 for contacting first conductive material 601 and the second conductive material 602 of electrode structure 600 respectively. Connector 700 includes screw threads 703 for engaging corresponding screw threads on a device and/or power source.

Integrated Electrode Structures for In vivo Use

With reference to FIGS. 52-61, an exemplary integrated device including analyte sensor and insulin delivery capabilities is now described.

Figure 52:
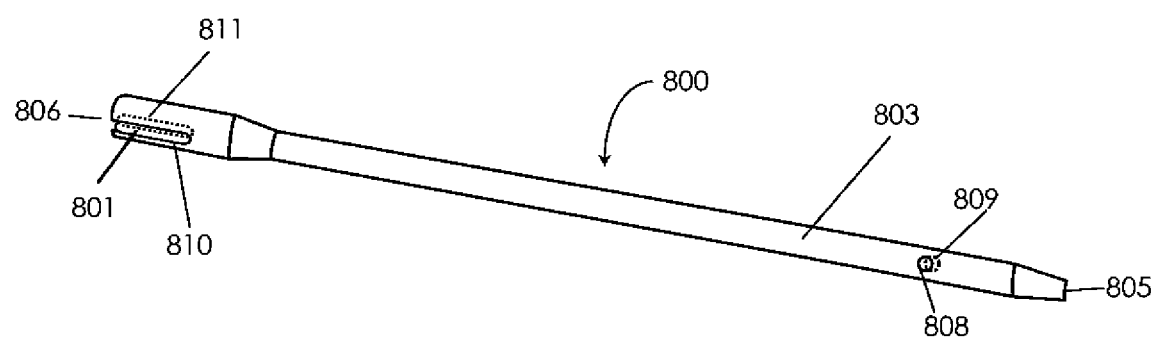
FIG. 52 shows an extruded analyte sensor according to the present disclosure, wherein the extruded analyte sensor includes a first conductive material which includes a working electrode and a second conductive material which includes a reference/counter electrode.

FIG. 52 shows an extruded analyte sensor 800, wherein the extruded analyte sensor 800 includes a first conductive material 801 which includes a working electrode. The extruded analyte sensor 800 also includes a second conductive material (not shown) which includes a reference/counter electrode. The first and second conductive materials are coextruded with a dielectric material 803 to produce an analyte sensor wherein first conductive material 801 and second conductive material 802 are electrically isolated by the dielectric material 803. The working electrode includes a sensing layer disposed on, in or proximate thereto.

The analyte sensor 800 includes a lumen (not shown), wherein the lumen includes a first opening 805, a second opening 806, and a lumen wall (not shown). The dielectric material 803 defines the lumen wall, and the first and second conductive materials are provided, e.g., embedded or positioned, in the dielectric material 803.

As shown in FIG. 52, the extruded analyte sensor 800 includes a first cutout 808 in the dielectric material 803 which exposes the working electrode and a second cutout 809 in the dielectric material 803 which exposes the reference/counter electrode. These cutouts provide regions for contact between a sample, e.g., an analyte containing fluid, and the working and reference/counter electrodes. In addition, the cutout 808 which exposes the working electrode provides a location for the deposition of the sensing layer of the working electrode.

As shown in FIG. 52, extruded analyte sensor 800 includes a third cutout portion 810 and a fourth cutout portion 811. The third cutout portion 810 exposes a portion of the first conductive material 801 and the fourth cutout portion 811 exposes a portion of the second conductive material 802. Cutout portions 810 and 811 provide exposed portions of their respective conductive materials which facilitate electrical connection of the extruded analyte sensor 800 to a sensor connector 812 as shown in FIG. 53.

Figure 53:
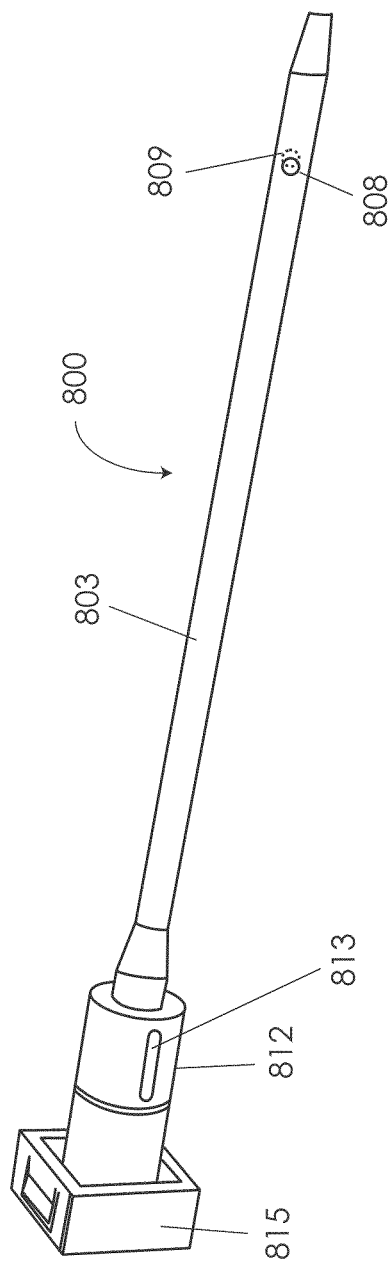
FIG. 53 shows the extruded analyte sensor of FIG. 52 engaged with a sensor connector having a first electrode contact and a second electrode contact which contact the first conductive material and the second conductive material respectively when the sensor connector is engaged with the extruded analyte sensor; the sensor connector also includes a sensor connection hub which is configured to engage with an insulin delivery tube.
Figure 54:
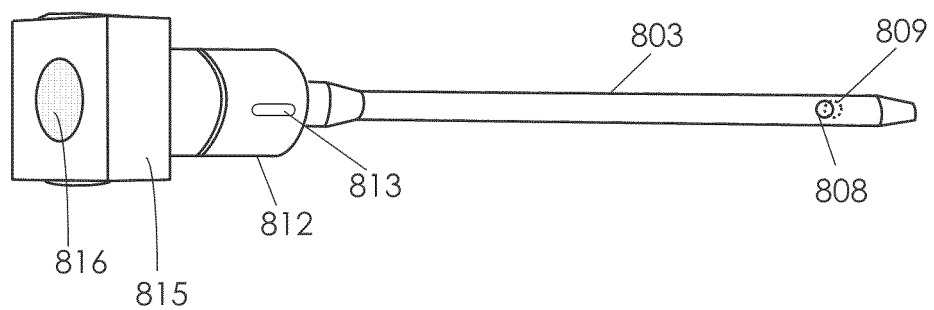
FIG. 54 shows another view of the extruded analyte sensor of FIG. 53, which includes a septum which provides a seal for the sensor connection hub.

FIG. 53 shows the extruded analyte sensor 800 of FIG. 52 engaged with a sensor connector 812. Sensor connector 812 has a first electrode contact 813 and a second electrode contact (not shown) which contact conductive material 801 and conductive material 802 respectively when sensor connector 812 is engaged with extruded analyte sensor 800. Sensor connector 812 also includes a sensor connection hub 815 which is configured to engage with an insulin delivery tube. Sensor connection hub 815 includes a septum 816 as shown in FIG. 54, e.g., a silicon septum which may be a self-sealing septum, which provides a seal for sensor connection hub 815.

Figure 55:
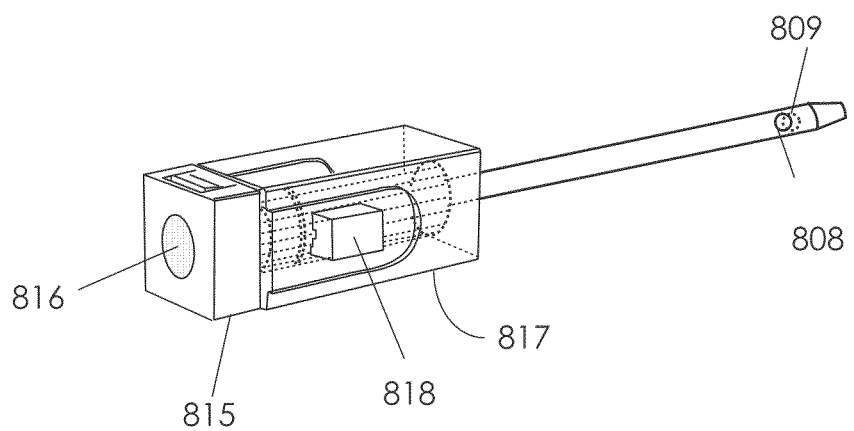
FIG. 55 shows the extruded analyte sensor of FIG. 54 with a housing which engages the extruded analyte sensor and the sensor connector; the housing includes electrode contacts which contact the electrode contacts of the sensor connector.

A housing 817, e.g., a silicon housing, engages the extruded analyte sensor 800 and the sensor connector 812, as shown in FIG. 55. Housing 817 includes electrode contacts 818 and 819 which contact first electrode contact 813 and a second electrode contact respectively.

Figure 56:
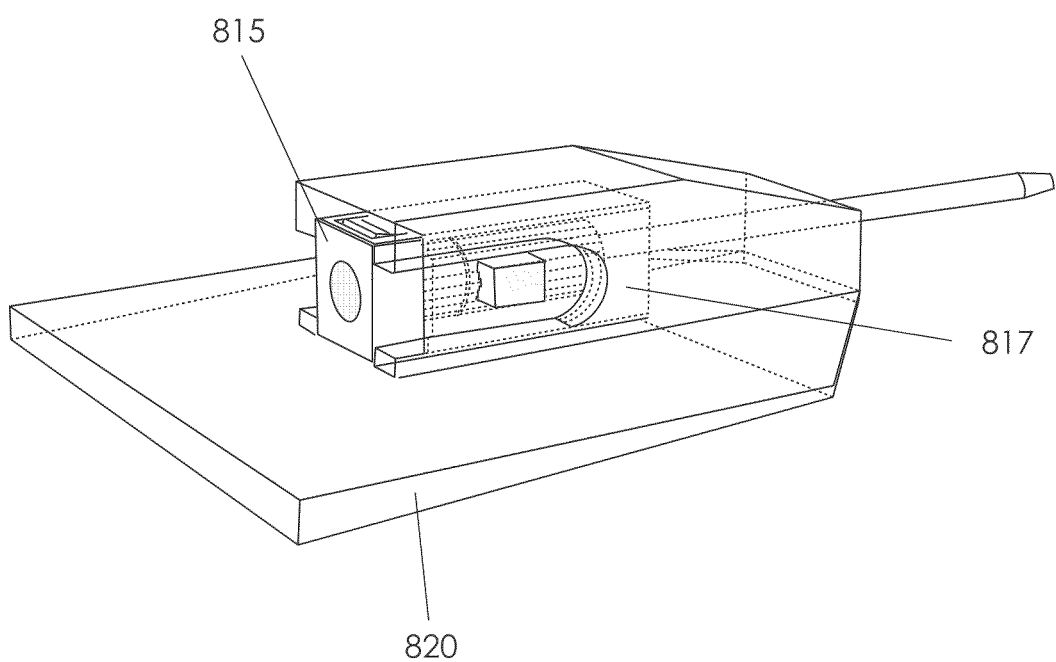
FIG. 56 shows a sensor/tube mount engaged with the housing and sensor connection hub of FIG. 55.

A sensor/tube mount 820 engages housing 817 and sensor connection hub 815 as shown in FIG. 56. In some embodiments, sensor/tube mount 820 includes an optional adhesive for attachment (not shown) to the body of a subject and/or patient.

Figure 57:
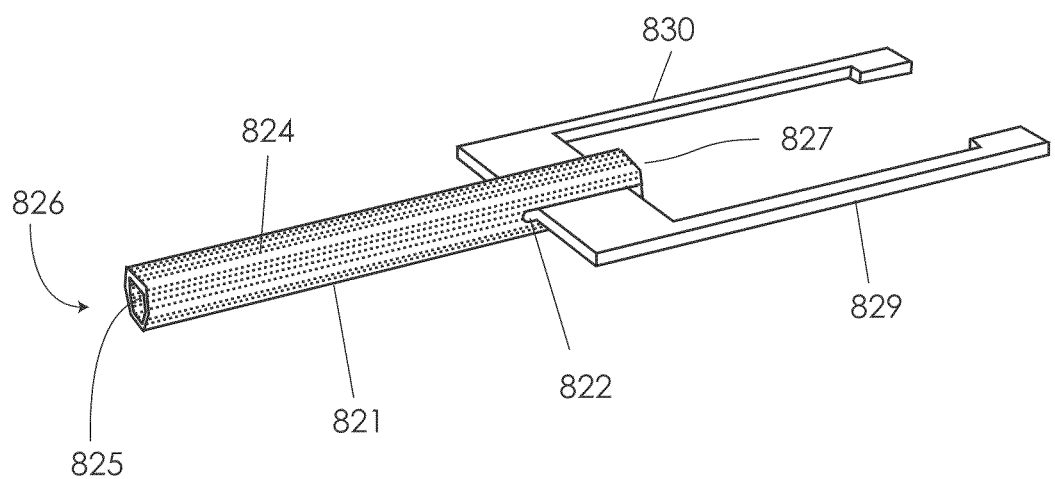
FIG. 57 shows an insulin delivery tube which includes a first conductive material and a second conductive material.

FIG. 57 shows an insulin delivery tube 821. Like extruded analyte sensor 800, insulin delivery tube 821 includes a first conductive material 822 and a second conductive material (not shown). The first and second conductive materials can be coextruded with a dielectric material 824 to produce an insulin delivery tube 821 wherein first conductive material 822 and the second conductive material are electrically isolated by the dielectric material 824.

The insulin delivery tube 821 includes a lumen 825, wherein the lumen includes a first opening 826, a second opening 827, and a lumen wall (not shown). The dielectric material 824 defines the lumen wall (not shown), and the first and second conductive materials are provided, e.g., embedded, in the dielectric material 824. The insulin delivery tube 821 also includes electrode contacts 829 and 830 which contact the first conductive material 822 and the second conductive material 823 respectively. Electrode contacts 829 and 830 are configured such that when insulin delivery tube 821 is engaged with housing 817 and sensor connection hub 815, electrode contact 829 contacts electrode contact 818 and electrode contact 830 contacts electrode contact 819, thereby providing an electrical connection between conductive material 822 and conductive material 801, and between conductive material 823 and conductive material 802.

Figure 58:
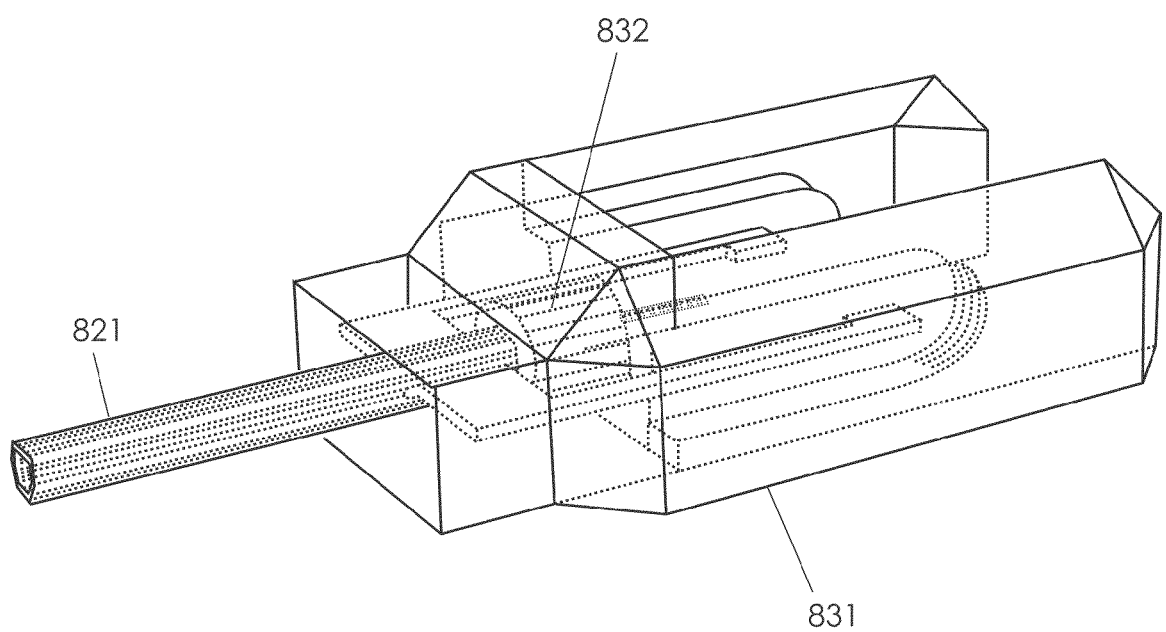
FIG. 58 shows the insulin delivery tube of FIG. 57, wherein the insulin delivery tube is engaged with an insulin delivery tube mount and an attachment hub; the insulin delivery tube mount is configured to engage the sensor/tube mount shown in FIG. 56; the attachment hub is configured to engage the sensor connection hub shown in FIG. 56.
Figure 59:
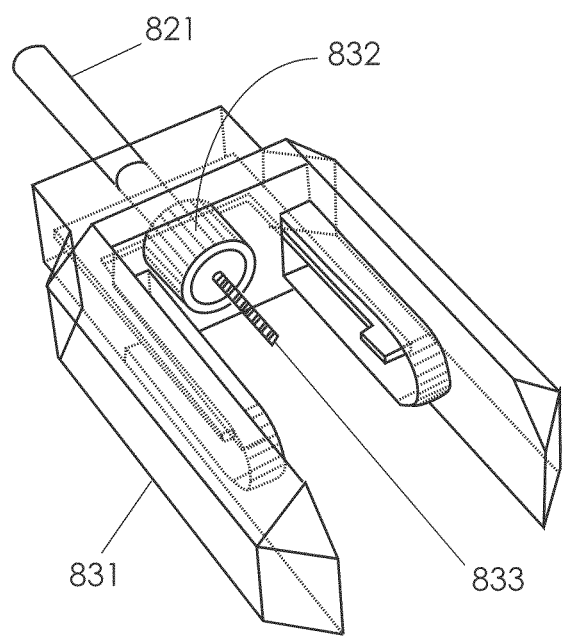
FIG. 59 shows another view of the insulin delivery tube, insulin delivery tube mount, and attachment hub shown in FIG. 58.
Figure 60:
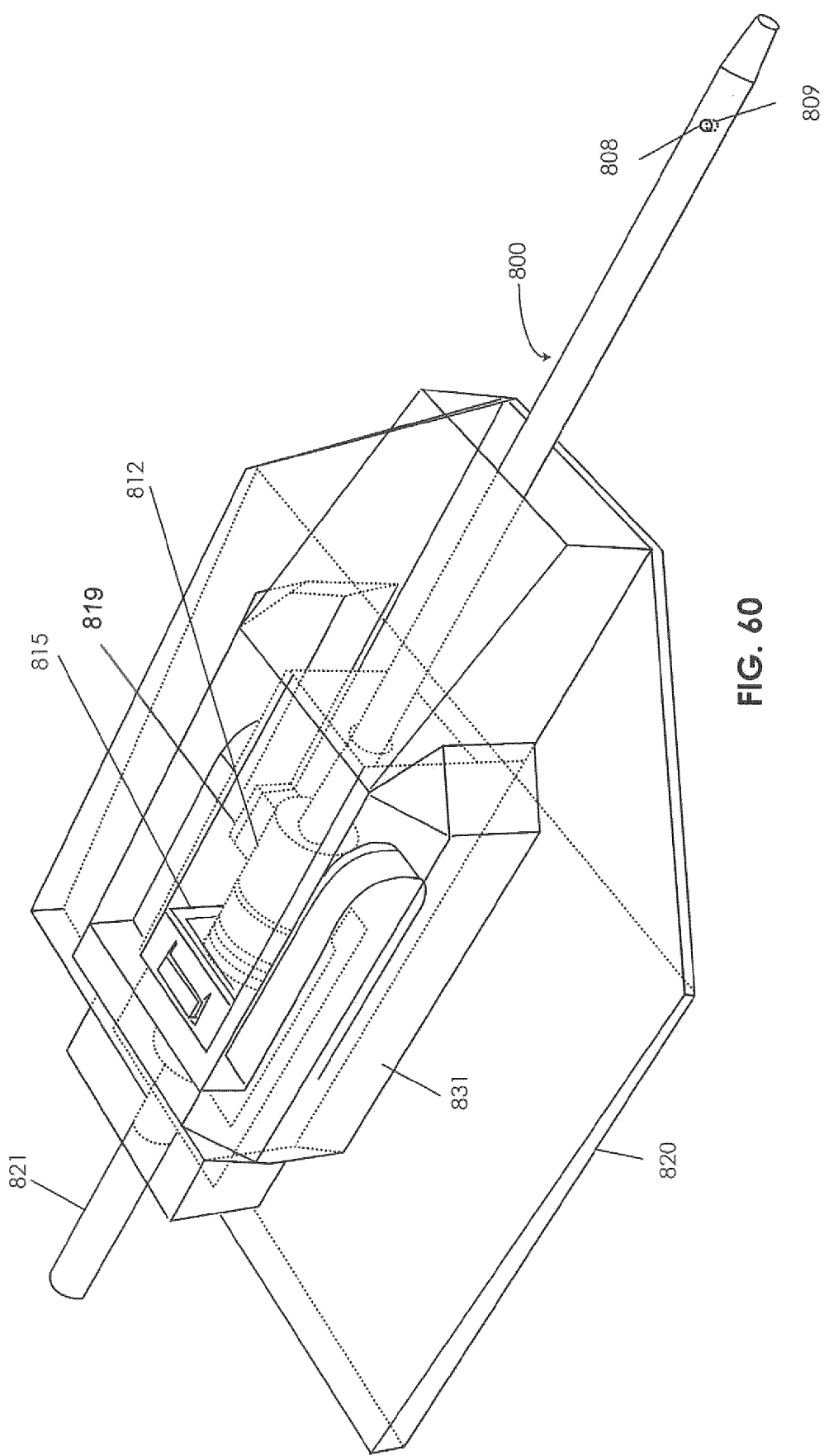
FIG. 60 shows a depiction of an integrated device, including an insulin delivery tube and an extruded analyte sensor as shown in FIGS. 52-59.
Figure 61:
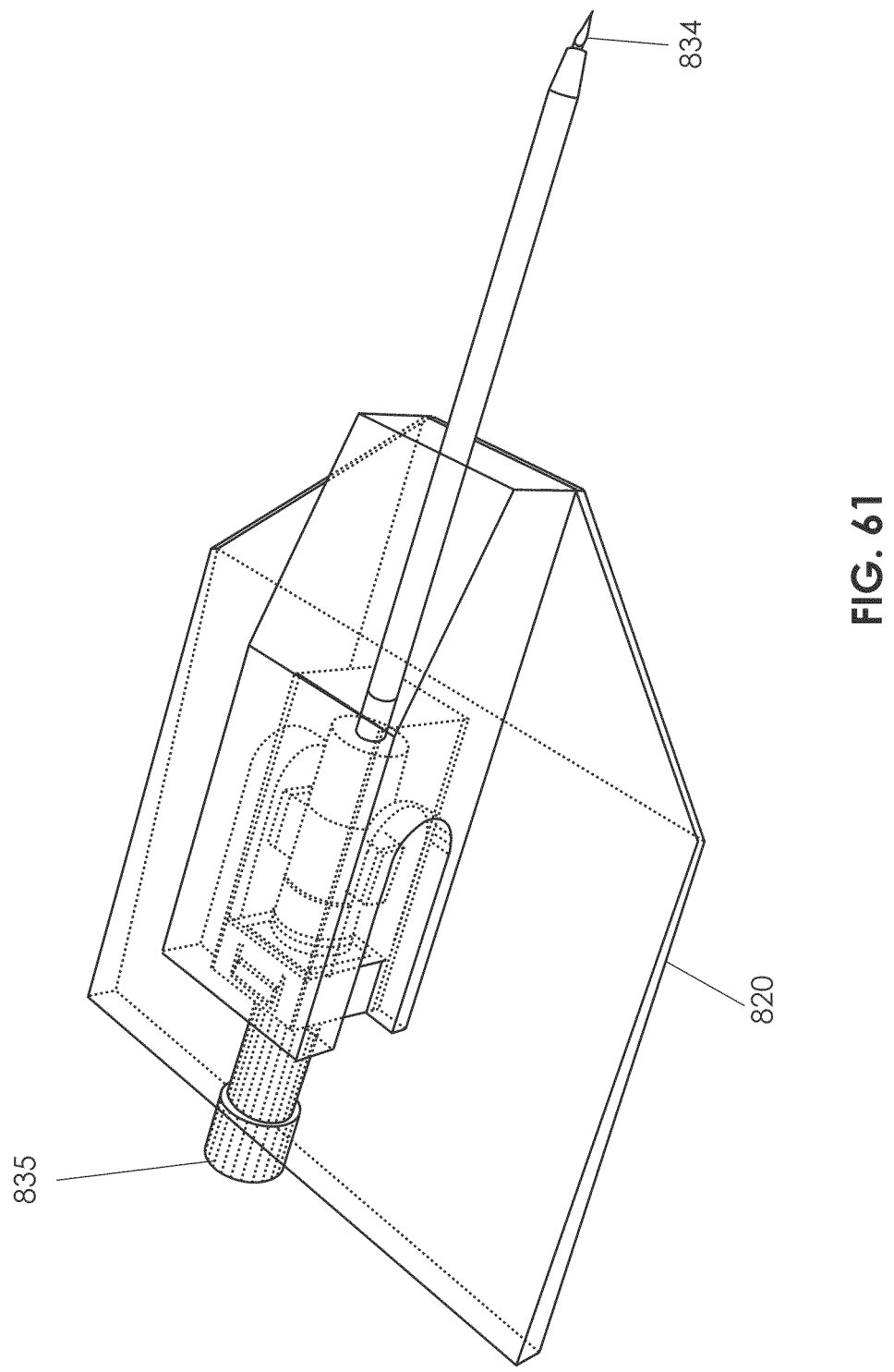
FIG. 61 shows the integrated device of FIG. 60 prior to engagement of the insulin delivery tube mount with the sensor/tube mount; an insertion needle having an insertion needle handle is depicted which can be utilized to insert the extruded analyte sensor into the body of a subject and/or patient.

As shown in FIG. 58-60, insulin delivery tube 821 is configured to engage an insulin delivery tube mount 831 and an attachment hub 832. Insulin delivery tube mount 831 is configured to engage sensor/tube mount 820, and attachment hub 832 is configured to engage sensor connection hub 815. Attachment hub 832 includes a needle 833 which is designed to puncture septum 816 of connection hub 815 upon engagement of attachment hub 832 with sensor connection hub 815. A depiction of the integrated device, including delivery tube 821 and extruded analyte sensor 800, is provided in FIG. 60. As shown in FIG. 61, prior to engagement of insulin delivery tube mount 831 with sensor/tube mount 820, an insertion needle 834 having an insertion needle handle 835 can be utilized to insert extruded analyte sensor 800 into the body of a subject and/or patient.

While the integrated device depicted cumulatively in FIGS. 52-61 has been described herein for convenience as an integrated analyte sensor and insulin delivery device, it should be noted that the analyte sensor can be used to detect any of a wide variety of analytes and the integrated device can be used to delivery any of a wide variety of medications, drugs or therapeutic agents.

Figure 62:
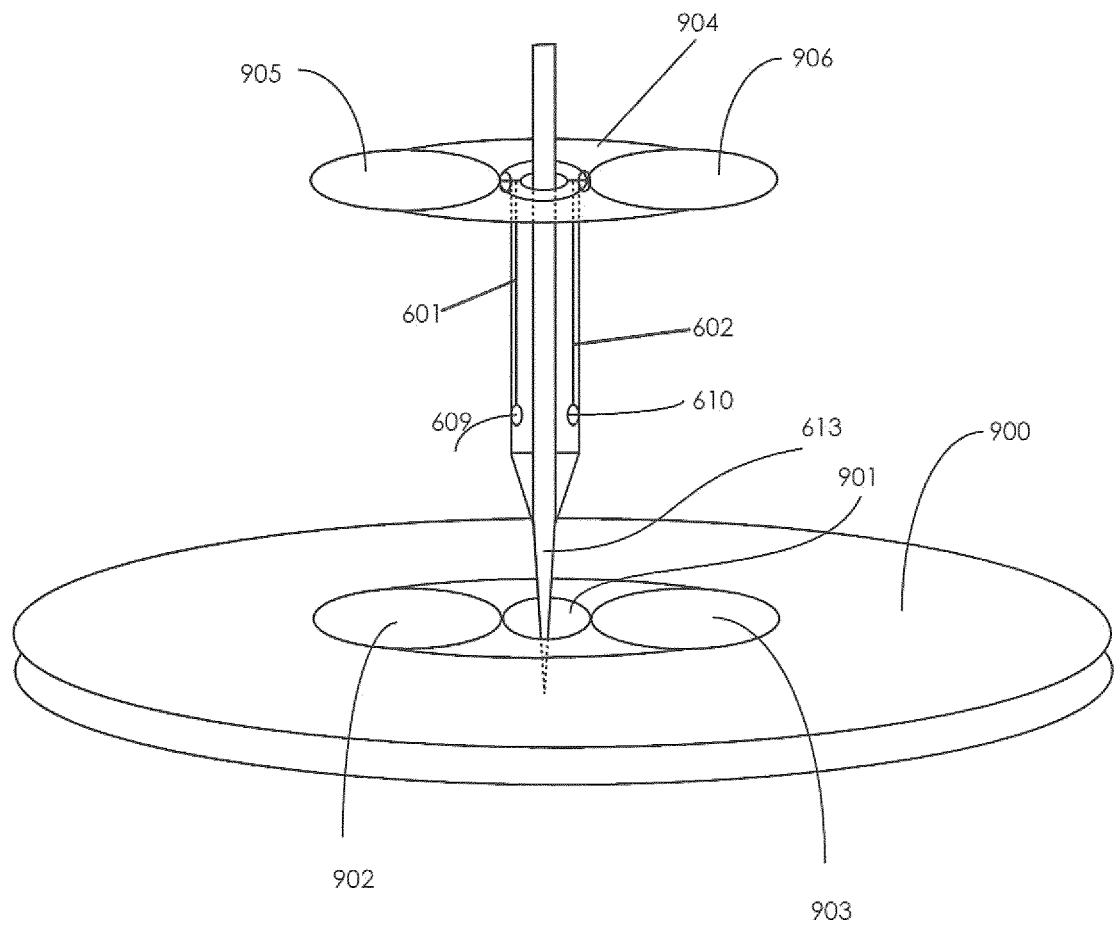
FIG. 62 shows an additional integrated electrode structure according to the present disclosure.

An additional integrated electrode structure according to the present disclosure is provided in FIG. 62. In this embodiment, an electrode structure 600 as described previously herein with reference to FIG. 45 is configured for insertion into a subject and/or patient through an insertion pad 900. The insertion pad 900 includes an insertion site 901, electrode contact 902, electrode contact 903, and optional electronics (not shown) including, for example, an analog interface, one or more processors, etc., capable of receiving and/or processing sensor signals from electrode contacts 902 and 903. The electrode structure 600 is modified to include a contact pad 904, which includes electrode contacts 905 and 906. Upon insertion of electrode structure 600 at insertion site 901, electrode contact 905 comes into contact with electrode contact 902 and electrode contact 906 comes into contact with electrode contact 903, thereby providing a conductive path from conductive material 601 to electrode contact 902 and from conductive material 602 to electrode contact 903. As such, where electrode structure 600 is configured as an analyte sensor, portions of the insertion pad 900 are in signal communication with the analyte sensor. Sensor signals received from electrode structure 600 can be transmitted to a suitable receiver via the electronics including a transmitter, e.g., using an RF data transmission protocol.

As discussed above, in some embodiments extruded analyte sensors according to the present disclosure can be configured to deliver one or more medications through lumens of the analyte sensors. In some embodiments, the amount or dose of medication delivered is based at least in part on an analyte concentration determined using the analyte sensor. In some embodiments, it may be desirable to alternate and/or perform at different times the sensing and medication delivery functions of the extruded analyte sensor. For example, the analyte sensor can be configured such that it does not take an analyte reading during, or within a defined time period of, the period of time medication is actively being delivered to a subject through the lumen of the analyte sensor. A period of time can be selected which allows the subject's metabolism to adjust to the delivered medication such that an analyte measurement taken using the analyte sensor will be representative of the ambient analyte concentration. Such a defined time period can be, e.g., 1 to 5 sec, 5 to 10 sec, 10 to 20 sec, 20 to 30 sec, 30 to 40 sec, 40 to 50 sec or more; or 1 to 5 minutes or more. Such a configuration may prevent temporal alterations in analyte concentration, which may occur in the immediate vicinity of the analyte sensor upon medication delivery, from affecting the representative nature of the measured analyte concentration, e.g. where the measured glucose concentration is representative of the ambient glucose concentration of the subject.

Fill Assist

In some embodiments, the electrode structures described herein include one or more optional fill assist structures, e.g., one or more notches, cut-outs, indentations, and/or protrusions, which facilitate the collection of a fluid sample. For example, the analyte sensor can be configured such that the proximal end of the analyte sensor is narrower than the distal end of the analyte sensor. In one such embodiment, the analyte sensor comprises a tapered tip at the proximal end of the analyte sensor. Additional fill assist structures are described in U.S. Patent Publication No. 2008/0267823, the disclosure of which is incorporated by reference herein; and U.S. patent application Ser. No. 11/461,725, filed Aug. 1, 2006, the disclosure of which is incorporated by reference herein.

Fill Indicator Electrode

In some instances, it may be desirable to be able to determine when the reaction chamber is filled. Accordingly, the electrode structures can include a fill indicator, such as one or more indicator electrodes that can be used to determine when the reaction chamber has been filled. In some embodiments, conductive materials to be configured as one or more indicator electrodes will be coextruded along with the conductive materials to be configured as working and reference/counter electrodes. For example, with reference to FIG. 1, optional third conductive material 104 can be configured as a fill-indicator electrode.

In the context of a hollow electrode structure, indicator electrodes can be prepared as follows. In one embodiment, a hollow electrode structure is formed such that third and fourth conductive materials are coextruded with first and second conductive materials, wherein the first and second conductive materials are to be configured as working and reference/counter electrodes respectively. The third and fourth conductive materials are provided, e.g., embedded or positioned, in dielectric material and located on opposite sides of a lumen from each other, such that a hole extending through the dielectric material and at least substantially perpendicular to the lumen exposes a portion of the third and fourth conductive material. In one such embodiment, when a fluid sample fills the electrode structure up to the hole, the fluid sample contacts the exposed portions of the third and fourth conductive materials thereby creating an electrical short which indicates filling of the electrode structure.

In some embodiments, when fluid reaches an indicator electrode, the signal from that electrode will change. Suitable signals for observing include, for example, voltage, current, resistance, impedance, or capacitance between the indicator electrode and, for example, working electrode. Alternatively, the sensor can be observed after filling to determine if a value of the signal (e.g., voltage, current, resistance, impedance, or capacitance) has been reached indicating that the reaction chamber is filled.

The electrode structure or equipment that the electrode structure is connected with (e.g., an analyte meter) can include a sign (e.g., a visual sign or auditory signal) that is activated in response to the indicator electrode to alert the user that the reaction chamber has been filled. The electrode structure or equipment can be configured to initiate a reading when the indicator electrode indicates that the reaction chamber has been filled with or without alerting the user. The reading can be initiated, for example, by applying a potential between the working electrode and the reference and/or counter electrode and beginning to monitor the signals generated at the working electrode. Additional description of fill indicator electrodes can be found in U.S. Pat. No. 6,592,745, the disclosure of which is incorporated by reference herein.

Figure 63:
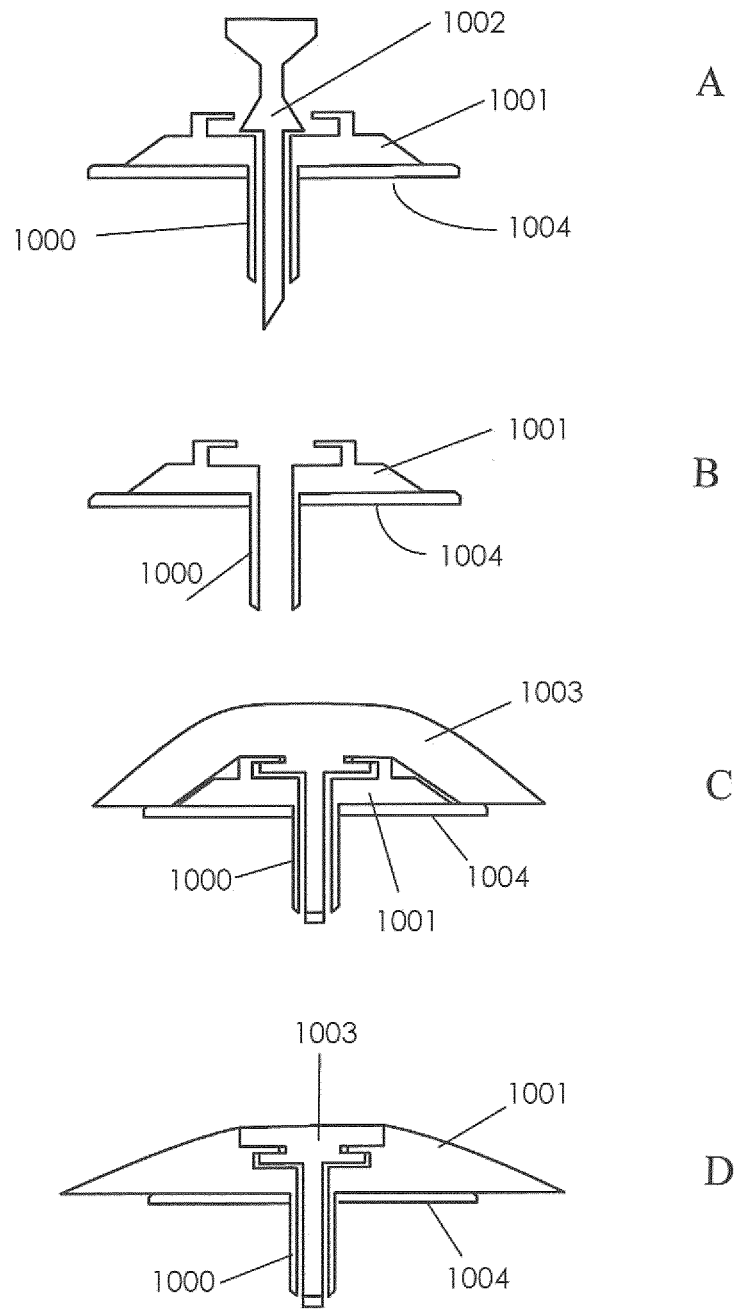
FIG. 63 provides an illustration of a method for inserting an electrode structure into subcutaneous tissue of a subject and/or patient.

Method of Inserting an Electrode Structure into Subcutaneous Tissue of a Subject With reference to FIG. 63, a method of inserting an electrode structure into subcutaneous tissue of a subject and/or patient is now described. In the embodiment, shown in FIG. 63, the method includes an insertion step in which a catheter 1000 having a catheter assembly 1001 is inserted into subcutaneous tissue of a subject and/or patient using an insertion needle 1002 positioned inside the catheter 1000 (Panel A). The insertion needle 1002 is subsequently removed from the subcutaneous tissue of the subject and/or patient (Panel B). An electrode structure 1003 is then inserted into the catheter 1000 and attached to the catheter assembly 1001 such that a portion of the electrode structure 1003 is exposed to the subcutaneous tissue (Panel C).

Optionally, the catheter assembly 1001 can include an adhesive backing 1004. This adhesive backing 1004 can facilitate the attachment of the catheter assembly 1001 to the surface of the skin of a subject and/or patient. Accordingly, the above method can include an additional step of attaching the catheter assembly to the surface of the skin of the subject and/or patient, e.g. via contacting the adhesive backing 1004 with the surface of the skin of the subject and/or patient.

In one embodiment, the electrode structure itself includes sensor electronics, e.g., a power supply, transmitter, etc. (not shown) (Panel C). In another embodiment, the catheter assembly includes the sensor electronics, e.g., a power supply, transmitter, etc. (not shown) (Panel D) coupled to the electrode structure.

It should be noted that electrode structure 1003 is not limited to a particular electrode structure and any of the electrode structures described herein may be used or adapted for use with the above method. For example, the above method may be adapted for use with the hollow or solid electrode configurations described herein with respect to in vivo use.

Operation of Extruded Electrode Structures

Extruded electrode structures according to the present disclosure find use in a variety of applications, including, but not limited to, in vitro and in vivo analyte detection and/or monitoring.

In one embodiment, in the context of in vitro analyte detection and/or monitoring, a fluid sample is generally introduced into a reaction chamber of an extruded electrode structure and exposed to an analyte responsive enzyme and a redox mediator. A sensor signal is produced as a result of the interaction of the analyte responsive enzyme, the redox mediator, and the analyte when present. This signal can be communicated via one or more conductive materials of the electrode structure to an analyte meter designed to receive the sensor signal. In some embodiments, this communication occurs through one or more connectors which facilitate transfer of the sensor signal. The fluid sample can be provided by lancing the skin of a subject and/or patient to produce a blood drop which is then contacted by the electrode structure.

In one embodiment, in the context of in vivo analyte detection and/or monitoring, a portion of an extruded electrode structure is inserted into the tissue, e.g., the subcutaneous tissue, of a subject and/or patient. As described previously herein, the electrode structure can include an insertion needle and/or a tapered tip to facilitate the insertion process. Once the electrode structure is inserted, the internal environment of the tissue is generally exposed to an analyte responsive enzyme and a redox mediator located in a sensing layer disposed on, in, or in proximity to a working electrode. It should be noted that for in vivo purposes the electrode structure need not be completely inserted into the tissue of a patient. For example, the electrode can include a first portion which is designed for insertion into a tissue of a subject and/or patient and a second portion which is positioned outside the body of the subject and/or patient. This second portion can be designed to connect to an external device, e.g., an analyte monitoring device and/or a transmitter. In some embodiments, the electrode structure includes a portion positionable above a surface of the skin, and a portion positioned below the surface of the skin, e.g., penetrating through the skin and into, e.g., the subcutaneous space.

The length of the inserted portion of the extruded electrode structure can vary depending on the particular application. For example, in one embodiment, where the electrode structure is configured to operate as both an analyte sensor and a medication delivery tube, e.g., an insulin delivery tube, a portion of the electrode structure that is about 10 mm to about 15 mm in length is inserted into the tissue of a subject and/or patient. A portion of the electrode structure having a length of about 3 mm is positioned outside the body of the subject and/or patient for connection to an external device.

A sensor signal is produced as a result of the interaction of the analyte responsive enzyme, the redox mediator, and the analyte when present. This signal can be communicated via one or more conductive materials of the electrode structure to a device designed to receive the sensor signal. In some embodiments, this communication occurs through one or more connectors which facilitate transfer of the sensor signal. Details relating to the receipt of an analyte signal from an analyte sensor and the determination of a concentration of analyte are described, for example, in U.S. Pat. No. 7,041,468, the disclosure of which is incorporated by reference herein.

The disclosed electrode structures may be operated with or without applying a potential. In one embodiment, an electrochemical reaction occurs spontaneously at a working electrode and a reference/counter electrode provides a background signal.

In another embodiment, a potential is applied between the working and reference/counter electrodes. This potential does not need to remain constant. The magnitude of the required potential is dependent on the redox mediator. The potential at which the electrode poises itself, or where it is poised by applying an external bias, and where the analyte is electrolyzed is typically such that the electrochemical reaction is driven to or near completion. In some examples the electrochemical reaction is not oxidizing enough to result in significant electrochemical reaction of interferents, such as urate, ascorbate, and acetaminophen, that may affect the signal measured. For non-releasable redox mediators, the potential is typically between about −350 mV and about +400 mV versus the standard calomel electrode (SCE). In some exemplary embodiments, the potential of the redox mediator is more negative than +100 mV, e.g., the potential is more negative than 0 mV. In some embodiments, the potential is about −150 mV versus SCE.

When an external potential is applied, it may be applied either before or after the sample has been placed in the electrode structure. In one embodiment, when a potential is applied and the sample is in a reaction chamber, an electrical current will flow between the working electrode and the reference/counter electrode. The current is a result, at least in part, of the electrolysis of the analyte in the sample. This electrochemical reaction occurs via the redox mediator and the optional second electron transfer agent. Examples of specific electrochemical reactions which can be utilized in connection with the disclosed analyte sensors are described in detail in U.S. Pat. No. 6,592,745, the disclosure of which is incorporated by reference herein.

A variety of measurement techniques may be utilized to detect and/or quantitate an analyte using the electrochemical signal generated by the sensor. These include, e.g., amperometry, coulometry, potentiometry, and/or voltometry, including square wave voltometry.

Self Powered Analyte Sensors

In some embodiments, where the electrode structures described herein are configured as analyte sensors, the electrode structures are configured for connection to an external power supply. In other embodiments, electrode structures configured as analyte sensors are self-powered. For example, the electrode structures described herein can be configured such that they spontaneously pass a current directly proportional to analyte concentration in the absence of an external power source, e.g., as described in U.S. patent application Ser. No. 12/393,921, filed Feb. 26, 2009, the disclosure of which is incorporated by reference herein.

Data Monitoring and Management System

Figure 64:
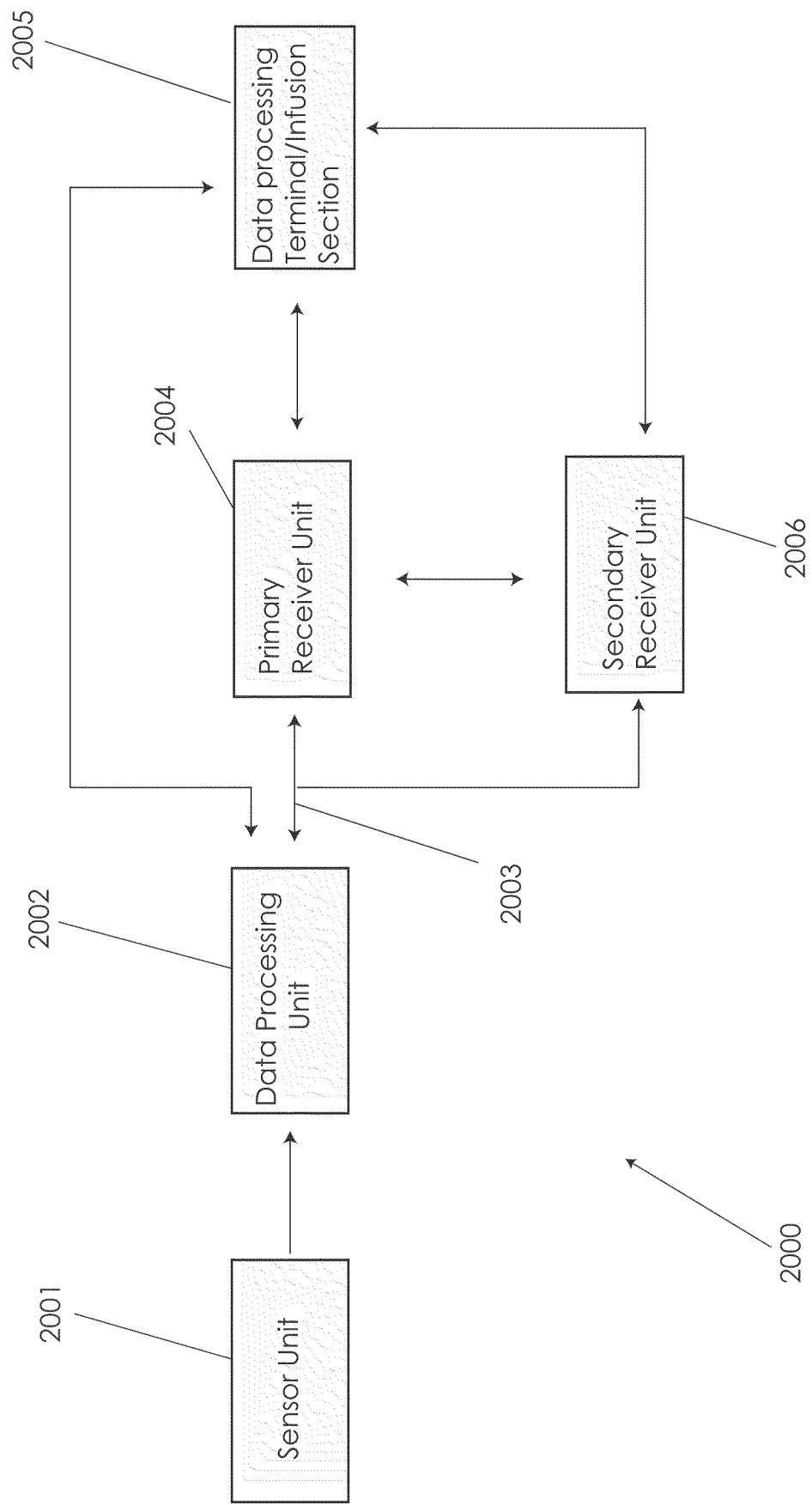
FIG. 64 shows a block diagram of a data monitoring and management system according to the present disclosure.

The electrode structures described herein can be configured for use in a data monitoring and management system. FIG. 64 shows a data monitoring and management system such as, for example, an analyte (e.g., glucose) monitoring system 2000 in accordance with certain embodiments. Embodiments of the present disclosure are further described primarily with respect to glucose monitoring devices and systems, and methods of glucose detection, for convenience only and such description is in no way intended to limit the scope of the invention. It is to be understood that the analyte monitoring system may be configured to monitor a variety of analytes at the same time or at different times.

The analyte monitoring system 2000 includes a sensor unit 2001, which includes an extruded electrode structure as described herein, a data processing unit 2002 connectable to the sensor unit 2001, and a primary receiver unit 2004 which is configured to communicate with the data processing unit 2002 via a communication link 2003. In certain embodiments, the primary receiver unit 2004 may be further configured to transmit data to a data processing terminal 2005 to evaluate or otherwise process or format data received by the primary receiver unit 2004. The data processing terminal 2005 may be configured to receive data directly from the data processing unit 2002 via a communication link which may optionally be configured for bi-directional communication. Further, the data processing unit 2002 may include a transmitter or a transceiver to transmit and/or receive data to and/or from the primary receiver unit 2004 and/or the data processing terminal 2005 and/or optionally the secondary receiver unit 2006.

Also shown in FIG. 64 is an optional secondary receiver unit 2006 which is operatively coupled to the communication link 2003 and configured to receive data transmitted from the data processing unit 2002. The secondary receiver unit 2006 may be configured to communicate with the primary receiver unit 2004, as well as the data processing terminal 2005. The secondary receiver unit 2006 may be configured for bi-directional wireless communication with each of the primary receiver unit 2004 and the data processing terminal 2005. As discussed in further detail below, in certain embodiments the secondary receiver unit 2006 may be a de-featured receiver as compared to the primary receiver, i.e., the secondary receiver may include a limited or minimal number of functions and features as compared with the primary receiver unit 2004. As such, the secondary receiver unit 2006 may include a smaller (in one or more, including all, dimensions), compact housing or embodied in a device including a wrist watch, arm band, PDA, etc., for example. Alternatively, the secondary receiver unit 2006 may be configured with the same or substantially similar functions and features as the primary receiver unit 2004. The secondary receiver unit 2006 may include a docking portion to be mated with a docking cradle unit for placement by, e.g., the bedside for night time monitoring, and/or a bi-directional communication device. A docking cradle may recharge a powers supply of, for example, the secondary receiver unit 2006.

Only one sensor unit 2001, data processing unit 2002 and data processing terminal 2005 are shown in the embodiment of the analyte monitoring system 2000 illustrated in FIG. 64. However, it will be appreciated by one of ordinary skill in the art that the analyte monitoring system 2000 may include more than one sensor unit 2001 and/or more than one data processing unit 2002, and/or more than one data processing terminal 2005. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 2000 may be a continuous monitoring system, or semi-continuous, or a periodic monitoring system. In a multi-component environment, each component may be configured to be uniquely identified by one or more of the other components in the system so that communication conflict may be readily resolved between the various components within the analyte monitoring system 2000. For example, unique IDs, communication channels, and the like, may be used.

In certain embodiments, the sensor unit 2001 is physically positioned in or on the body of a user whose analyte level is being monitored. The sensor unit 2001 may be configured to at least periodically sample or detect the analyte level of the user and generate a corresponding signal which may be processed by the data processing unit 2002 for transmission. The data processing unit 2002 is coupleable to the sensor unit 2001 so that both devices are positioned in or on the user's body, with at least a portion of the analyte sensor unit 2001 positioned transcutaneously. The data processing unit 2002 may include a fixation element such as adhesive or the like to secure it to the user's body. A mount (not shown) attachable to the user and mateable with the data processing unit 2002 may be used. For example, a mount may include an adhesive surface for adhering to the skin surface of the user. The data processing unit 2002 performs data processing functions, where such functions may include but are not limited to, filtering and encoding of data signals, corresponding to sampled analyte levels of the user, for transmission to the primary receiver unit 2004 via the communication link 2003. In one embodiment, the sensor 2001 or the data processing unit 2002 or a combined sensor/data processing unit may be wholly implantable under the skin layer of the user.

In certain embodiments, the primary receiver unit 2004 may include an RF receiver and an antenna that is configured to communicate with the data processing unit 2002 via the communication link 2003, and a data processing section for processing the received data from the data processing unit 2002 including data decoding, error detection and correction, data clock generation, data bit recovery, etc., or any combination thereof.

In operation, the primary receiver unit 2004 in certain embodiments is configured to synchronize with the data processing unit 2002 to uniquely identify the data processing unit 2002, based on, for example, an identification information of the data processing unit 2002, and thereafter, to periodically receive signals transmitted from the data processing unit 2002 associated with the monitored analyte levels detected by the sensor 2001.

Referring again to FIG. 64, the data processing terminal 2005 may include a personal computer, a portable computer including a laptop or a handheld device (e.g., personal digital assistants (PDAs), telephone including a cellular phone (e.g., a multimedia and Internet-enabled mobile phone including an iPhone™, a Palm based mobile telephone, a Blackberry® device, or similar communication device), mp3 player, pager, iPOD™ and the like), drug delivery device, each of which may be configured for data communication with the receiver via a wired or a wireless connection. Additionally, the data processing terminal 2005 may further be connected to a data network (not shown) for storing, retrieving, updating, and/or analyzing data corresponding to the detected analyte level of the user. The data processing terminal 2005 may include an infusion device such as an insulin infusion pump or the like, which may be configured to administer insulin to patients, and which may be configured to communicate with the primary receiver unit 2004 for receiving, among others, the measured analyte level. Alternatively, the primary receiver unit 2004 may be configured to integrate an infusion device therein so that the primary receiver unit 2004 is configured to administer insulin (or other appropriate drug) therapy to patients, for example, for administering and modifying basal profiles, as well as for determining appropriate boluses for administration based on, among others, the detected analyte levels received from the data processing unit 2002. An infusion device may be an external device or an internal device (wholly implantable in a user).

In certain embodiments, the data processing terminal 2005, which may include an insulin pump, may be configured to receive the analyte signals from the data processing unit 2002, and thus, incorporate the functions of the primary receiver unit 2004 including data processing for managing the patient's insulin therapy and analyte monitoring. In certain embodiments, the communication link 2003 as well as one or more of the other communication interfaces shown in FIG. 64, may use one or more of: an RF communication protocol, an infrared communication protocol, a Bluetooth enabled communication protocol, an 802.1x wireless communication protocol, or an equivalent wireless communication protocol which would allow secure, wireless communication of several units (for example, per HIPPA requirements), while avoiding potential data collision and interference.

Figure 65:
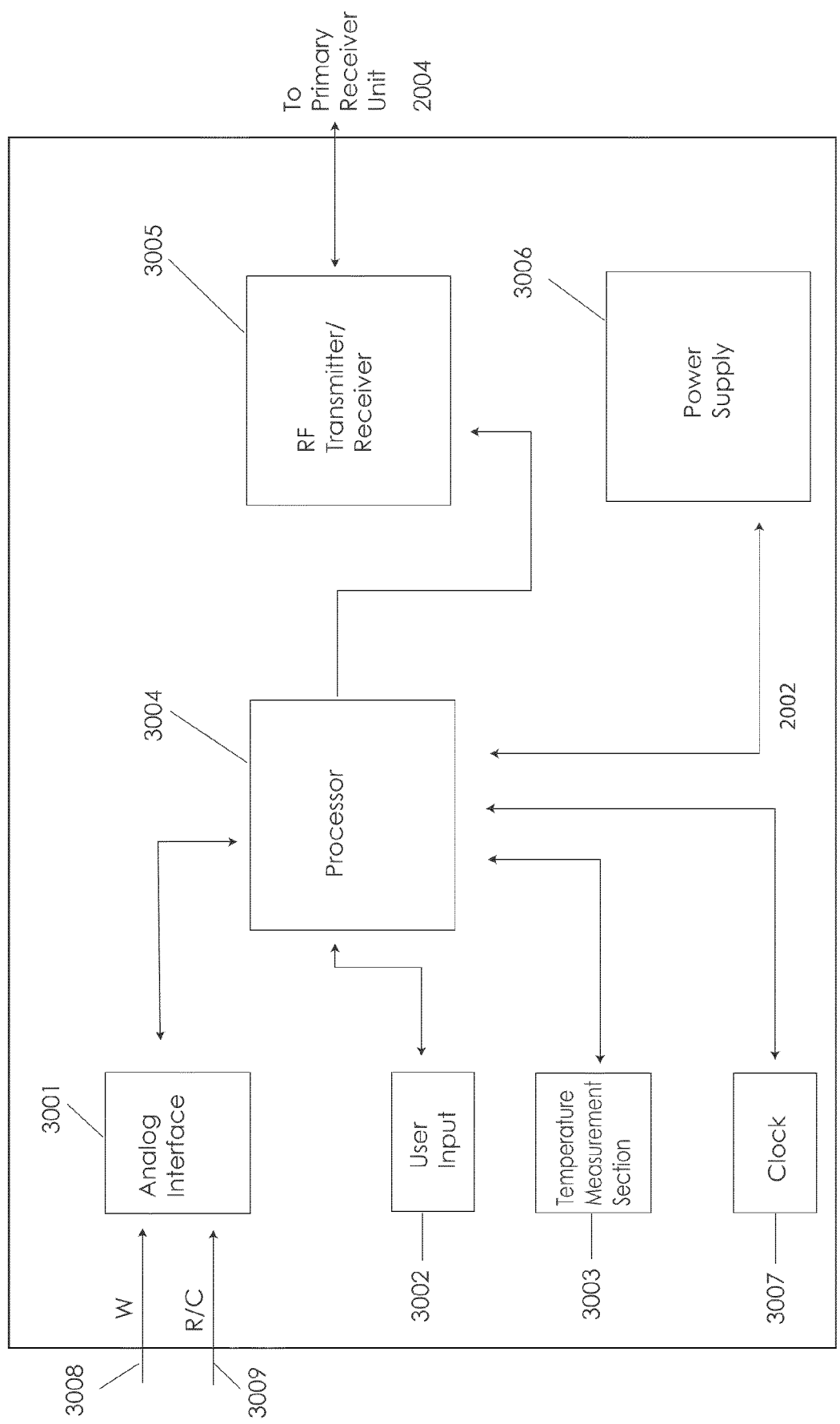
FIG. 65 shows a block diagram of an embodiment of a data processing unit of the data monitoring and management system shown in FIG. 64.

FIG. 65 shows a block diagram of an embodiment of a data processing unit 2002 of the data monitoring and detection system 2000 shown in FIG. 64. User input and/or interface components 3002 may optionally be included or a data processing unit 2002 may be free of user input and/or interface components. In certain embodiments, one or more application-specific integrated circuits (ASIC) may be used to implement one or more functions or routines associated with the operations of the data processing unit 2002. The data processing unit 2002 includes one or more of: a user input 3002, an RF transmitter/receiver 3005, a temperature measurement section 3003, a clock 3007, and a power supply 3006, each of which is operatively coupled to a processor 3004.

As can be seen in the embodiment of FIG. 65, the sensor unit 2001 (FIG. 64) includes two electrodes—working electrode (W) 3008, and reference/counter electrode (R/C) 3009, each operatively coupled to the analog interface 3001 of the data processing unit 2002. Fewer or greater electrodes may be employed. For example, there may be more than one working electrode and/or reference/counter electrode, etc.

Figure 66:
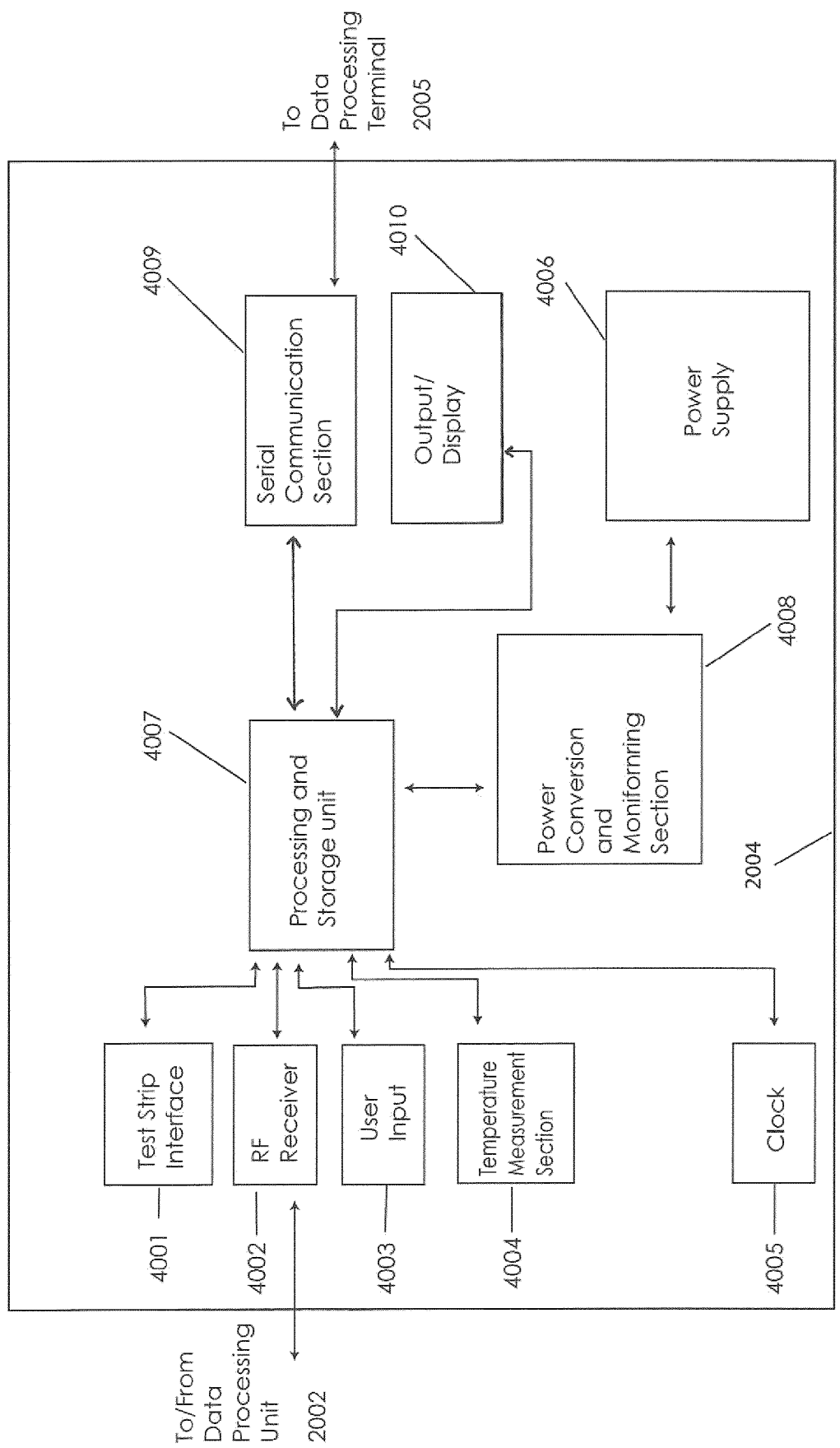
FIG. 66 shows a block diagram of an embodiment the primary receiver unit of the data monitoring and management system shown in FIG. 64.

FIG. 66 is a block diagram of an embodiment of a receiver unit such as the primary receiver unit 2004 of the data monitoring and management system shown in FIG. 64. The primary receiver unit 2004 includes one or more of: a blood glucose test strip interface 4001, an RF receiver 4002, a user input 4003, a temperature measurement section 4004, and a clock 4005, each of which is operatively coupled to a processing and storage section 4007. The primary receiver unit 2004 also includes a power supply 4006 operatively coupled to a power conversion and monitoring section 4008. Further, the power conversion and monitoring section 4008 is also coupled to the processing and storage unit 4007. Moreover, also shown are a receiver serial communication section 4009, and an output/display 4010, each operatively coupled to the processing and storage unit 4007. The receiver may include user input and/or interface components or may be free of user input and/or interface components.

In certain embodiments, the test strip interface 4001 includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output/display 4010 of the primary receiver unit 2004. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® blood glucose test strips from Abbott Diabetes Care Inc. The terms "test strip" and "glucose test strip" are used here for convenience. However, it should be noted that analyte sensors having extruded electrode structures in a variety of configurations as described herein, e.g., tubular or cylindrical configurations, can be configured to interface with the test strip interface of the primary receiver unit 2004. Glucose information obtained by the in vitro glucose testing device may be used for a variety of purposes, computations, etc. For example, the information may be used to calibrate sensor unit 2001 (FIG. 64), confirm results of the sensor unit 2001 to increase the confidence thereof (e.g., in instances in which information obtained by sensor 2001 is employed in therapy related decisions), etc.

In further embodiments, the data processing unit 2002 (FIG. 64) and/or the primary receiver unit 2004 (FIG. 64) and/or the secondary receiver unit 2006 (FIG. 64), and/or the data processing terminal/infusion section 2005 (FIG. 64) may be configured to receive the blood glucose value wirelessly over a communication link from, for example, a blood glucose meter. In further embodiments, a user manipulating or using the analyte monitoring system 2000 (FIG. 64) may manually input the blood glucose value using, for example, a user interface (e.g., a keyboard, keypad, voice commands, and the like) incorporated in one or more of the data processing unit 2002, the primary receiver unit 2004, the secondary receiver unit 2006, or the data processing terminal/infusion section 2005.

Additional detailed descriptions are provided in U.S. Pat. Nos. 5,262,035; 5,262,305; 5,264,104; 5,262,305; 5,320,715; 5,593,852; 6,103,033; 6,134,461; 6,175,752; 6,560,471; 6,579,690; 6,605,200; 6,654,625; 6,746,582; 6,932,894; 6,284,478; 7,299,082; and in U.S. Patent Application Publication Nos. 2004/0186365 and 2004/0186365, the disclosures of each of which are herein incorporated by reference.

Sensor Control Unit

Where the extruded electrode structures of the present disclosure are configured to operate as in vivo analyte sensors, they can be configured to operate with one or more sensor control units. The sensor can be integrated in the sensor control unit, part or all of which may be subcutaneously implanted or it can be configured to be placed on the skin of a patient. The sensor control unit is optionally formed in a shape that is comfortable to the patient and which may permit concealment, for example, under a patient's clothing. The thigh, leg, upper arm, shoulder, and abdomen are convenient parts of the patient's body for placement of the sensor control unit to maintain concealment. However, the sensor control unit may be positioned on other portions of the patient's body. One embodiment of the sensor control unit has a thin, oval shape to enhance concealment. However, other shapes and sizes may be used.

The particular profile, as well as the height, width, length, weight, and volume of the sensor control unit may vary and depends, at least in part, on the components and associated functions included in the sensor control unit. In general, the sensor control unit includes a housing typically formed as a single integral unit that rests on the skin of the patient. The housing typically contains most or all of the electronic components of the sensor control unit.

The housing of the sensor control unit may be formed using a variety of materials, including, for example, plastic and polymeric materials, particularly rigid thermoplastics and engineering thermoplastics. Suitable materials include, for example, polyvinyl chloride, polyethylene, polypropylene, polystyrene, ABS polymers, and copolymers thereof. The housing of the sensor control unit may be formed using a variety of techniques including, for example, injection molding, compression molding, casting, and other molding methods. Hollow or recessed regions may be formed in the housing of the sensor control unit. The electronic components of the sensor control unit and/or other items, including a battery or a speaker for an audible alarm, may be placed in the hollow or recessed areas.

The sensor control unit is typically attached to the skin of the patient, for example, by adhering the sensor control unit directly to the skin of the patient with an adhesive provided on at least a portion of the housing of the sensor control unit which contacts the skin or by suturing the sensor control unit to the skin through suture openings in the sensor control unit.

When positioned on the skin of a patient, the sensor and the electronic components within the sensor control unit are coupled via conductive contacts. The working electrode and reference/counter electrode are attached to individual conductive contacts. For example, the conductive contacts can be provided on the interior of the sensor control unit. Other embodiments of the sensor control unit have the conductive contacts disposed on the exterior of the housing. The placement of the conductive contacts is such that they are in contact with the conductive contacts on the sensor when the sensor is properly positioned within the sensor control unit.

Sensor Control Unit Electronics

The sensor control unit also typically includes at least a portion of the electronic components that make up the analyte monitoring system. The electronic components of the sensor control unit typically include a power supply for operating the sensor control unit, a sensor circuit for obtaining signals from the sensor, a measurement circuit that converts sensor signals to a desired format, and a processing circuit that, at minimum, obtains signals from the sensor circuit and/or measurement circuit and provides the signals to an optional receiver. In some embodiments, the processing circuit may also partially or completely evaluate the signals from the sensor and convey the resulting data to the optional receiver and/or activate an optional alarm system if the analyte level exceeds a threshold. The processing circuit often includes analog and/or digital logic circuitry.

The sensor control unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

Moreover, the sensor control unit may also include digital and/or analog components utilizing semiconductor devices, including transistors. To operate these semiconductor devices, the sensor control unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Calibration

Sensors may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for calibration may be determined by the system on a real-time basis according to various factors, including, but not limited to, glucose concentration and/or temperature and/or rate of change of glucose, etc.

In addition to a transmitter, an optional receiver may be included in the sensor control unit. In some cases, the transmitter is a transceiver, operating as both a transmitter and a receiver. The receiver may be used to receive calibration data for the sensor. The calibration data may be used by the processing circuit to correct signals from the sensor. This calibration data may be transmitted by the receiver/display unit or from some other source such as a control unit in a doctor's office. In addition, the optional receiver may be used to receive a signal from the receiver/display units to direct the transmitter, for example, to change frequencies or frequency bands, to activate or deactivate the optional alarm system and/or to direct the transmitter to transmit at a higher rate.

Calibration data may be obtained in a variety of ways. For instance, the calibration data may simply be factory-determined calibration measurements which can be input into the sensor control unit using the receiver or may alternatively be stored in a calibration data storage unit within the sensor control unit itself (in which case a receiver may not be needed). The calibration data storage unit may be, for example, a readable or readable/writeable memory circuit.

Calibration may be accomplished using an in vitro test strip (or other reference), e.g., a small sample test strip such as a test strip that requires less than about 1 microliter of sample (e.g., FreeStyle® blood glucose monitoring test strips from Abbott Diabetes Care). In some embodiments, test strips that require less than about 1 nanoliter of sample may be used. In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

Alternative or additional calibration data may be provided based on tests performed by a doctor or some other professional or by the patient. For example, it is common for diabetic individuals to determine their own blood glucose concentration using commercially available testing kits. The results of this test is input into the sensor control unit either directly, if an appropriate input device (e.g., a keypad, an optical signal receiver, or a port for connection to a keypad or computer) is incorporated in the sensor control unit, or indirectly by inputting the calibration data into the receiver/display unit and transmitting the calibration data to the sensor control unit.

Other methods of independently determining analyte levels may also be used to obtain calibration data. This type of calibration data may supplant or supplement factory-determined calibration values.

In some embodiments of the invention, calibration data may be required at periodic intervals, for example, every eight hours, once a day, or once a week, to confirm that accurate analyte levels are being reported. Calibration may also be required each time a new sensor is implanted or if the sensor exceeds a threshold minimum or maximum value or if the rate of change in the sensor signal exceeds a threshold value. In some cases, it may be necessary to wait a period of time after the implantation of the sensor before calibrating to allow the sensor to achieve equilibrium. In some embodiments, the sensor is calibrated only after it has been inserted. In other embodiments, no calibration of the sensor is needed. Exemplary calibration protocols are described, e.g., in U.S. Pat. No. 7,299,082, the disclosure of which is herein incorporated by reference.

Analyte Monitoring Device

In some embodiments, the present disclosure provides an analyte monitoring device which includes a sensor control unit such as, for example, the data processing unit 2002 (FIG. 64) and an analyte sensor with an extruded electrode structure as described herein. In some embodiments, the processing circuit of the sensor control unit is able to determine a level of the analyte and activate an alarm system if the analyte level exceeds a threshold. The sensor control unit, in these embodiments, has an alarm system and may also include a display, such as an LCD or LED display. Alternatively, a similar alarm system may be provided in the receiver unit in signal communication with the sensor control unit.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the patient has entered a hyperglycemic state. As another example, a datapoint which correlates to a glucose level of 65 mg/dL exceeds a threshold value for hypoglycemia of 70 mg/dL because the datapoint indicates that the patient is hypoglycemic as defined by the threshold value. However, a datapoint which correlates to a glucose level of 75 mg/dL would not exceed the same threshold value for hypoglycemia because the datapoint does not indicate that particular condition as defined by the chosen threshold value.

An alarm may also be activated if the sensor readings indicate a value that is beyond a measurement range of the sensor. For glucose, the physiologically relevant measurement range is typically about 30 to 500 mg/dL, including about 40-300 mg/dL and about 50-250 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Dosage Calculation Function

In some embodiments, the analyte monitoring device is configured to perform medication dosage calculation functions, such as a single-dose calculation function for injection of rapid acting insulin and/or long acting insulin. Analyte meters which include medication dosage calculation functions and methods of performing the dosage calculation functions are described, for example, in U.S. patent application Ser. No. 11/396,182, filed Mar. 31, 2006, titled "Analyte Monitoring Devices and Methods Therefor," the disclosure of which is incorporated by reference herein.

In one embodiment, the analyte monitoring device is configured to perform a bolus calculation function. For example, the analyte monitoring device may be configured to determine a bolus dosage, e.g., an insulin bolus dosage, based on the signal received from the analyte sensor.

Drug Delivery System

The present disclosure also provides sensor-based drug delivery systems utilizing the analyte sensors described herein. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Additional information regarding integrated medication delivery devices or systems is provided, for example, in U.S. Patent Publication No. US2006/0224141, published on Oct. 5, 2006, titled "Method and System for Providing Integrated Medication Infusion and Analyte Monitoring System", and U.S. Patent Publication No. US2004/0254434, published on Dec. 16, 2004, titled "Glucose Measuring Module and Insulin Pump Combination," the disclosure of each of which is incorporated by reference herein.

Method of Making Extruded Electrode Structures and Analyte Sensors

The extruded electrode structures described herein can be prepared through the application of extrusion techniques which are well known in the art. In one embodiment, an electrode structure according to the present disclosure is produced by pushing or drawing heterogeneous material containing a dielectric material and one or more conductive materials, e.g., a dielectric polymer which includes one or more conductive stripes, through a die having a desired cross-section. In some embodiments, the material to be extruded can be heated prior to and/or during the extrusion process. Electrode structures having a first conductive material, a second conductive material, and a dielectric material can be coextruded in this manner to provide an electrode structure having the first conductive material and the second conductive material electrically isolated by the dielectric material.

Figure 36:
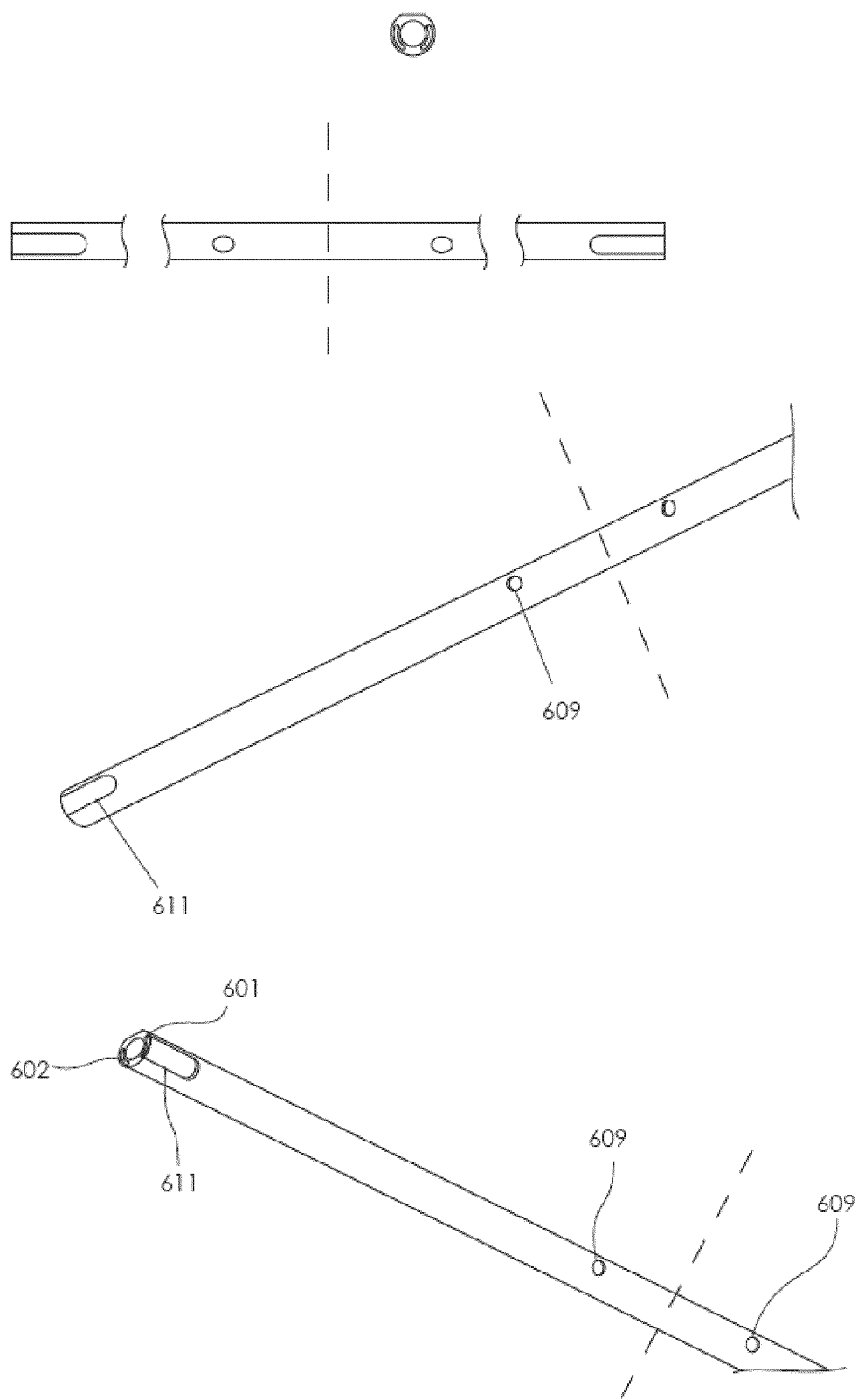
FIG. 36 shows three different views of a hollow electrode structure which can be extruded as a unitary structure, modified with optional cutout regions, and cut to produce multiple electrode structures.
Figure 37:
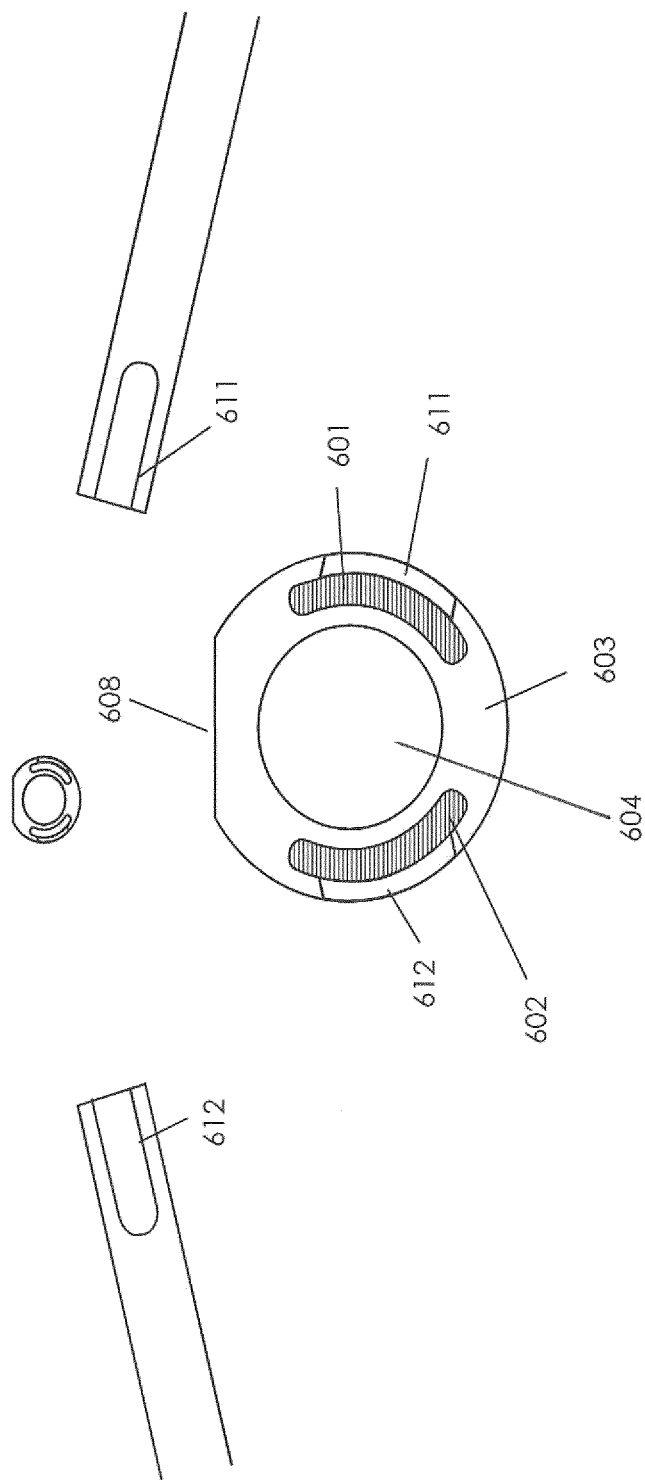
FIG. 37 shows views of the connection end of the hollow electrode structure shown in FIG. 36, including a cross-sectional view.
Figure 38:
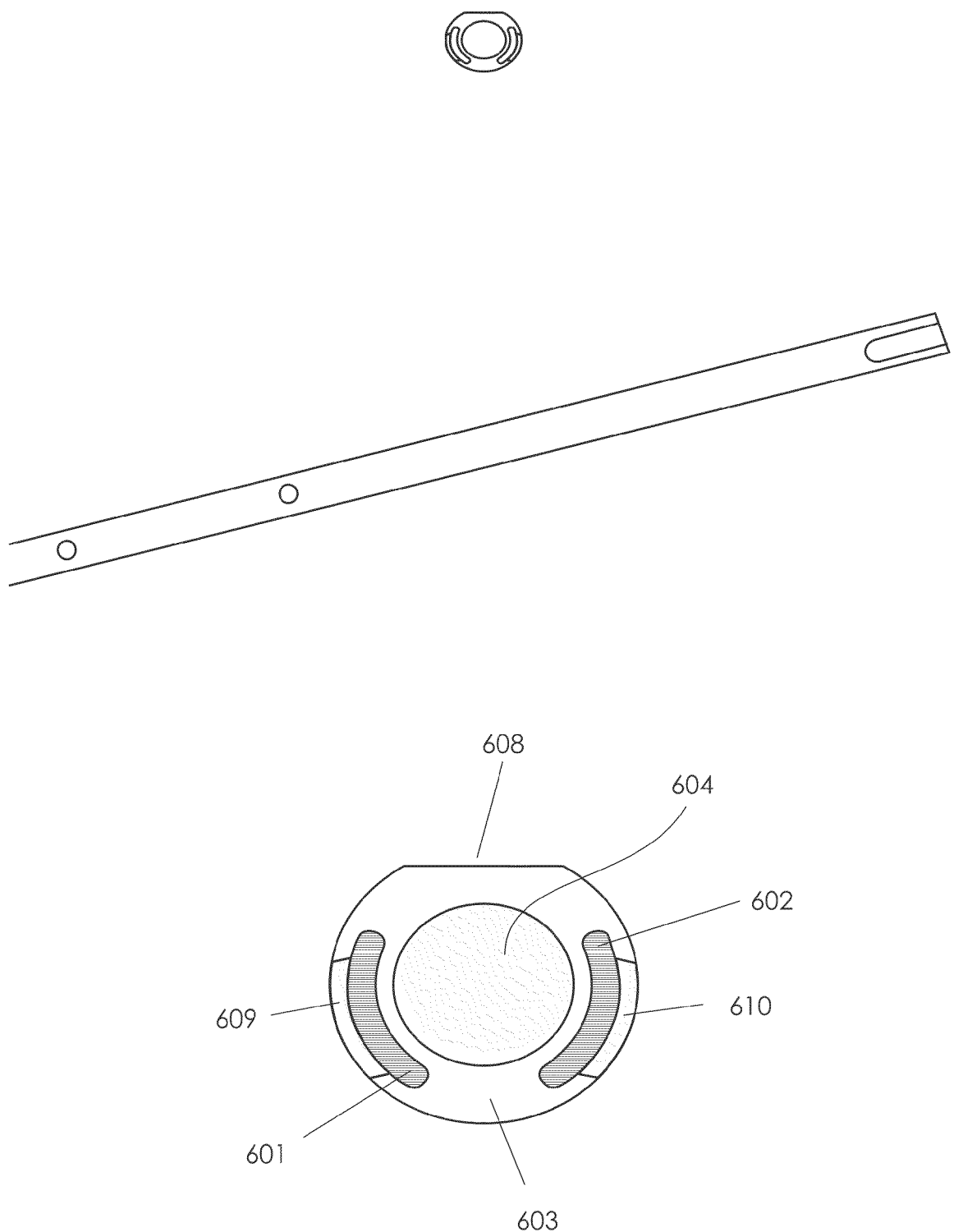
FIG. 38 shows views of the sensor end of the hollow electrode structure shown in FIG. 36, including a cross-sectional view.

A variety of shapes and sizes of electrode structures can be produced using these methods, including, but not limited to, those with solid, hollow, tubular, and/or rectangular box configurations as described previously herein. Extruded structures according to the present disclosure can be extruded individually (e.g., FIG. 33) or alternatively an extruded electrode structure precursor can be produced which is then cut to the appropriate size to produce multiple electrode structures (e.g., an extruded electrode structure precursor as shown in FIG. 36 can be cut along the dashed lines indicated in FIG. 36 to produce two extruded electrode structures).

In some embodiments, subsequent to extrusion, the electrode structures are modified via skiving, drilling, cutting, laser processing, or other suitable method or combination thereof to expose one or more of the conductive materials. For example, one or more of these methods can be used to remove portions of the dielectric material so as to expose portions of one or both of the first conductive material and the second conductive material. Where an extruded electrode structure precursor is produced and then cut to produce multiple electrode structures, modification to expose one or more of the conductive materials can occur before, during, or after the precursor is cut to produce multiple electrode structures. Exposure of one or more of the conductive materials allows for deposition of sensing chemistry, e.g., to produce one or more working electrodes; or modification of the electrode structure for electrical connection with a connector, device, and/or additional electrode structure. An embodiment of a modified electrode structure which has been configured for electrical connection to a connector is shown, e.g., in FIGS. 40 and 41.

As an alternative to the deposition of sensing chemistry to produce one or more working electrodes, suitable sensing chemistry can be incorporated in, and extruded along with, one or more of the conductive materials, such that the coextruded structure contains one or more working electrodes without the need for subsequent sensing chemistry deposition. For example, sensing chemistry elements may be cross-linked to a conductive polymer, which, once extruded, provides an extruded working electrode.

In one embodiment, where an extruded electrode structure is to be configured as an analyte sensor, material used to configure a conductive material as a reference/counter electrode, e.g., Ag/AgCl, is incorporated in, and coextruded along with, the conductive material during production of the extruded electrode structure. This can help to avoid subsequent steps as it obviates any need to add reference/counter electrode material, e.g., Ag/AgCl, to the electrode structure subsequent to the extrusion process. For example, in one embodiment an extruded electrode structure includes an extruded conductive carbon stripe blended with Ag/AgCl.

One or more membranes may be applied over the sensing chemistry of the electrode structure, e.g., to create a diffusion-limiting barrier to reduce the rate of mass transport of the analyte, for example, glucose or lactate, into the region around the working electrode. An example of this process is depicted generally in FIG. 31. In some embodiments, the membrane may be deposited as a liquid, e.g., in a dropwise manner, which subsequently solidifies forming the membrane. In such embodiments, it may be desirable to further modify the membrane by removing excess membrane material to provide a uniform membrane surface. Excess membrane may also be removed to provide a membrane layer which is flush with the dielectric material of the electrode structure. Modification of the membrane as described above can reduce variation in the diffusion characteristics between different analyte sensors or batches of analyte sensors.

In some embodiments, one or more holes can be drilled through the electrode structure, e.g., to control the total uptake volume of fluid sample or expose indicator electrode contacts as described previously herein.

For certain applications, e.g., in vitro and in vivo analyte monitoring, it will be appropriate to sterilize the electrode structures following the extrusion process. Such sterilization can be accomplished using any suitable method known in the art.

Where an extruded electrode structure is configured for use as an in vivo analyte sensor, the extruded electrode structure can optionally have an anticlotting agent disposed on a portion of the sensor which is implanted into a patient. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor that is to be implanted. The anticlotting agent may be applied, for example, by bath, spraying, brushing, or dipping. The anticlotting agent is allowed to dry on the sensor. The anticlotting agent may be immobilized on the surface of the sensor or it may be allowed to diffuse away from the sensor surface. Typically, the quantities of anticlotting agent disposed on the sensor are far below the amounts typically used for treatment of medical conditions involving blood clots and, therefore, have only a limited, localized effect.

Insertion of Electrode Structures and Analyte Sensors

As described herein, extruded electrode structures and extruded electrode structures configured as analyte sensors can include optional features to facilitate insertion of the extruded electrode structures or sensors for in vivo use. For example, the extruded electrode structures and sensors may be pointed at the tip to ease insertion. In addition, the extruded electrode structures and sensors may include a barb which assists in anchoring the extruded electrode structure or sensor within the tissue of the patient during operation of the extruded electrode structure or sensor. However, the barb is typically small enough so that little damage is caused to the subcutaneous tissue when the extruded electrode structure or sensor is removed, e.g., for replacement.

An insertion device can be used to subcutaneously insert the electrode structure or sensor into the patient. The insertion device is typically formed using structurally rigid materials, such as metal or rigid plastic. Exemplary materials include stainless steel and ABS (acrylonitrile-butadiene-styrene) plastic. In some embodiments, the insertion device is pointed and/or sharp at the tip to facilitate penetration of the skin of the patient. A sharp, thin insertion device may reduce pain felt by the patient upon insertion of the sensor. In other embodiments, the tip of the insertion device has other shapes, including a blunt or flat shape. These embodiments may be particularly useful when the insertion device does not penetrate the skin but rather serves as a structural support for the sensor as the sensor is pushed into the skin.

A variety of insertion devices and/or systems are known in the art, which can be modified for use with the extruded electrode structures and analyte sensors disclosed herein. In some embodiments, a standard infusion set used with insulin pumps may be utilized to facilitate insertion of an extruded electrode structure or analyte sensor as described herein. An additional insertion device and/or system which may be modified for use with the extruded electrode structures and analyte sensors described herein is the spring loaded insertion device used for the FreeStyle Navigator® continuous glucose monitoring system (available from Abbott Diabetes Care Inc.).

Additional information pertaining to insertion devices and/or systems and uses thereof can be found in U.S. Pat. Nos. 6,071,391; 6,103,033; 6,175,752; 6,329,161; 6,484,046; 6,560,471; 6,565,509, 6,973,706; 6,990,366; 7,003,340; 7,003,341; and 7,381,184, the disclosures of each of which are incorporated by reference herein.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Linearity Study Using Extruded Pebax® Working Electrode

A linearity study was conducted using an extruded Pebax® working electrode, a screen printed carbon counter electrode and a screen printed Ag/AgCl reference electrode. A testing station with LC-3D p-stats was used to test the electrodes. The extruded working electrode was paired through a potentiostat with the Ag/AgCl reference and carbon counter electrodes. Testing was carried out in 1000 ml PBS at 37° C. and $\Delta E=+40$ mV. Glucose aliquots were added to produce concentrations of 1, 5, 10, and 20 mM, at various time points as evident from the humps in FIG. 67.

Two different sensing layers were utilized: A control sensing layer (PBX_C) 5% glucose oxidase sensing layer solution and a test sensing layer (PBX_M) 5% glucose oxidase sensing layer solution, 5% carbon nanopowder, 1% Triton X100. The respective sensing layers were deposited manually using a 0.5 µl syringe, 15 nL per working electrode. The two sensing layers were tested in groups of four replicates each.

A PVP membrane (poly(vinylpyridine), 130 mg/ml) was coated over the applied sensing layers by dipping the sensor tip into a membrane solution bath twice with a 10-minute interval and 5 mm/sec exit velocity. Extruded Pebax® tubing having a diameter of 0.012 inches and a resistance of ~35 kΩ per inch was utilized in the preparation of the working electrodes.

Figure 67:
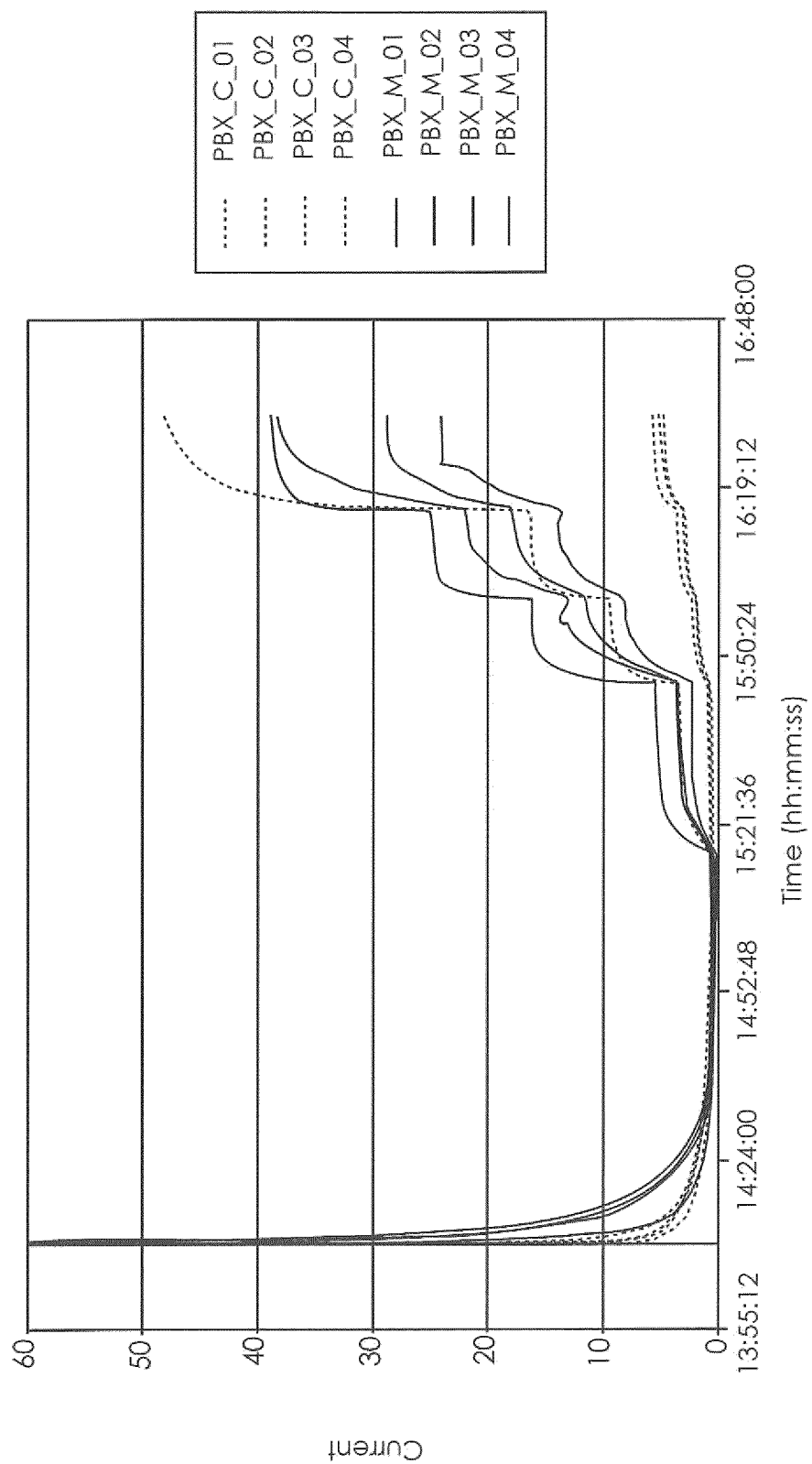
FIG. 67 is a raw linearity chart showing the results of linearity testing on extruded Pebax® working electrodes.
Figure 68:
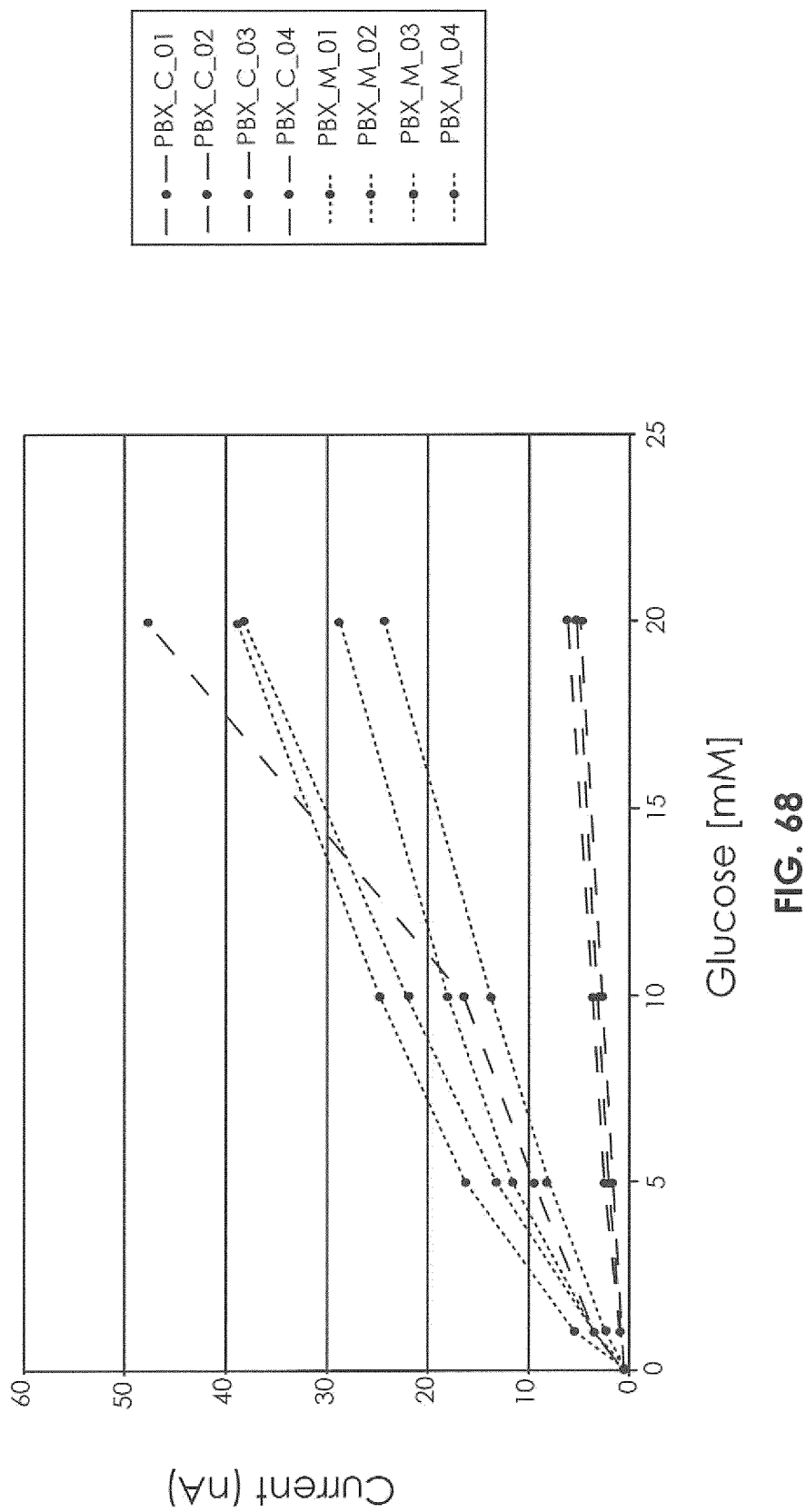
FIG. 68 shows a graphical representation of the results of linearity testing on extruded Pebax® working electrodes.

The extruded electrode structures were exposed to varying glucose concentrations (0, 1, 5, 10, and 20 mM) at varying time points and current (nA) was measured using a 4.67 Mohm resistor. FIG. 67 shows a raw linearity chart (current nA vs. time), and FIG. 68 shows a linearity chart with current (nA) vs. glucose concentration in mM. The test sensors having 5% glucose oxidase sensing layer solution, 5% carbon nanopowder and 1% Triton X100 showed higher sensitivity (~1.6 nA/mM) than the control sensors (~0.23 nA/mM). It should be noted that one of the control sensors resulted in higher sensitivity due to fractures in the PVP membrane and was therefore excluded from the sensitivity measurement. The test sensors also showed faster response time than the control sensors.

These results demonstrate that an extruded electrode structure is capable of producing a sensitive and substantially linear response to changing glucose concentration. Furthermore, sensitivity was increased with the addition of 5% carbon nanopowder and 1% Triton X100 to the sensing layer.

Example 2

Stability Study Using Extruded Pebax® Working Electrode

Figure 69:
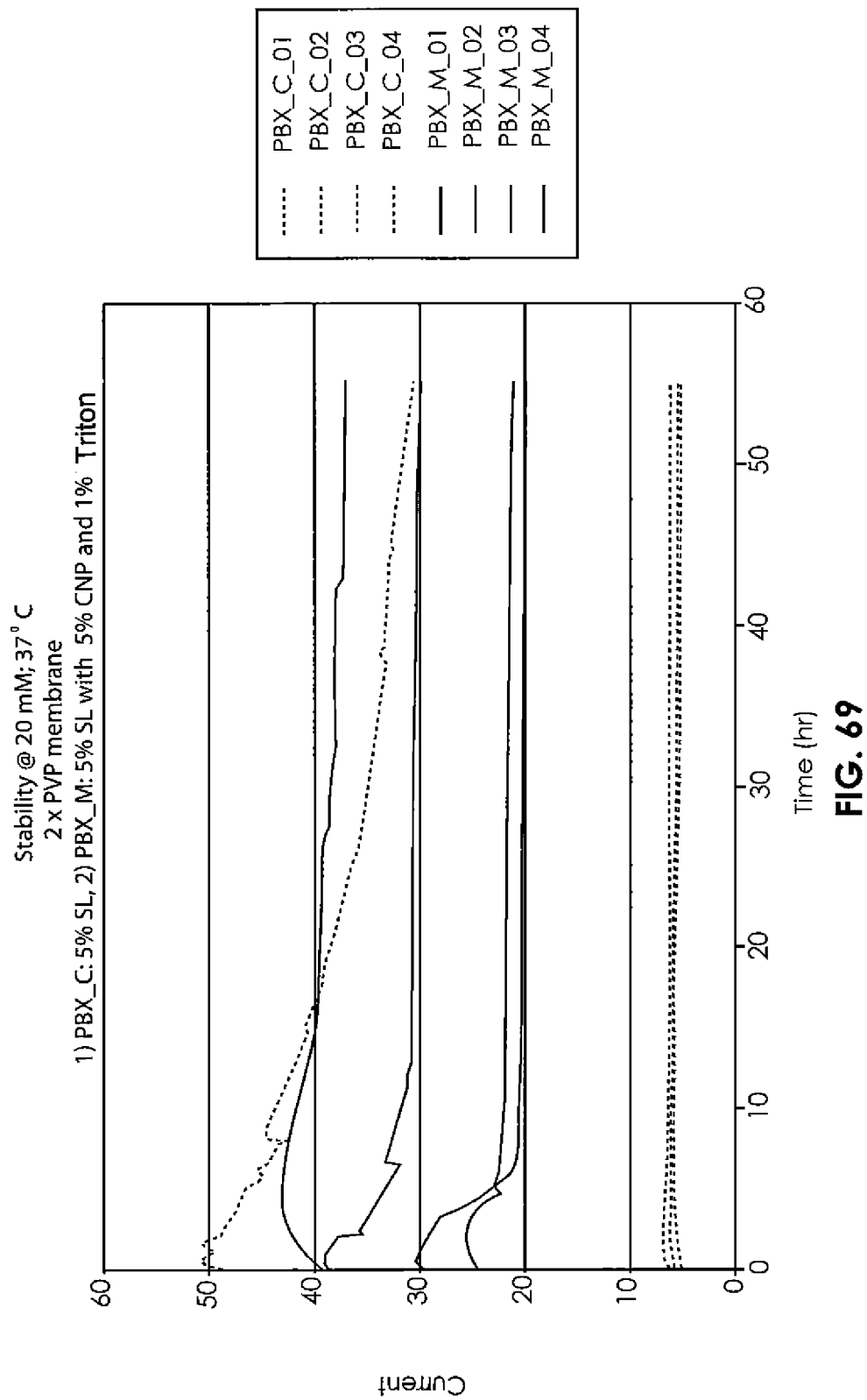
FIG. 69 shows graphical results of stability testing on extruded Pebax® working electrodes.

A stability study was conducted using an extruded Pebax® working electrode, a screen printed counter electrode and a screen printed Ag/AgCl reference electrode. Materials and methods were as described for Example 1, with the exception that the electrode structures were tested at a constant glucose concentration of 20 mM. FIG. 69 shows the results of the stability study. Less variation in the current (0.08% per hr) was seen for the control sensors relative to the test sensors. As with Example 1, data for the control sensor with fractures in the PVP membrane were excluded from the stability study. These results demonstrate that an extruded electrode structure is capable of producing a substantially stable response to glucose concentration.

Example 3

Resistivity of Blended Conductive Polymer Materials

FIG. 70 provides a table which shows the results of resistivity measurements for three conductive polymer materials with different percentages of carbon blending. Pebax® polymer blended with 7, 10 or 13% carbon black were cut into small strips from casted plaques having a thickness of ~1 mm. Strips were cut to the size of standard FreeStyle® test strips. Both ends of each strip were tightly inserted into a gold-plated female connector for stable connection. Resistance was measured across the connectors using a Fluke® multimeter. Using the measured resistance values, resistivity values were determined for each of the carbon-blended polymers.

Pebax® polymers having 7, 10, and 13% carbon black had mean resistivity values of 21.6, 6.3, and 4.9 respectively, with mean resistivity values of 6.3 and 4.9 falling within an acceptable range for electrodes. As such, Pebax® polymers having 10% and 13% carbon black had mean resistivity values indicating that these materials were suitable for use as electrodes.

Example 4

Cyclic Voltammetry for Blended Conductive Polymer Materials

Figure 71:
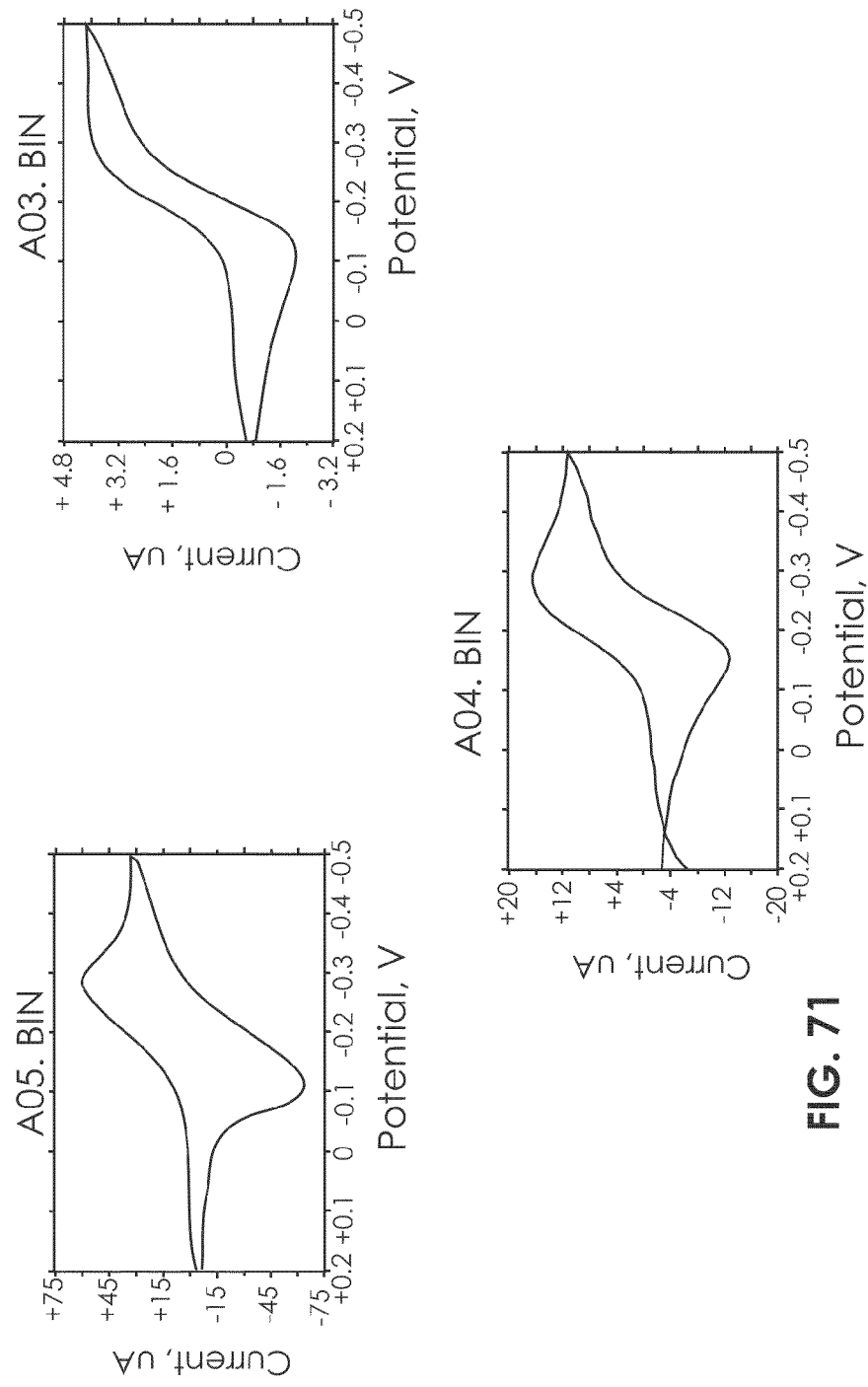
FIG. 71 shows cyclic voltammetric graphs for the conductive materials used in FreeStyle® strips and the conductive materials used in two conductive polymers.

FIG. 71 compares cyclic voltammetric graphs of the conductive material used in FreeStyle® test strips (A05), Pebax® polymer blended with 7% carbon black (A03), and Pebax® polymer blended with 13% carbon black (A04).

Strips of the carbon-blended polymers were cut from casted plaques having a thickness of ~1 mm. Strips were cut to the size of standard FreeStyle® test strips and tested in phosphate buffered saline (PBS) with standard individual counter and reference electrodes.

The results indicate that the electrochemical properties of the 13% carbon blended conductive polymer are similar to the carbon material used in currently available FreeStyle® test strips.

Example 5

Resistivity and Extrusion Temperature Testing for Extruded Carbon-Blended Pebax® Polymers In order to determine whether extruded conductive polymers would be suitable for use as electrodes, resistivity values for extruded carbon-blended polymer were determined. Strings of carbon-blended Pebax® polymer having 7, 10, and 13% carbon black were extruded on two different days. An extrusion temperature of 220±2° C. was used. Resistance was measured using a Fluke® multimeter and mean resistivity was calculated. The results of these experiments are provided below in Tables 1-6.

TABLE 1

| Raw Material Extrusion Temp | PEBAX (7% Carbon Black) 220 ± 2° C. #1 | #2 | #3 | #4 | Mean Resistivity |
|---|---|---|---|---|---|
| Diameter (cm) | 0.0258 | 0.0233 | 0.0268 | 0.0226 | |
| Length (cm) | 284 | 291 | 223 | 351 | |

TABLE 1-continued

| Raw Material Extrusion Temp | PEBAX (7% Carbon Black) 220 ± 2° C. #1 | #2 | #3 | #4 | Mean Resistivity |
|---|---|---|---|---|---|
| Resistance (MΩ) | 8.870 | 10.540 | 6.07 | 13.06 | |
| Resistivity (Ω · cm) | 16.35 | 15.41 | 15.33 | 14.95 | 15.51 |

TABLE 2

| Raw Material Extrusion Temp | PEBAX (7% Carbon Black) 220 ± 2° C. #1 | #2 | #3 | #4 | #5 | Mean Resistivity |
|---|---|---|---|---|---|---|
| Diameter (cm) | 0.0516 | 0.0472 | 0.0510 | 0.0480 | 0.0518 | |
| Length (cm) | 48.5 | 27 | 92.5 | 70.5 | 57.5 | |
| Resistance (MΩ) | 0.322 | 0.161 | 0.500 | 0.463 | 0.302 | |
| Resistivity (Ω · cm) | 13.87 | 10.45 | 11.04 | 11.89 | 11.05 | 11.66 |

TABLE 3

| Raw Material Extrusion Temp | PEBAX (10% Carbon Black) 220 ± 2° C. #1 | #2 | #3 | #4 | Mean Resistivity |
|---|---|---|---|---|---|
| Diameter (cm) | 0.0265 | 0.0265 | 0.0269 | 0.0274 | |
| Length (cm) | 233 | 217 | 303 | 288 | |
| Resistance (MΩ) | 0.918 | 0.860 | 1.182 | 1.104 | |
| Resistivity (Ω · cm) | 2.17 | 2.19 | 2.22 | 2.25 | 2.21 |

TABLE 4

| Raw Material Extrusion Temp | PEBAX (10% Carbon Black) 220 ± 2° C. #1 | #2 | #3 | #4 | #5 | Mean Resistivity |
|---|---|---|---|---|---|---|
| Diameter (cm) | 0.05 | 0.05 | 0.0513 | 0.0510 | 0.0477 | |
| Length (cm) | 85 | 93.5 | 73.5 | 94 | 63 | |
| Resistance (MΩ) | 0.0832 | 0.093 | 0.0826 | 0.0916 | 0.0756 | |
| Resistivity (Ω · cm) | 1.92 | 1.94 | 2.32 | 1.99 | 2.15 | 2.06 |

TABLE 5

| Raw Material Extrusion Temp | PEBAX (13% Carbon Black) 220 ± 2° C. #1 | #2 | #3 | Mean Resistivity |
|---|---|---|---|---|
| Diameter (cm) | 0.0206 | 0.0218 | 0.0223 | |
| Length (cm) | 194 | 370 | 260 | |
| Resistance (MΩ) | 2.395 | 4.302 | 3.232 | |
| Resistivity (Ω · cm) | 4.12 | 4.36 | 4.86 | 4.45 |

TABLE 6

| Raw Material Extrusion Temp | PEBAX (13% Carbon Black) 220 ± 2° C. #1 | #2 | #3 | #4 | #5 | Mean Resistivity |
|---|---|---|---|---|---|---|
| Diameter (cm) | 0.0519 | 0.0522 | 0.0519 | 0.0510 | 0.0515 | |
| Length (cm) | 92 | 84 | 92 | 96 | 88 | |
| Resistance (MΩ) | 0.189 | 0.168 | 0.193 | 0.1953 | 0.1857 | |
| Resistivity (Ω · cm) | 4.34 | 4.27 | 4.43 | 4.16 | 4.40 | 4.32 |

The results shown in Tables 1-6 indicate that mean resistivity values for extruded carbon-blended Pebax® polymers having 10% and 13% carbon black are within an acceptable range for use as electrodes (e.g., less than 12 cm.Ω).

The effects of extrusion temperature variation on the resistivity of carbon-blended Pebax® polymers having 10% and 13% carbon black were also determined. The results of these experiments are provided below in Tables 7 and 8.

TABLE 7

| Sample Name | Carbon Black Ratio (%) | Dimension (cm) Length | Diameter | Resistance (KΩ) | Resistivity (Ω · cm) | Extrusion Temp. (° F.) | (° C.) | Mean Resistivity |
|---|---|---|---|---|---|---|---|---|
| 10% Carbon Black | 10 | 64 | 0.022 | 7580 | 45.0 | 280 | 138 | |
| | 10 | 64.2 | 0.022 | 7640 | 45.2 | 280 | 138 | 39.9 |
| | 10 | 61.2 | 0.022 | 4737 | 29.4 | 265 | 129 | |
| 10% Carbon Black | 10 | 73.9 | 0.022 | 3041 | 15.6 | 295 | 146 | |
| | 10 | 59.2 | 0.022 | 1818 | 11.7 | 308 | 153 | 13.0 |
| | 10 | 72 | 0.022 | 2199 | 11.6 | 308 | 153 | |
| 10% Carbon Black | 10 | 77.5 | 0.022 | 502.4 | 2.5 | 350 | 177 | |
| | 10 | 85.7 | 0.022 | 564 | 2.5 | 350 | 177 | 2.5 |
| | 10 | 37.2 | 0.022 | 247.9 | 2.5 | 350 | 177 | |
| 10% Carbon Black | 10 | 62.8 | 0.022 | 374.3 | 2.3 | 450 | 232 | |
| | 10 | 80.8 | 0.022 | 443.8 | 2.1 | 450 | 232 | 2.2 |
| | 10 | 51.6 | 0.022 | 301.6 | 2.2 | 450 | 232 | |
| | 10 | 72.8 | 0.022 | 449.3 | 2.3 | 450 | 232 | |

TABLE 8

| Sample Name | Carbon Black Ratio (%) | Dimension (cm) Length | Diameter | Resistance (KΩ) | Resistivity (Ω · cm) | Extrusion temperature (° F.) | (° C.) | Mean Resistivity |
|---|---|---|---|---|---|---|---|---|
| 13% Carbon Black | 13 | 6.5 | 0.022 | 39630 | 2317.6 | 270 | 132 | |
| | 13 | 5.2 | 0.022 | 38550 | 2818.1 | 260 | 127 | 1862.2 |
| | 13 | 14.6 | 0.022 | 41360 | 1076.9 | 280 | 138 | |
| | 13 | 15.5 | 0.022 | 50410 | 1236.3 | 280 | 138 | |
| 13% Carbon Black | 13 | 63.3 | 0.022 | 52640 | 316.1 | 298 | 148 | |
| | 13 | 35.3 | 0.022 | 33100 | 356.4 | 298 | 148 | 347.7 |
| | 13 | 48.7 | 0.022 | 47480 | 370.6 | 298 | 148 | |
| 13% Carbon Black | 13 | 65.5 | 0.022 | 1267 | 7.4 | 350 | 177 | |
| | 13 | 65.5 | 0.022 | 1418 | 8.2 | 350 | 177 | 7.6 |
| | 13 | 55.8 | 0.022 | 1041 | 7.1 | 350 | 177 | |
| 13% Carbon Black | 13 | 25.3 | 0.025 | 184.3 | 3.6 | 450 | 232 | |
| | 13 | 29.0 | 0.024 | 263.6 | 4.1 | 465 | 241 | 4.1 |
| | 13 | 61.5 | 0.024 | 622 | 4.6 | 465 | 241 | |
| | 13 | 33.0 | 0.024 | 295.2 | 4.0 | 465 | 241 | |

As indicated above in Tables 7 and 8, when extruded at relatively low temperatures (e.g., 127-148° C.) carbon-blended Pebax® polymers having 10% and 13% carbon black demonstrated mean resistivity values which exceeded those suitable for electrode use. However, higher extrusion temperatures (e.g., 177-241° C.) resulted in extruded conductive polymers having mean resistivity values in a suitable range for electrode use.

Example 6

Resistivity Values for Extruded Carbon-Blended Pebax Polymer with Ag/AgCl

In order to determine the suitability for use in an electrode structure of an extruded conductive polymer having a blend of carbon black and Ag/AgCl, pellets of 10% carbon-blended Pebax® coated with Ag/AgCl ink were melted and extruded as a polymer string. The resulting extruded structure had a diameter of 0.05 cm and a length of 17.5 cm. When tested, the extruded conductive polymer had a resistance of 0.015 MΩ, and a determined resistivity of 1.67 Ω.cm. These results indicate that an extruded conductive polymer which includes a blend of carbon black and Ag/AgCl has resistivity characteristics making it suitable for use in an electrode structure.

Example 7

Resistance Measurements for Extruded Conductive Polymer Tubing

In order to determine resistance characteristics for extruded conductive tubing, Pebax® polymer was coextruded with 10% carbon-blended Pebax® polymer to produce a 0.88 mm diameter tube structure having two conductive stripes of 10% carbon-blended Pebax® positioned in the walls of the tube and electrically isolated from each other by the co-extruded Pebax® polymer. The conductive tubing was extruded such that the two conductive stripes extended the length of the tubing. Resistance was measured for each of the conductive stripes of the tubing. The results of these measurements are provided below in Table 9.

TABLE 9

| ID | Color 1 | Length 1 (mm) | Resistance 1 (kΩ) | Unit Resistance (kΩ/mm) | Color 2 | Length 2 (mm) | Resistance 2 (kΩ) | Unit Resistance (kΩ/mm) |
|---|---|---|---|---|---|---|---|---|
| A1 | black | 27 | 71.1 | 2.63 | red | 31 | 71.3 | 2.30 |
| A2 | yellow | 25 | 35.5 | 1.42 | red | 29 | 56.7 | 1.96 |
| A3 | yellow | 26 | 45.65 | 1.76 | red | 30 | 59.8 | 1.99 |
| A4 | black | 28 | 57.4 | 2.05 | red | 32 | 114.3 | 3.57 |

For each of the four extruded structures tested, each of the conductive stripes demonstrated a resistance value in a suitable range for use as an electrode, e.g., less than 40 kΩ/mm.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An electrode structure, comprising:
a first conductive material, a second conductive material, and a dielectric material,
wherein the first conductive material, the second conductive material, and the dielectric material are coextruded to provide an electrode structure having the first conductive material and the second conductive material electrically isolated by the dielectric material,
wherein the electrode structure comprises a lumen, the lumen comprising a first opening, a second opening, and a lumen wall defining an inner surface of the electrode structure,
wherein each of the first conductive material, the second conductive material, and the dielectric material define a portion of the lumen wall, and
wherein the first conductive material, the second conductive material, and the dielectric material extend from the inner surface to an outer surface of the electrode structure.

2. The electrode structure of claim 1, wherein the electrode structure comprises a hole extending through the dielectric material and at least substantially perpendicular to the lumen.

3. The electrode structure of claim 1, wherein the electrode structure comprises a rigid material provided in the dielectric material and coextruded with the first conductive material, the second conductive material, and the dielectric material.

4. The electrode structure of claim 3, wherein the electrode structure comprises a proximal end and a distal end, and wherein the rigid material protrudes from the proximal end of the electrode structure and functions as a lancet.

5. The electrode structure of claim 3, wherein the rigid material comprises a third conductive material.

6. The electrode structure of claim 5, wherein the electrode structure comprises a hole extending into the dielectric material and at least substantially perpendicular to the lumen, wherein the hole exposes the third conductive material.

7. The electrode structure of claim 1, wherein the first conductive material is positioned at least substantially opposite the second conductive material.

8. The electrode structure of claim 1, wherein the first conductive material comprises a working electrode and the second conductive material comprises a reference/counter electrode, the working electrode comprising an analyte responsive enzyme disposed on, in or proximate thereto.

9. The electrode structure of claim 8, wherein the first conductive material comprises carbon.

10. The electrode structure of claim 8, wherein the second conductive material comprises Ag/AgCl.

11. The electrode structure of claim 8, wherein the analyte-responsive enzyme is a glucose-responsive enzyme.

12. The electrode structure of claim 8, wherein the analyte-responsive enzyme is a ketone-responsive enzyme.

13. The electrode structure of claim 8, wherein the working electrode comprises a redox mediator disposed on, in or proximate thereto.

14. The electrode structure of claim 13, wherein the redox mediator comprises a ruthenium-containing complex or an osmium-containing complex.

15. The electrode structure of claim 1, wherein the dielectric material extends into the lumen beyond the portion of the lumen wall defined by the first conductive material and the portion of the lumen wall defined by the second conductive material, thereby providing at least two lancet stand-offs.

16. The electrode structure of claim 1, wherein the dielectric material and the first conductive material each extend into the lumen beyond the portion of the lumen wall defined by the second conductive material, thereby providing at least two lancet stand-offs.

17. The electrode structure of claim 1, wherein the dielectric material and the second conductive material each extend into the lumen beyond the portion of the lumen wall defined by the first conductive material, thereby providing at least two lancet stand-offs.

18. A method for determining a concentration of an analyte in a fluid sample from a subject, the method comprising:
    contacting the fluid sample with a sensor, the sensor comprising:
    an extruded electrode structure, the extruded electrode structure comprising:
        a first conductive material, a second conductive material, and a dielectric material,
        wherein the first conductive material, the second conductive material, and the dielectric material are coextruded to provide an electrode structure having the first conductive material and the second conductive material electrically isolated by the dielectric material,
        wherein the electrode structure comprises a lumen, the lumen comprising a first opening, a second opening, and a lumen wall defining an inner surface of the electrode structure,
        wherein each of the first conductive material, the second conductive material, and the dielectric material define a portion of the lumen wall,
        wherein the first conductive material, the second conductive material, and the dielectric material extend from the inner surface to an outer surface of the electrode structure, and
        wherein the first conductive material comprises a working electrode and the second conductive material comprises a reference/counter electrode, the working electrode comprising an analyte responsive enzyme disposed on, in or proximate thereto;
    generating a sensor signal at the working electrode; and
    determining the concentration of the analyte using the sensor signal.

19. The method of claim 18, wherein the electrode structure comprises a hole extending through the dielectric material and at least substantially perpendicular to the lumen.

20. The method of claim 18, wherein the electrode structure comprises a rigid material provided in the dielectric material and coextruded with the first conductive material, the second conductive material, and the dielectric material.

21. The method of claim 20, wherein the electrode structure comprises a proximal end and a distal end, and wherein the rigid material protrudes from the proximal end of the electrode structure and functions as a lancet.

22. The method of claim 20, wherein the rigid material comprises a third conductive material.

23. The method of claim 22, wherein the electrode structure comprises a hole extending into the dielectric material and at least substantially perpendicular to the lumen, wherein the hole exposes the third conductive material.

24. The method of claim 18, wherein the first conductive material is positioned at least substantially opposite the second conductive material.

25. The method of claim 18, wherein the first conductive material comprises carbon.

26. The method of claim 18, wherein the second conductive material comprises Ag/AgCl.

27. The method of claim 18, wherein the analyte-responsive enzyme is a glucose-responsive enzyme.

28. The method of claim 18, wherein the analyte-responsive enzyme is a ketone-responsive enzyme.

29. The method of claim 18, wherein the working electrode comprises a redox mediator disposed on, in or proximate thereto.

30. The method of claim 29, wherein the redox mediator comprises a ruthenium-containing complex or an osmium-containing complex.

31. The method of claim 18, wherein the dielectric material extends into the lumen beyond the portion of the lumen wall defined by the first conductive material and the portion of the lumen wall defined by the second conductive material, thereby providing at least two lancet stand-offs.

32. The method of claim 18, wherein the dielectric material and the first conductive material each extend into the lumen beyond the portion of the lumen wall defined by the second conductive material, thereby providing at least two lancet stand-offs.

33. The method of claim 18, wherein the dielectric material and the second conductive material each extend into the lumen beyond the portion of the lumen wall defined by the first conductive material, thereby providing at least two lancet stand-offs.

* * * * *